United States Patent [19]
Heinemann et al.

[11] Patent Number: 5,945,509
[45] Date of Patent: Aug. 31, 1999

[54] GLUTAMATE RECEPTOR COMPOSITIONS AND METHOD

[75] Inventors: Stephen F. Heinemann, La Jolla; James R. Boulter, San Diego; Michael Hollmann, Del Mar; Bernhard Bettler, Solana Beach; Jan Egebejerg Jensen, San Diego, all of Calif.

[73] Assignee: The Salk Institute for Biological Studies, La Jolla, Calif.

[21] Appl. No.: 08/486,269

[22] Filed: Jun. 6, 1995

Related U.S. Application Data

[62] Division of application No. 08/013,767, Feb. 4, 1993, abandoned, which is a division of application No. 07/718,575, filed as application No. PCT/US90/06153, Oct. 25, 1990, Pat. No. 5,202,257, which is a continuation-in-part of application No. 07/428,116, Oct. 27, 1989, abandoned.

[51] Int. Cl.⁶ .................... C07K 14/705; C12N 15/12
[52] U.S. Cl. .................... 530/350; 435/69.1; 536/23.5
[58] Field of Search ..................... 435/69.1, 7.2; 530/350; 436/501

[56] References Cited

PUBLICATIONS

Grenningloh et al. Alpha subunit variants of the human glycine receptor: primary structures, functional expression an chromosomal localization of the corresponding genes. The EMBO Journal 9(3):771–776, Mar. 1990.

Schofield et al. Sequence and expression of human GABA–A receptor alpha1 and beta1 subunits. FEBS Letters 244(2):361–364, FEB. 1989.

Huetther et al. P.N.A.S. 85:1307–1311, Feb. 1988.

Primary Examiner—John Ulm
Attorney, Agent, or Firm—Gray Cary Ware & Freidenrich; Stephen E. Reiter

[57] ABSTRACT

The present invention discloses novel DNAs that encode proteins having electrophysiological and pharmacological properties characteristic of glutamate receptors. The glutamate receptors are exemplified by proteins encoded by representative cDNA clones GluR1, GluR2, GluR3, GluR4, GluR5, GluR6 and GluR7, fragments thereof, and functional combinations of these glutamate receptor proteins and/or fragments. DNA sequences from the cDNA clones for GluR1, GluR2, GluR3, GluR4 and GluR5 are especially useful as probes, thus enabling those skilled in the art to identify, without undue experimentation, other members of the L-glutamate receptor family.

12 Claims, 19 Drawing Sheets

|           |   |   |   |   |   |   |   |   |   |   |   |   |   |   |
|-----------|---|---|---|---|---|---|---|---|---|---|---|---|---|---|
| GluR-1    | . | C | F | I | T | P | S | - | F | P | V | D | T | S | N | Q | . |
| nAChR-α1  | . | C | E | I | I | V | T | H | F | P | F | D | E | Q | Q | N | . |
| nAChR-α2  | . | C | S | I | D | V | T | F | F | P | F | D | D | Q | Y | N | . |
| nAChR-α3  | . | C | K | I | D | V | T | Y | F | P | F | D | D | Q | Q | N | . |
| nAChR-α4  | . | C | S | I | D | V | T | F | F | P | F | D | D | Q | W | N | . |
| nAChR-β1  | . | C | S | I | Q | V | T | Y | F | P | F | D | D | Q | Q | N | . |
| nAChR-β2  | . | C | K | I | E | V | K | H | F | P | F | D | D | R | Q | N | . |
| nAChR-β3  | . | C | T | M | D | V | T | F | F | P | F | D | Q | Q | Q | N | . |
| nAChR-β4  | . | C | K | I | E | V | K | H | F | P | F | D | D | Q | W | N | . |
| nAChR-γ   | . | C | P | I | A | V | T | Y | F | P | F | D | W | Q | N | C | . |
| nAChR-δ   | . | C | P | I | S | V | T | Y | F | P | F | D | W | Q | N | C | . |
| GABA-α    | . | C | P | M | H | L | E | D | F | P | M | D | A | H | A | C | . |
| GABA-β    | . | C | M | M | D | L | R | R | Y | P | L | D | E | Q | N | C | . |
| GlyR 48k  | . | C | P | M | D | L | K | N | F | P | M | D | V | Q | T | C | . |

Figure 1A

```
                 .   .           .   .      .   .
GluR-1       ..YEIWM-CIVFAYIGVSVLFLVSRFSP..
nAChR-α1     ..GEKMTLSI-SVLLSLTVFLLVIVELIP..
nAChR-α2     ..GEKITLCI-SVLLSLTVFLLITEIIP..
nAChR-α3     ..GEKVTLCI-SVLLSLTVFLLVITETIP..
nAChR-α4     ..GEKVTLCI-SVLLSLTVFLLITEIIP..
nAChR-β1     ..GEKMGLSI-FALLTLTVFLLLLADKVP..
nAChR-β2     ..GEKMTLCI-SVLLALTVFLLLISKIVP..
nAChR-β3     ..GEKLSLST-SVLVSLTVFLLVIEEIIP..
nAChR-β4     ..GEKMTLCI-SYLLSLTVFFLLISKIVP..
nAChR-γ      ..GQKCTVAT-NVLLAQTVFLFLVAKKVP..
nAChR-δ      ..GEKTSVAI-SVLLAQSVFLLLISKRLP..
GABA-α       ..NRESVPAR-TVFGVTTVLTMTTLSISA..
GABA-β       ..NYDASAARV-ALGITTVLTMTTISTHL..
GlyR 48k     ..NMDAAPARV-GLGITTVLTMTTQSSGS..
```

```
R1                              MPYIFAFFCTGFLGAVVG
R2                      MQKIMHISVLLSPVLWGLIFG
R3              MGQSVLRAVFFLVLGLLGHSHG
R4              MRIICRQIVLLFSGFSGTRHG
R5       MERSTVLIQPGLWTRDTSWTLLYFLCYILP
R6       MKIISPVLSNLVFSRSIKVLLCLLWIGYSQG
R7  GAVAGSLGRIRSLVWEYWAGFLVCAFWIPDSRG
```

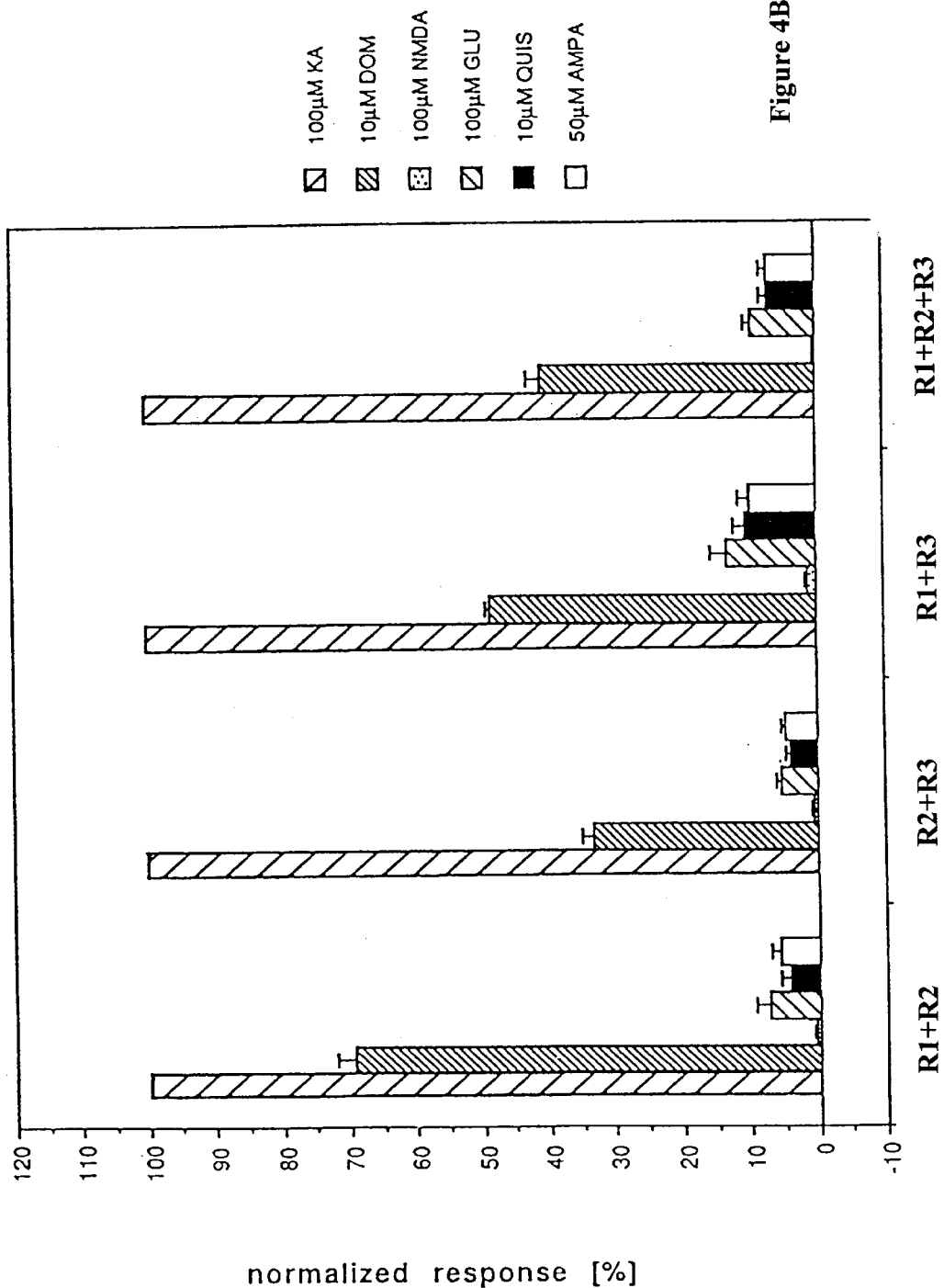

FIGURE 6-1

GluR1: F P K S M Q S I P C M S H S S G M P L G A T G L
GluR2: T Q R K E T V A
GluR6:
GluR7: D R R L P G K D S M S C S T S L A P V F P

FIGURE 6-4

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 2992 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: GluR1

(ix) FEATURE:
        (A) NAME/KEY: Coding Sequence
        (B) LOCATION: 198...2918
        (D) OTHER INFORMATION:

(xi) SEQUENCE DESCRIPTION: SEQ ID NO:1:

```
AATTCGGCAC GAGCTCGGCT CCCCTTCCAA GAGAAACAAG AGAAACCTCA CGGAAGGAAG      60

GGAGGAAGGA AAGAAGCAAG CAAGGAACTG CAGGAAGAAA AGAGCCGGCA GAGCATCAAG     120

AAGAATCGAA GGGAGGGGAG GGAAGACCAA ATCTATGGTT GGACCAGGGC TTCTTTTTCG     180

CCAATGTAAA AAGGAAT ATG CCG TAC ATC TTT GCC TTT TTC TGC ACC GGT        230
                Met Pro Tyr Ile Phe Ala Phe Phe Cys Thr Gly
                  1               5                  10

TTT CTA GGT GCG GTT GTG GGT GCC AAT TTC CCC AAC AAT ATC CAG ATA       278
Phe Leu Gly Ala Val Val Gly Ala Asn Phe Pro Asn Asn Ile Gln Ile
              15                  20                  25

GGG GGG TTA TTT CCA AAC CAA CAA TCA CAG GAA CAT GCG GCT TTT AGG       326
Gly Gly Leu Phe Pro Asn Gln Gln Ser Gln Glu His Ala Ala Phe Arg
          30                  35                  40

TTT GCT TTG TCA CAA CTC ACG GAG CCC CCC AAG CTG CTT CCC CAG ATC       374
Phe Ala Leu Ser Gln Leu Thr Glu Pro Pro Lys Leu Leu Pro Gln Ile
      45                  50                  55

GAT ATT GTG AAC ATC AGC GAC ACG TTT GAG ATG ACT TAC CGT TTC TGT       422
Asp Ile Val Asn Ile Ser Asp Thr Phe Glu Met Thr Tyr Arg Phe Cys
60                  65                  70                  75

TCC CAG TTC TCC AAA GGA GTC TAT GCC ATC TTT GGA TTT TAT GAA CGA       470
Ser Gln Phe Ser Lys Gly Val Tyr Ala Ile Phe Gly Phe Tyr Glu Arg
                  80                  85                  90

AGG ACT GTC AAC ATG CTG ACC TCC TTC TGT GGG GCC CTC CAT GTG TGC       518
Arg Thr Val Asn Met Leu Thr Ser Phe Cys Gly Ala Leu His Val Cys
              95                 100                 105

TTC ATT ACT CCA AGT TTT CCT GTT GAC ACA TCC AAT CAA TTT GTC CTT       566
Phe Ile Thr Pro Ser Phe Pro Val Asp Thr Ser Asn Gln Phe Val Leu
         110                 115                 120

CAG CTA CGC CCG GAA CTA CAG GAA GCT CTC ATT AGC ATT ATC GAC CAT       614
Gln Leu Arg Pro Glu Leu Gln Glu Ala Leu Ile Ser Ile Ile Asp His
     125                 130                 135

TAC AAG TGG CAA ACC TTT GTC TAC ATT TAT GAT GCT GAC CGG GGC CTG       662
Tyr Lys Trp Gln Thr Phe Val Tyr Ile Tyr Asp Ala Asp Arg Gly Leu
140                 145                 150                 155

TCA GTC CTG CAG AGA GTC TTG GAT ACA GCC GCA GAG AAG AAC TGG CAG       710
Ser Val Leu Gln Arg Val Leu Asp Thr Ala Ala Glu Lys Asn Trp Gln
                 160                 165                 170

GTA ACG GCT GTC AAC ATT CTG ACA ACC ACC GAG GAA GGA TAC CGG ATG       758
Val Thr Ala Val Asn Ile Leu Thr Thr Thr Glu Glu Gly Tyr Arg Met
```

```
                  175                 180                 185
CTC TTT CAG GAC CTG GAG AAG AAA AAG GAG AGG CTG GTG GTG GTT GAC         806
Leu Phe Gln Asp Leu Glu Lys Lys Lys Glu Arg Leu Val Val Val Asp
        190                 195                 200

TGT GAA TCA GAA CGC CTC AAC GCC ATC CTG GGC CAG ATC GTG AAG CTA         854
Cys Glu Ser Glu Arg Leu Asn Ala Ile Leu Gly Gln Ile Val Lys Leu
205                 210                 215

GAA AAG AAT GGC ATC GGG TAC CAC TAC ATC CTC GCC AAT CTG GGC TTC         902
Glu Lys Asn Gly Ile Gly Tyr His Tyr Ile Leu Ala Asn Leu Gly Phe
220                 225                 230                 235

ATG GAC ATT GAC TTA AAT AAG TTC AAG GAG AGC GGA CGC AAT GTG ACA         950
Met Asp Ile Asp Leu Asn Lys Phe Lys Glu Ser Gly Arg Asn Val Thr
            240                 245                 250

GGT TTC CAG CTG GTG AAC TAC ACA GAC ACG ATC CCA GCC AGA ATC ATG         998
Gly Phe Gln Leu Val Asn Tyr Thr Asp Thr Ile Pro Ala Arg Ile Met
        255                 260                 265

CAG CAA TGG AGG ACA AGT GAC TCC CGA GAC CAT ACC AGG GTG GAC TGG        1046
Gln Gln Trp Arg Thr Ser Asp Ser Arg Asp His Thr Arg Val Asp Trp
            270                 275                 280

AAG AGG CCA AAG TAC ACT TCT GCT CTC ACC TAT GAT GGT GTC AAG GTG        1094
Lys Arg Pro Lys Tyr Thr Ser Ala Leu Thr Tyr Asp Gly Val Lys Val
        285                 290                 295

ATG GCT GAG GCC TTC CAA AGC CTG CGG AGG CAG AGG ATT GAC ATA TCC        1142
Met Ala Glu Ala Phe Gln Ser Leu Arg Arg Gln Arg Ile Asp Ile Ser
300                 305                 310                 315

CGC CGG GGG AAT GCT GGG GAC TGT CTG GCT AAC CCA GCT GTG CCC TGG        1190
Arg Arg Gly Asn Ala Gly Asp Cys Leu Ala Asn Pro Ala Val Pro Trp
            320                 325                 330

GGT CAA GGG ATC GAC ATC CAG AGA GCC CTG CAG CAG GTG CGC TTC GAA        1238
Gly Gln Gly Ile Asp Ile Gln Arg Ala Leu Gln Gln Val Arg Phe Glu
            335                 340                 345

GGT TTG ACA GGA AAT GTG CAG TTC AAC GAG AAA GGG CGC CGG ACC AAT        1286
Gly Leu Thr Gly Asn Val Gln Phe Asn Glu Lys Gly Arg Arg Thr Asn
        350                 355                 360

TAC ACC CTC CAC GTG ATC GAA ATG AAA CAT GAT GGA ATC CGA AAG ATT        1334
Tyr Thr Leu His Val Ile Glu Met Lys His Asp Gly Ile Arg Lys Ile
        365                 370                 375

GGT TAC TGG AAT GAA GAC GAT AAA TTT GTC CCC GCA GCC ACC GAC GCT        1382
Gly Tyr Trp Asn Glu Asp Asp Lys Phe Val Pro Ala Ala Thr Asp Ala
380                 385                 390                 395

CAG GCT GGA GGG GAC AAC TCA AGC GTC CAG AAT AGG ACC TAC ATC GTC        1430
Gln Ala Gly Gly Asp Asn Ser Ser Val Gln Asn Arg Thr Tyr Ile Val
                400                 405                 410

ACT ACT ATC CTC GAA GAT CCT TAC GTG ATG CTT AAA AAG AAT GCC AAC        1478
Thr Thr Ile Leu Glu Asp Pro Tyr Val Met Leu Lys Lys Asn Ala Asn
            415                 420                 425

CAG TTT GAG GGC AAT GAC CGC TAT GAG GGC TAC TGT GTG GAG CTG GCT        1526
Gln Phe Glu Gly Asn Asp Arg Tyr Glu Gly Tyr Cys Val Glu Leu Ala
        430                 435                 440

GCA GAG ATC GCC AAG CAC GTG GGC TAC TCC TAC CGA CTT GAG ATT GTC        1574
Ala Glu Ile Ala Lys His Val Gly Tyr Ser Tyr Arg Leu Glu Ile Val
        445                 450                 455

AGC GAC GGC AAA TAT GGA GCC CGG GAT CCC GAC ACA AAG GCT TGG AAT        1622
Ser Asp Gly Lys Tyr Gly Ala Arg Asp Pro Asp Thr Lys Ala Trp Asn
460                 465                 470                 475

GGC ATG GTG GGA GAA CTG GTC TAT GGA AGA GCA GAC GTG GCT GTG GCT        1670
Gly Met Val Gly Glu Leu Val Tyr Gly Arg Ala Asp Val Ala Val Ala
                480                 485                 490

CCC TTG ACC ATA ACC TTG GTC CGG GAG GAA GTC ATC GAC TTC TCC AAG        1718
Pro Leu Thr Ile Thr Leu Val Arg Glu Glu Val Ile Asp Phe Ser Lys
```

-continued

```
                495                 500                      505
CCA TTC ATG AGT TTG GGA ATC TCC ATT ATG ATT AAG AAG CCA CAG AAG      1766
Pro Phe Met Ser Leu Gly Ile Ser Ile Met Ile Lys Lys Pro Gln Lys
            510                 515                 520

TCC AAG CCA GGT GTC TTC TCC TTT CTT GAC CCT TTG GCC TAT GAG ATC      1814
Ser Lys Pro Gly Val Phe Ser Phe Leu Asp Pro Leu Ala Tyr Glu Ile
525                 530                 535

TGG ATG TGT ATA GTG TTT GCC TAC ATT GGA GTG AGC GTC GTC CTC TTC      1862
Trp Met Cys Ile Val Phe Ala Tyr Ile Gly Val Ser Val Val Leu Phe
540                 545                 550                 555

CTG GTC AGC CGT TTC AGC CCC TAC GAA TGG CAC AGC GAA GAG TTT GAA      1910
Leu Val Ser Arg Phe Ser Pro Tyr Glu Trp His Ser Glu Glu Phe Glu
            560                 565                 570

GAG GGA CGA GAC CAG ACA ACC AGT GAC CAG TCA AAT GAG TTT GGC ATA      1958
Glu Gly Arg Asp Gln Thr Thr Ser Asp Gln Ser Asn Glu Phe Gly Ile
            575                 580                 585

TTC AAC AGC CTG TGG TTC TCC CTG GGG GCC TTC ATG CAG CAA GGA TGT      2006
Phe Asn Ser Leu Trp Phe Ser Leu Gly Ala Phe Met Gln Gln Gly Cys
            590                 595                 600

GAC ATT TCC CCC AGG TCC CTG TCC GGA CGC ATC GTC GGC GGC GTC TGG      2054
Asp Ile Ser Pro Arg Ser Leu Ser Gly Arg Ile Val Gly Gly Val Trp
605                 610                 615

TGG TTC TTC ACT TTG ATC ATC ATC TCC TCG TAC ACA GCC AAC CTG GCT      2102
Trp Phe Phe Thr Leu Ile Ile Ile Ser Ser Tyr Thr Ala Asn Leu Ala
620                 625                 630                 635

GCC TTC CTG ACT GTG GAG AGG ATG GTG TCT CCC ATT GAG AGT GCA GAG      2150
Ala Phe Leu Thr Val Glu Arg Met Val Ser Pro Ile Glu Ser Ala Glu
            640                 645                 650

GAC CTG GCA AAG CAG ACG GAA ATT GCT TAT GGG ACA TTG GAA GCA GGC      2198
Asp Leu Ala Lys Gln Thr Glu Ile Ala Tyr Gly Thr Leu Glu Ala Gly
            655                 660                 665

TCC ACT AAG GAG TTC TTC AGG AGA TCT AAA ATC GCT GTG TTT GAG AAG      2246
Ser Thr Lys Glu Phe Phe Arg Arg Ser Lys Ile Ala Val Phe Glu Lys
            670                 675                 680

ATG TGG ACA TAC ATG AAG TCT GCA GAA CCA TCC GTG TTT GTT CGG ACC      2294
Met Trp Thr Tyr Met Lys Ser Ala Glu Pro Ser Val Phe Val Arg Thr
685                 690                 695

ACA GAG GAA GGC ATG ATC AGA GTG AGA AAA TCT AAA GGC AAA TAC GCC      2342
Thr Glu Glu Gly Met Ile Arg Val Arg Lys Ser Lys Gly Lys Tyr Ala
700                 705                 710                 715

TAC CTC CTG GAG TCC ACC ATG AAT GAG TAT ATT GAG CAA CGA AAG CCC      2390
Tyr Leu Leu Glu Ser Thr Met Asn Glu Tyr Ile Glu Gln Arg Lys Pro
                720                 725                 730

TGT GAC ACC ATG AAA GTG GGA GGT AAC TTG GAT TCC AAA GGC TAT GGC      2438
Cys Asp Thr Met Lys Val Gly Gly Asn Leu Asp Ser Lys Gly Tyr Gly
            735                 740                 745

ATT GCG ACA CCC AAG GGG TCC GCC CTG AGA AAT CCA GTA AAC CTG GCA      2486
Ile Ala Thr Pro Lys Gly Ser Ala Leu Arg Asn Pro Val Asn Leu Ala
            750                 755                 760

GTG TTA AAA CTG AAC GAG CAG GGG CTT TTG GAC AAA TTG AAA AAC AAA      2534
Val Leu Lys Leu Asn Glu Gln Gly Leu Leu Asp Lys Leu Lys Asn Lys
765                 770                 775

TGG TGG TAC GAC AAG GGC GAG TGC GGC ACG GGG GGA GGT GAC TCC AAG      2582
Trp Trp Tyr Asp Lys Gly Glu Cys Gly Thr Gly Gly Gly Asp Ser Lys
780                 785                 790                 795

GAC AAG ACC AGC GCT TTG AGC CTC AGC AAT GTG GCA GGC GTG TTC TAC      2630
Asp Lys Thr Ser Ala Leu Ser Leu Ser Asn Val Ala Gly Val Phe Tyr
            800                 805                 810

ATC CTG ATT GGA GGG CTG GGA CTG GCC ATG CTG GTT GCC TTA ATC GAG      2678
Ile Leu Ile Gly Gly Leu Gly Leu Ala Met Leu Val Ala Leu Ile Glu
```

```
                  815                 820                 825
TTC TGC TAC AAA TCC CGT AGC GAG TCG AAG CGG ATG AAG GGT TTC TGT    2726
Phe Cys Tyr Lys Ser Arg Ser Glu Ser Lys Arg Met Lys Gly Phe Cys
        830                 835                 840

TTG ATC CCA CAG CAA TCC ATC AAT GAA GCC ATA CGG ACA TCG ACC CTC    2774
Leu Ile Pro Gln Gln Ser Ile Asn Glu Ala Ile Arg Thr Ser Thr Leu
        845                 850                 855

CCC CGG AAC AGT GGG GCA GGA GCC AGC GGA GGA GGC GGC AGT GGA GAG    2822
Pro Arg Asn Ser Gly Ala Gly Ala Ser Gly Gly Gly Gly Ser Gly Glu
860                 865                 870                 875

AAT GGC CGG GTG GTC AGC CAG GAC TTC CCC AAG TCC ATG CAA TCC ATT    2870
Asn Gly Arg Val Val Ser Gln Asp Phe Pro Lys Ser Met Gln Ser Ile
                880                 885                 890

CCC TGC ATG AGT CAC AGT TCA GGG ATG CCC TTG GGA GCC ACA GGA TTG T  2919
Pro Cys Met Ser His Ser Ser Gly Met Pro Leu Gly Ala Thr Gly Leu
                895                 900                 905

AACTGGAGCA GACAGGAAAC CCTTGGGGAG CAGGCTCAGG CTTCCACAGC CCCATCCCAA  2979

GCCCTTCAGT GCC                                                    2992

(2) INFORMATION FOR SEQ ID NO:2:

(i) SEQUENCE CHARACTERISTICS:
        (A) LENGTH: 907 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Pro Tyr Ile Phe Ala Phe Phe Cys Thr Gly Phe Leu Gly Ala Val
1               5                   10                  15

Val Gly Ala Asn Phe Pro Asn Asn Ile Gln Ile Gly Gly Leu Phe Pro
                20                  25                  30

Asn Gln Gln Ser Gln Glu His Ala Ala Phe Arg Phe Ala Leu Ser Gln
            35                  40                  45

Leu Thr Glu Pro Pro Lys Leu Leu Pro Gln Ile Asp Ile Val Asn Ile
        50                  55                  60

Ser Asp Thr Phe Glu Met Thr Tyr Arg Phe Cys Ser Gln Phe Ser Lys
65                  70                  75                  80

Gly Val Tyr Ala Ile Phe Gly Phe Tyr Glu Arg Arg Thr Val Asn Met
                85                  90                  95

Leu Thr Ser Phe Cys Gly Ala Leu His Val Cys Phe Ile Thr Pro Ser
            100                 105                 110

Phe Pro Val Asp Thr Ser Asn Gln Phe Val Leu Gln Leu Arg Pro Glu
        115                 120                 125

Leu Gln Glu Ala Leu Ile Ser Ile Ile Asp His Tyr Lys Trp Gln Thr
130                 135                 140

Phe Val Tyr Ile Tyr Asp Ala Asp Arg Gly Leu Ser Val Leu Gln Arg
145                 150                 155                 160

Val Leu Asp Thr Ala Ala Glu Lys Asn Trp Gln Val Thr Ala Val Asn
                165                 170                 175

Ile Leu Thr Thr Thr Glu Glu Gly Tyr Arg Met Leu Phe Gln Asp Leu
            180                 185                 190

Glu Lys Lys Lys Glu Arg Leu Val Val Val Asp Cys Glu Ser Glu Arg
        195                 200                 205

Leu Asn Ala Ile Leu Gly Gln Ile Val Lys Leu Glu Lys Asn Gly Ile
210                 215                 220
```

```
Gly Tyr His Tyr Ile Leu Ala Asn Leu Gly Phe Met Asp Ile Asp Leu
225                 230                 235                 240

Asn Lys Phe Lys Glu Ser Gly Arg Asn Val Thr Gly Phe Gln Leu Val
            245                 250                 255

Asn Tyr Thr Asp Thr Ile Pro Ala Arg Ile Met Gln Gln Trp Arg Thr
        260                 265                 270

Ser Asp Ser Arg Asp His Thr Arg Val Asp Trp Lys Arg Pro Lys Tyr
    275                 280                 285

Thr Ser Ala Leu Thr Tyr Asp Gly Val Lys Val Met Ala Glu Ala Phe
290                 295                 300

Gln Ser Leu Arg Arg Gln Arg Ile Asp Ile Ser Arg Arg Gly Asn Ala
305                 310                 315                 320

Gly Asp Cys Leu Ala Asn Pro Ala Val Pro Trp Gly Gln Gly Ile Asp
            325                 330                 335

Ile Gln Arg Ala Leu Gln Gln Val Arg Phe Glu Gly Leu Thr Gly Asn
        340                 345                 350

Val Gln Phe Asn Glu Lys Gly Arg Arg Thr Asn Tyr Thr Leu His Val
    355                 360                 365

Ile Glu Met Lys His Asp Gly Ile Arg Lys Ile Gly Tyr Trp Asn Glu
370                 375                 380

Asp Asp Lys Phe Val Pro Ala Ala Thr Asp Ala Gln Ala Gly Gly Asp
385                 390                 395                 400

Asn Ser Ser Val Gln Asn Arg Thr Tyr Ile Val Thr Thr Ile Leu Glu
            405                 410                 415

Asp Pro Tyr Val Met Leu Lys Lys Asn Ala Asn Gln Phe Glu Gly Asn
        420                 425                 430

Asp Arg Tyr Glu Gly Tyr Cys Val Glu Leu Ala Ala Glu Ile Ala Lys
    435                 440                 445

His Val Gly Tyr Ser Tyr Arg Leu Glu Ile Val Ser Asp Gly Lys Tyr
450                 455                 460

Gly Ala Arg Asp Pro Asp Thr Lys Ala Trp Asn Gly Met Val Gly Glu
465                 470                 475                 480

Leu Val Tyr Gly Arg Ala Asp Val Ala Val Ala Pro Leu Thr Ile Thr
            485                 490                 495

Leu Val Arg Glu Glu Val Ile Asp Phe Ser Lys Pro Phe Met Ser Leu
        500                 505                 510

Gly Ile Ser Ile Met Ile Lys Lys Pro Gln Lys Ser Lys Pro Gly Val
    515                 520                 525

Phe Ser Phe Leu Asp Pro Leu Ala Tyr Glu Ile Trp Met Cys Ile Val
530                 535                 540

Phe Ala Tyr Ile Gly Val Ser Val Val Leu Phe Leu Val Ser Arg Phe
545                 550                 555                 560

Ser Pro Tyr Glu Trp His Ser Glu Gly Phe Glu Gly Arg Asp Gln
            565                 570                 575

Thr Thr Ser Asp Gln Ser Asn Glu Phe Gly Ile Phe Asn Ser Leu Trp
        580                 585                 590

Phe Ser Leu Gly Ala Phe Met Gln Gln Gly Cys Asp Ile Ser Pro Arg
    595                 600                 605

Ser Leu Ser Gly Arg Ile Val Gly Gly Val Trp Trp Phe Phe Thr Leu
610                 615                 620

Ile Ile Ile Ser Ser Tyr Thr Ala Asn Leu Ala Ala Phe Leu Thr Val
625                 630                 635                 640

Glu Arg Met Val Ser Pro Ile Glu Ser Ala Glu Asp Leu Ala Lys Gln
```

-continued

```
                    645                 650                 655
    Thr Glu Ile Ala Tyr Gly Thr Leu Glu Ala Gly Ser Thr Lys Glu Phe
                    660                 665                 670

Phe Arg Arg Ser Lys Ile Ala Val Phe Glu Lys Met Trp Thr Tyr Met
                    675                 680                 685

Lys Ser Ala Glu Pro Ser Val Phe Val Arg Thr Thr Glu Glu Gly Met
                    690                 695             700

Ile Arg Val Arg Lys Ser Lys Gly Lys Tyr Ala Tyr Leu Leu Glu Ser
    705                 710                 715                 720

Thr Met Asn Glu Tyr Ile Glu Gln Arg Lys Pro Cys Asp Thr Met Lys
                    725                 730                 735

Val Gly Gly Asn Leu Asp Ser Lys Gly Tyr Gly Ile Ala Thr Pro Lys
                    740                 745                 750

Gly Ser Ala Leu Arg Asn Pro Val Asn Leu Ala Val Leu Lys Leu Asn
                    755                 760                 765

Glu Gln Gly Leu Leu Asp Lys Leu Lys Asn Lys Trp Trp Tyr Asp Lys
                    770                 775                 780

Gly Glu Cys Gly Thr Gly Gly Gly Asp Ser Lys Asp Lys Thr Ser Ala
    785                 790                 795                 800

Leu Ser Leu Ser Asn Val Ala Gly Val Phe Tyr Ile Leu Ile Gly Gly
                    805                 810                 815

Leu Gly Leu Ala Met Leu Val Ala Leu Ile Glu Phe Cys Tyr Lys Ser
                    820                 825                 830

Arg Ser Glu Ser Lys Arg Met Lys Gly Phe Cys Leu Ile Pro Gln Gln
                    835                 840                 845

Ser Ile Asn Glu Ala Ile Arg Thr Ser Thr Leu Pro Arg Asn Ser Gly
    850                 855                 860

Ala Gly Ala Ser Gly Gly Gly Gly Ser Gly Glu Asn Gly Arg Val Val
    865                 870                 875                 880

Ser Gln Asp Phe Pro Lys Ser Met Gln Ser Ile Pro Cys Met Ser His
                    885                 890                 895

Ser Ser Gly Met Pro Leu Gly Ala Thr Gly Leu
                    900                 905

(2) INFORMATION FOR SEQ ID NO:3:

(i) SEQUENCE CHARACTERISTICS:
        (A) LENGTH: 3505 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: GluR2

(ix) FEATURE:
        (A) NAME/KEY: Coding Sequence
        (B) LOCATION: 316...2964
        (D) OTHER INFORMATION:

(xi) SEQUENCE DESCRIPTION: SEQ ID NO:3:

GAATTCGGCA CGAGGTGCAT GGGAGGGTGC TGATATTCCC AGACACCAGG ACTACAGCGG      60

CAGCTCAGCT AAAAACTGCA TTCAGCCAGT CCTCGGGACT TCGGGAGCAG GACAGGACG      120

CAAGGCATCA ACAGCCACCA GCTACAACTG GAAATAAGG ATTCTTCTGC CTTCACTTCG      180

TGTTTTTAGC AGCTCCTTGC TAAATATCGA CCTCACAATG CAGAGGATCT AATTTGCTGA      240

GGAAAACAGT CAAAGAAGGA AGAGGAAGAA AGGGAAACGA GGGGATATTT TGTGGATGCT      300
```

```
CTACTTTTCT TGGAA ATG CAA AAG ATT ATG CAT ATT TCT GTC CTC CTT TCT          351
               Met Gln Lys Ile Met His Ile Ser Val Leu Leu Ser
                 1               5                  10

CCT GTT TTA TGG GGA CTG ATT TTT GGT GTC TCT TCT AAC AGC ATA CAG          399
Pro Val Leu Trp Gly Leu Ile Phe Gly Val Ser Ser Asn Ser Ile Gln
         15                  20                  25

ATA GGG GGG CTA TTT CCA AGG GGC GCT GAT CAA GAA TAC AGT GCA TTT          447
Ile Gly Gly Leu Phe Pro Arg Gly Ala Asp Gln Glu Tyr Ser Ala Phe
     30                  35                  40

CGG GTA GGG ATG GTT CAG TTT TCC ACT TCG GAG TTC AGA CTG ACA CCC          495
Arg Val Gly Met Val Gln Phe Ser Thr Ser Glu Phe Arg Leu Thr Pro
 45                  50                  55                  60

CAT ATC GAC AAT TTG GAG GTA GCC AAC AGT TTC GCA GTC ACC AAT GCT          543
His Ile Asp Asn Leu Glu Val Ala Asn Ser Phe Ala Val Thr Asn Ala
                 65                  70                  75

TTC TGC TCC CAG TTT TCA AGA GGA GTC TAC GCA ATT TTT GGA TTT TAT          591
Phe Cys Ser Gln Phe Ser Arg Gly Val Tyr Ala Ile Phe Gly Phe Tyr
             80                  85                  90

GAC AAG AAG TCT GTA AAT ACC ATC ACA TCA TTC TGT GGG ACA CTC CAT          639
Asp Lys Lys Ser Val Asn Thr Ile Thr Ser Phe Cys Gly Thr Leu His
         95                 100                 105

GTG TCC TTC ATC ACA CCT AGC TTC CCA ACA GAT GGC ACA CAT CCA TTT          687
Val Ser Phe Ile Thr Pro Ser Phe Pro Thr Asp Gly Thr His Pro Phe
     110                 115                 120

GTC ATC CAG ATG CGA CCT GAC CTC AAA GGA GCA CTC CTT AGC TTG ATT          735
Val Ile Gln Met Arg Pro Asp Leu Lys Gly Ala Leu Leu Ser Leu Ile
125                 130                 135                 140

GAG TAC TAC CAA TGG GAC AAG TTC GCA TAC CTC TAT GAC AGT GAC AGA          783
Glu Tyr Tyr Gln Trp Asp Lys Phe Ala Tyr Leu Tyr Asp Ser Asp Arg
                145                 150                 155

GGC TTA TCA ACA CTG CAA GCT GTT CTG GAT TCT GCT GCA GAG AAG AAG          831
Gly Leu Ser Thr Leu Gln Ala Val Leu Asp Ser Ala Ala Glu Lys Lys
            160                 165                 170

TGG CAG GTG ACT GCT ATC AAT GTG GGG AAC ATC AAC AAT GAC AAG AAA          879
Trp Gln Val Thr Ala Ile Asn Val Gly Asn Ile Asn Asn Asp Lys Lys
        175                 180                 185

GAT GAG ACC TAC AGA TCG CTC TTT CAA GAT CTG GAG TTA AAA AAA GAA          927
Asp Glu Thr Tyr Arg Ser Leu Phe Gln Asp Leu Glu Leu Lys Lys Glu
    190                 195                 200

CGG CGT GTA ATC CTG GAC TGT GAA AGG GAT AAA GTA AAT GAC ATT GTG          975
Arg Arg Val Ile Leu Asp Cys Glu Arg Asp Lys Val Asn Asp Ile Val
205                 210                 215                 220

GAC CAG GTT ATT ACC ATT GGA AAA CAT GTT AAA GGG TAC CAT TAT ATC         1023
Asp Gln Val Ile Thr Ile Gly Lys His Val Lys Gly Tyr His Tyr Ile
                225                 230                 235

ATT GCA AAT CTG GGA TTC ACT GAT GGG GAC CTG CTG AAA ATT CAG TTT         1071
Ile Ala Asn Leu Gly Phe Thr Asp Gly Asp Leu Leu Lys Ile Gln Phe
            240                 245                 250

GGA GGA GCA AAT GTC TCT GGA TTT CAG ATT GTA GAC TAC GAC GAT TCC         1119
Gly Gly Ala Asn Val Ser Gly Phe Gln Ile Val Asp Tyr Asp Asp Ser
        255                 260                 265

CTG GTG TCT AAA TTT ATA GAA AGA TGG TCA ACA CTG GAA GAG AAA GAA         1167
Leu Val Ser Lys Phe Ile Glu Arg Trp Ser Thr Leu Glu Glu Lys Glu
    270                 275                 280

TAC CCT GGA GCA CAC ACA GCG ACA ATT AAG TAT ACT TCG GCC CTG ACG         1215
Tyr Pro Gly Ala His Thr Ala Thr Ile Lys Tyr Thr Ser Ala Leu Thr
285                 290                 295                 300

TAT GAT GCT GTC CAA GTG ATG ACT GAA GCA TTC CGT AAC CTT CGG AAG         1263
Tyr Asp Ala Val Gln Val Met Thr Glu Ala Phe Arg Asn Leu Arg Lys
                305                 310                 315
```

```
CAG AGG ATT GAA ATA TCC CGG AGA GGA AAT GCA GGG GAT TGT TTG GCC    1311
Gln Arg Ile Glu Ile Ser Arg Arg Gly Asn Ala Gly Asp Cys Leu Ala
            320                 325                 330

AAC CCA GCT GTG CCC TGG GGA CAA GGG GTC GAA ATA GAA AGG GCC CTC    1359
Asn Pro Ala Val Pro Trp Gly Gln Gly Val Glu Ile Glu Arg Ala Leu
            335                 340                 345

AAG CAG GTT CAA GTT GAA GGC CTC TCT GGA AAT ATA AAG TTT GAC CAG    1407
Lys Gln Val Gln Val Glu Gly Leu Ser Gly Asn Ile Lys Phe Asp Gln
350                 355                 360

AAT GGA AAA CGA ATA AAC TAC ACA ATT AAC ATC ATG GAG CTC AAA ACA    1455
Asn Gly Lys Arg Ile Asn Tyr Thr Ile Asn Ile Met Glu Leu Lys Thr
365                 370                 375                 380

AAT GGA CCC CGG AAG ATT GGG TAC TGG AGT GAA GTG GAT AAA ATG GTT    1503
Asn Gly Pro Arg Lys Ile Gly Tyr Trp Ser Glu Val Asp Lys Met Val
            385                 390                 395

GTC ACC CTA ACT GAG CTC CCA TCA GGA AAT GAC ACG TCT GGG CTT GAA    1551
Val Thr Leu Thr Glu Leu Pro Ser Gly Asn Asp Thr Ser Gly Leu Glu
            400                 405                 410

AAC AAA ACT GTG GTG GTC ACC ACA ATA TTG GAA TCT CCA TAT GTT ATG    1599
Asn Lys Thr Val Val Val Thr Thr Ile Leu Glu Ser Pro Tyr Val Met
            415                 420                 425

ATG AAG AAA AAT CAT GAA ATG CTT GAA GGG AAT GAG CGT TAC GAG GGC    1647
Met Lys Lys Asn His Glu Met Leu Glu Gly Asn Glu Arg Tyr Glu Gly
            430                 435                 440

TAC TGT GTT GAC TTA GCT GCA GAA ATT GCC AAA CAC TGT GGG TTC AAG    1695
Tyr Cys Val Asp Leu Ala Ala Glu Ile Ala Lys His Cys Gly Phe Lys
445                 450                 455                 460

TAC AAG CTG ACT ATT GTT GGG GAT GGC AAG TAT GGG GCC AGG GAT GCC    1743
Tyr Lys Leu Thr Ile Val Gly Asp Gly Lys Tyr Gly Ala Arg Asp Ala
            465                 470                 475

GAC ACC AAA ATT TGG AAT GGT ATG GTT GGA GAG CTT GTC TAC GGG AAA    1791
Asp Thr Lys Ile Trp Asn Gly Met Val Gly Glu Leu Val Tyr Gly Lys
            480                 485                 490

GCT GAC ATT GCA ATT GCT CCA TTA ACT ATC ACT CTC GTG AGA GAA GAG    1839
Ala Asp Ile Ala Ile Ala Pro Leu Thr Ile Thr Leu Val Arg Glu Glu
            495                 500                 505

GTG ATT GAC TTC TCC AAG CCC TTC ATG AGT CTT GGA ATC TCT ATC ATG    1887
Val Ile Asp Phe Ser Lys Pro Phe Met Ser Leu Gly Ile Ser Ile Met
510                 515                 520

ATC AAG AAG CCT CAG AAG TCC AAA CCA GGA GTG TTT TCC TTT CTT GAT    1935
Ile Lys Lys Pro Gln Lys Ser Lys Pro Gly Val Phe Ser Phe Leu Asp
525                 530                 535                 540

CCT TTA GCC TAT GAG ATC TGG ATG TGC ATT GTG TTT GCC TAC ATT GGG    1983
Pro Leu Ala Tyr Glu Ile Trp Met Cys Ile Val Phe Ala Tyr Ile Gly
            545                 550                 555

GTC AGT GTA GTT TTA TTC CTG GTC AGC AGA TTT AGC CCC TAC GAG TGG    2031
Val Ser Val Val Leu Phe Leu Val Ser Arg Phe Ser Pro Tyr Glu Trp
            560                 565                 570

CAC ACT GAG GAA TTT GAA GAT GGA AGA GAA ACA CAA AGT AGT GAA TCA    2079
His Thr Glu Glu Phe Glu Asp Gly Arg Glu Thr Gln Ser Ser Glu Ser
            575                 580                 585

ACT AAT GAA TTT GGG ATT TTT AAT AGT CTC TGG TTT TCC TTG GGT GCC    2127
Thr Asn Glu Phe Gly Ile Phe Asn Ser Leu Trp Phe Ser Leu Gly Ala
            590                 595                 600

TTT ATG CGG CAG GGA TGC GAT ATT TCG CCA AGA TCC CTC TCT GGG CGC    2175
Phe Met Arg Gln Gly Cys Asp Ile Ser Pro Arg Ser Leu Ser Gly Arg
605                 610                 615                 620

ATT GTT GGA GGT GTG TGG TGG TTC TTT ACC CTG ATC ATA TCC TCC        2223
Ile Val Gly Gly Val Trp Trp Phe Phe Thr Leu Ile Ile Ile Ser Ser
            625                 630                 635
```

```
TAC ACG GCT AAC TTA GCT GCC TTC CTG ACT GTA GAG AGG ATG GTG TCT    2271
Tyr Thr Ala Asn Leu Ala Ala Phe Leu Thr Val Glu Arg Met Val Ser
            640                 645                 650

CCC ATC GAA AGT GCT GAG GAT CTG TCT AAG CAA ACA GAA ATT GCT TAT    2319
Pro Ile Glu Ser Ala Glu Asp Leu Ser Lys Gln Thr Glu Ile Ala Tyr
            655                 660                 665

GGA ACA TTA GAC TCT GGC TCC ACT AAA GAG TTT TTC AGG AGA TCT AAA    2367
Gly Thr Leu Asp Ser Gly Ser Thr Lys Glu Phe Phe Arg Arg Ser Lys
            670                 675                 680

ATC GCA GTG TTT GAT AAA ATG TGG ACT TAT ATG AGG AGT GCA GAG CCC    2415
Ile Ala Val Phe Asp Lys Met Trp Thr Tyr Met Arg Ser Ala Glu Pro
685                 690                 695                 700

TCT GTG TTT GTG AGG ACT ACC GCA GAA GGA GTA GCC AGA GTC CGG AAA    2463
Ser Val Phe Val Arg Thr Thr Ala Glu Gly Val Ala Arg Val Arg Lys
                705                 710                 715

TCC AAA GGA AAG TAT GCC TAC TTG CTG GAG TCC ACA ATG AAC GAG TAC    2511
Ser Lys Gly Lys Tyr Ala Tyr Leu Leu Glu Ser Thr Met Asn Glu Tyr
                720                 725                 730

ATC GAG CAG AGG AAG CCT TGT GAC ACC ATG AAA GTG GGA GGA AAC TTG    2559
Ile Glu Gln Arg Lys Pro Cys Asp Thr Met Lys Val Gly Gly Asn Leu
                735                 740                 745

GAT TCC AAA GGC TAC GGC ATC GCC ACA CCT AAA GGA TCC TCA TTA GGA    2607
Asp Ser Lys Gly Tyr Gly Ile Ala Thr Pro Lys Gly Ser Ser Leu Gly
            750                 755                 760

AAT GCG GTT AAC CTC GCA GTA CTA AAA CTG AAT GAA CAA GGC CTG TTG    2655
Asn Ala Val Asn Leu Ala Val Leu Lys Leu Asn Glu Gln Gly Leu Leu
765                 770                 775                 780

GAC AAA TTG AAA AAC AAA TGG TGG TAC GAC AAA GGA GAG TGC GGC AGC    2703
Asp Lys Leu Lys Asn Lys Trp Trp Tyr Asp Lys Gly Glu Cys Gly Ser
                785                 790                 795

GGG GGA GGT GAT TCC AAG GAA AAG ACC AGT GCC CTC AGT CTG AGC AAC    2751
Gly Gly Gly Asp Ser Lys Glu Lys Thr Ser Ala Leu Ser Leu Ser Asn
                800                 805                 810

GTT GCT GGA GTA TTC TAC ATC CTT GTC GGG GGC CTT GGT TTG GCA ATG    2799
Val Ala Gly Val Phe Tyr Ile Leu Val Gly Gly Leu Gly Leu Ala Met
            815                 820                 825

CTG GTG GCT TTG ATT GAG TTC TGT TAC AAG TCA AGG GCC GAG GCG AAA    2847
Leu Val Ala Leu Ile Glu Phe Cys Tyr Lys Ser Arg Ala Glu Ala Lys
            830                 835                 840

CGA ATG AAG GTG GCA AAG AAT CCA CAG AAT ATT AAC CCA TCT TCC TCG    2895
Arg Met Lys Val Ala Lys Asn Pro Gln Asn Ile Asn Pro Ser Ser Ser
845                 850                 855                 860

CAG AAT TCC CAG AAT TTT GCA ACT TAT AAG GAA GGT TAC AAC GTA TAT    2943
Gln Asn Ser Gln Asn Phe Ala Thr Tyr Lys Glu Gly Tyr Asn Val Tyr
                865                 870                 875

GGC ATC GAG AGT GTT AAA ATT TAGGGGATGA CCTTGAGTGA TGTCATGAGG AGCA  2998
Gly Ile Glu Ser Val Lys Ile
            880

AGGCAAGGCT GTCAATTACA GGAAGTACTG GAGAAAATGG ACGTGTTATG ACTCCAGAAT 3058

TTCCCAAAGC AGTGCATGCT GTCCCTTACG TGAGTCCTGG CATGGGAATG AATGTCAGTG 3118

TGACTGATCT CTCGTGATTG ATAGGAACCT TCTGAGTGCC TTACACAATG GTTTCCTTGT 3178

GTGTTTATTG TCAAAGTGGT GAGAGGCATC CGATATCTTG AAGGCTTTTC TTTCAGCCAA 3238

GAATTCTTAA CTATGTGGAG TTCACCTTGA ATTGTAAGGA AAGATAAATT ACAAACAGAG 3298

CATCATTTTC TACTCCGATA TCAGAGGAAG CGTGGTGGAC ATGCACAGCT AACATGGAAA 3358

TACTATCATT TAACTGAAGT CTTTGTACAG ACAACAAACC CGTTTCCGCA GCCACTATTG 3418

TTAGTCTCTT GATTCATAAT GACTTAAGCA CACTTGACAT CAACTGCATC AAGATGTGAC 3478
```

-continued

CTGTTTTATA AAAAAAAAAA AAAAAAA                                                                       3505

(2) INFORMATION FOR SEQ ID NO:4:

(i) SEQUENCE CHARACTERISTICS:
        (A) LENGTH: 883 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Gln Lys Ile Met His Ile Ser Val Leu Leu Ser Pro Val Leu Trp
  1               5                  10                  15

Gly Leu Ile Phe Gly Val Ser Ser Asn Ser Ile Gln Ile Gly Gly Leu
             20                  25                  30

Phe Pro Arg Gly Ala Asp Gln Glu Tyr Ser Ala Phe Arg Val Gly Met
         35                  40                  45

Val Gln Phe Ser Thr Ser Glu Phe Arg Leu Thr Pro His Ile Asp Asn
     50                  55                  60

Leu Glu Val Ala Asn Ser Phe Ala Val Thr Asn Ala Phe Cys Ser Gln
 65                  70                  75                  80

Phe Ser Arg Gly Val Tyr Ala Ile Phe Gly Phe Tyr Asp Lys Lys Ser
                 85                  90                  95

Val Asn Thr Ile Thr Ser Phe Cys Gly Thr Leu His Val Ser Phe Ile
            100                 105                 110

Thr Pro Ser Phe Pro Thr Asp Gly Thr His Pro Phe Val Ile Gln Met
        115                 120                 125

Arg Pro Asp Leu Lys Gly Ala Leu Leu Ser Leu Ile Glu Tyr Tyr Gln
130                 135                 140

Trp Asp Lys Phe Ala Tyr Leu Tyr Asp Ser Asp Arg Gly Leu Ser Thr
145                 150                 155                 160

Leu Gln Ala Val Leu Asp Ser Ala Ala Glu Lys Lys Trp Gln Val Thr
                165                 170                 175

Ala Ile Asn Val Gly Asn Ile Asn Asn Asp Lys Lys Asp Glu Thr Tyr
            180                 185                 190

Arg Ser Leu Phe Gln Asp Leu Glu Leu Lys Lys Glu Arg Arg Val Ile
        195                 200                 205

Leu Asp Cys Glu Arg Asp Lys Val Asn Asp Ile Val Asp Gln Val Ile
    210                 215                 220

Thr Ile Gly Lys His Val Lys Gly Tyr His Tyr Ile Ile Ala Asn Leu
225                 230                 235                 240

Gly Phe Thr Asp Gly Asp Leu Leu Lys Ile Gln Phe Gly Gly Ala Asn
                245                 250                 255

Val Ser Gly Phe Gln Ile Val Asp Tyr Asp Asp Ser Leu Val Ser Lys
            260                 265                 270

Phe Ile Glu Arg Trp Ser Thr Leu Glu Glu Lys Glu Tyr Pro Gly Ala
        275                 280                 285

His Thr Ala Thr Ile Lys Tyr Thr Ser Ala Leu Thr Tyr Asp Ala Val
    290                 295                 300

Gln Val Met Thr Glu Ala Phe Arg Asn Leu Arg Lys Gln Arg Ile Glu
305                 310                 315                 320

Ile Ser Arg Arg Gly Asn Ala Gly Asp Cys Leu Ala Asn Pro Ala Val
                325                 330                 335

Pro Trp Gly Gln Gly Val Glu Ile Glu Arg Ala Leu Lys Gln Val Gln
```

-continued

```
                340                 345                 350
Val Glu Gly Leu Ser Gly Asn Ile Lys Phe Asp Gln Asn Gly Lys Arg
            355                 360                 365
Ile Asn Tyr Thr Ile Asn Ile Met Glu Leu Lys Thr Asn Gly Pro Arg
370                 375                 380
Lys Ile Gly Tyr Trp Ser Glu Val Asp Lys Met Val Val Thr Leu Thr
385                 390                 395                 400
Glu Leu Pro Ser Gly Asn Asp Thr Ser Gly Leu Glu Asn Lys Thr Val
                405                 410                 415
Val Val Thr Thr Ile Leu Glu Ser Pro Tyr Val Met Met Lys Lys Asn
            420                 425                 430
His Glu Met Leu Glu Gly Asn Glu Arg Tyr Glu Gly Tyr Cys Val Asp
        435                 440                 445
Leu Ala Ala Glu Ile Ala Lys His Cys Gly Phe Lys Tyr Lys Leu Thr
    450                 455                 460
Ile Val Gly Asp Gly Lys Tyr Gly Ala Arg Asp Ala Asp Thr Lys Ile
465                 470                 475                 480
Trp Asn Gly Met Val Gly Glu Leu Val Tyr Gly Lys Ala Asp Ile Ala
                485                 490                 495
Ile Ala Pro Leu Thr Ile Thr Leu Val Arg Glu Glu Val Ile Asp Phe
            500                 505                 510
Ser Lys Pro Phe Met Ser Leu Gly Ile Ser Ile Met Ile Lys Lys Pro
        515                 520                 525
Gln Lys Ser Lys Pro Gly Val Phe Ser Phe Leu Asp Pro Leu Ala Tyr
    530                 535                 540
Glu Ile Trp Met Cys Ile Val Phe Ala Tyr Ile Gly Val Ser Val Val
545                 550                 555                 560
Leu Phe Leu Val Ser Arg Phe Ser Pro Tyr Glu Trp His Thr Glu Glu
                565                 570                 575
Phe Glu Asp Gly Arg Glu Thr Gln Ser Ser Glu Ser Thr Asn Glu Phe
            580                 585                 590
Gly Ile Phe Asn Ser Leu Trp Phe Ser Leu Gly Ala Phe Met Arg Gln
        595                 600                 605
Gly Cys Asp Ile Ser Pro Arg Ser Leu Ser Gly Arg Ile Val Gly Gly
    610                 615                 620
Val Trp Trp Phe Phe Thr Leu Ile Ile Ile Ser Ser Tyr Thr Ala Asn
625                 630                 635                 640
Leu Ala Ala Phe Leu Thr Val Glu Arg Met Val Ser Pro Ile Glu Ser
                645                 650                 655
Ala Glu Asp Leu Ser Lys Gln Thr Glu Ile Ala Tyr Gly Thr Leu Asp
            660                 665                 670
Ser Gly Ser Thr Lys Glu Phe Phe Arg Arg Ser Lys Ile Ala Val Phe
        675                 680                 685
Asp Lys Met Trp Thr Tyr Met Arg Ser Ala Glu Pro Ser Val Phe Val
    690                 695                 700
Arg Thr Thr Ala Glu Gly Val Ala Arg Val Arg Lys Ser Lys Gly Lys
705                 710                 715                 720
Tyr Ala Tyr Leu Leu Glu Ser Thr Met Asn Glu Tyr Ile Glu Gln Arg
                725                 730                 735
Lys Pro Cys Asp Thr Met Lys Val Gly Gly Asn Leu Asp Ser Lys Gly
            740                 745                 750
Tyr Gly Ile Ala Thr Pro Lys Gly Ser Ser Leu Gly Asn Ala Val Asn
        755                 760                 765
```

-continued

```
Leu Ala Val Leu Lys Leu Asn Glu Gln Gly Leu Leu Asp Lys Leu Lys
    770                 775                 780

Asn Lys Trp Trp Tyr Asp Lys Gly Glu Cys Gly Ser Gly Gly Gly Asp
785                 790                 795                 800

Ser Lys Glu Lys Thr Ser Ala Leu Ser Ser Asn Val Ala Gly Val
                805                 810                 815

Phe Tyr Ile Leu Val Gly Gly Leu Gly Leu Ala Met Leu Val Ala Leu
            820                 825                 830

Ile Glu Phe Cys Tyr Lys Ser Arg Ala Glu Ala Lys Arg Met Lys Val
            835                 840                 845

Ala Lys Asn Pro Gln Asn Ile Asn Pro Ser Ser Ser Gln Asn Ser Gln
    850                 855                 860

Asn Phe Ala Thr Tyr Lys Glu Gly Tyr Asn Val Tyr Gly Ile Glu Ser
865                 870                 875                 880

Val Lys Ile
```

(2) INFORMATION FOR SEQ ID NO:5:

(i) SEQUENCE CHARACTERISTICS:
        (A) LENGTH: 3083 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: GluR3

(ix) FEATURE:
        (A) NAME/KEY: Coding Sequence
        (B) LOCATION: 167...2830
        (D) OTHER INFORMATION:

(xi) SEQUENCE DESCRIPTION: SEQ ID NO:5:

```
GCTCTCTCTC TCTCTCTCTC TCTCTCTCTC TCTCTCTCTC TCTCTCTCTC TTCTCTCAGA      60

AATCGCTTTG GGAACCCAG CTTGCAGCCA ATGAACCCGC CTTCCAGATT GGTGTGAAGA      120

CAGAAGTGAG CTTCGTTTTA GGCGTCAAGC AGCCAGGCAG AAGAAA ATG GGG CAA        175
                                                 Met Gly Gln
                                                  1

AGC GTG CTC CGG GCG GTC TTT TTA GTC CTG GGG CTT TTG GGT CAT          223
Ser Val Leu Arg Ala Val Phe Phe Leu Val Leu Gly Leu Leu Gly His
    5                   10                  15

TCT CAC GGA GGA TTC CCC AAC ACC ATC AGC ATA GGT GGA CTT TTC ATG      271
Ser His Gly Gly Phe Pro Asn Thr Ile Ser Ile Gly Gly Leu Phe Met
20          25                  30                  35

AGA AAC ACG GTT CAG GAG CAC AGC GCT TTC CGC TTT GCT GTG CAG TTA      319
Arg Asn Thr Val Gln Glu His Ser Ala Phe Arg Phe Ala Val Gln Leu
                40                  45                  50

TAC AAC ACC AAC CAG AAC ACC ACT GAG AAG CCC TTC CAT TTG AAT TAC      367
Tyr Asn Thr Asn Gln Asn Thr Thr Glu Lys Pro Phe His Leu Asn Tyr
            55                  60                  65

CAC GTA GAC CAC TTG GAT TCC TCC AAT AGT TTT TCT GTG ACT AAT GCT      415
His Val Asp His Leu Asp Ser Ser Asn Ser Phe Ser Val Thr Asn Ala
        70                  75                  80

TTC TGC TCC CAG TTC TCC AGA GGG GTG TAT GCT ATC TTT GGA TTC TAT      463
Phe Cys Ser Gln Phe Ser Arg Gly Val Tyr Ala Ile Phe Gly Phe Tyr
    85                  90                  95

GAC CAG ATG TCA ATG AAC ACC CTG ACC TCC TTC TGT GGG GCC CTG CAC      511
Asp Gln Met Ser Met Asn Thr Leu Thr Ser Phe Cys Gly Ala Leu His
100                 105                 110                 115
```

```
ACA TCT TTT GTC ACA CCT AGC TTT CCC ACT GAT GCA GAT GTG CAG TTT      559
Thr Ser Phe Val Thr Pro Ser Phe Pro Thr Asp Ala Asp Val Gln Phe
            120                 125                 130

GTC ATC CAG ATG CGC CCA GCC TTG AAG GGT GCC ATT CTG AGT CTT CTC      607
Val Ile Gln Met Arg Pro Ala Leu Lys Gly Ala Ile Leu Ser Leu Leu
        135                 140                 145

AGT TAC TAC AAG TGG GAG AAG TTT GTG TAC CTC TAT GAC ACA GAA CGA      655
Ser Tyr Tyr Lys Trp Glu Lys Phe Val Tyr Leu Tyr Asp Thr Glu Arg
            150                 155                 160

GGG TTT TCT GTC CTA CAA GCA ATT ATG GAG GCA GCA GTG CAA AAC AAC      703
Gly Phe Ser Val Leu Gln Ala Ile Met Glu Ala Ala Val Gln Asn Asn
        165                 170                 175

TGG CAA GTG ACA GCA AGG TCT GTG GGA AAC ATA AAG GAC GTC CAG GAA      751
Trp Gln Val Thr Ala Arg Ser Val Gly Asn Ile Lys Asp Val Gln Glu
180                 185                 190                 195

TTC AGA CGC ATC ATT GAA GAA ATG GAC AGA AGG CAG GAA AAA CGA TAC      799
Phe Arg Arg Ile Ile Glu Glu Met Asp Arg Arg Gln Glu Lys Arg Tyr
                200                 205                 210

TTG ATT GAC TGT GAA GTC GAA AGG ATT AAC ACA ATT TTG GAA CAG GTT      847
Leu Ile Asp Cys Glu Val Glu Arg Ile Asn Thr Ile Leu Glu Gln Val
            215                 220                 225

GTG ATC CTG GGG AAG CAT TCA AGA GGC TAT CAC TAC ATG CTT GCT AAC      895
Val Ile Leu Gly Lys His Ser Arg Gly Tyr His Tyr Met Leu Ala Asn
        230                 235                 240

CTG GGT TTT ACT GAC ATT TTA CTG GAA AGA GTC ATG CAT GGG GGA GCC      943
Leu Gly Phe Thr Asp Ile Leu Leu Glu Arg Val Met His Gly Gly Ala
245                 250                 255

AAC ATT ACA GGT TTC CAG ATT GTC AAC AAT GAA AAC CCA ATG GTT CAG      991
Asn Ile Thr Gly Phe Gln Ile Val Asn Asn Glu Asn Pro Met Val Gln
260                 265                 270                 275

CAG TTC ATA CAG CGC TGG GTG AGA CTG GAT GAA AGG GAA TTC CCT GAA     1039
Gln Phe Ile Gln Arg Trp Val Arg Leu Asp Glu Arg Glu Phe Pro Glu
                280                 285                 290

GCC AAG AAT GCA CCA CTG AAG TAT ACA TCT GCG CTG ACA CAT GAC GCA     1087
Ala Lys Asn Ala Pro Leu Lys Tyr Thr Ser Ala Leu Thr His Asp Ala
            295                 300                 305

ATA TTG GTC ATA GCA GAA GCC TTC CGA TAC CTG AGG AGA CAG AGA GTG     1135
Ile Leu Val Ile Ala Glu Ala Phe Arg Tyr Leu Arg Arg Gln Arg Val
        310                 315                 320

GAT GTC TCC CGC AGA GGC AGT GCT GGA GAC TGC TTA GCA AAT CCT GCT     1183
Asp Val Ser Arg Arg Gly Ser Ala Gly Asp Cys Leu Ala Asn Pro Ala
325                 330                 335

GTG CCC TGG AGT CAA GGA ATT GAT ATT GAG AGA GCT CTG AAA ATG GTG     1231
Val Pro Trp Ser Gln Gly Ile Asp Ile Glu Arg Ala Leu Lys Met Val
340                 345                 350                 355

CAA GTA CAA GGA ATG ACT GGA AAC ATC CAA TTT GAC ACT TAT GGA CGT     1279
Gln Val Gln Gly Met Thr Gly Asn Ile Gln Phe Asp Thr Tyr Gly Arg
                360                 365                 370

AGG ACA AAT TAT ACC ATT GAT GTC TAT GAA ATG AAA GTC TCG GGT TCT     1327
Arg Thr Asn Tyr Thr Ile Asp Val Tyr Glu Met Lys Val Ser Gly Ser
            375                 380                 385

CGA AAA GCT GGT TAC TGG AAC GAA TAT GAA AGG TTT GTG CCC TTC TCA     1375
Arg Lys Ala Gly Tyr Trp Asn Glu Tyr Glu Arg Phe Val Pro Phe Ser
        390                 395                 400

GAT CAA CAA ATC AGC AAT GAC AGC TCA TCC TCA GAG AAC CGG ACC ATT     1423
Asp Gln Gln Ile Ser Asn Asp Ser Ser Ser Ser Glu Asn Arg Thr Ile
405                 410                 415

GTA GTG ACT ACC ATT CTG GAA TCA CCA TAT GTG ATG TAT AAA AAG AAT     1471
Val Val Thr Thr Ile Leu Glu Ser Pro Tyr Val Met Tyr Lys Lys Asn
420                 425                 430                 435
```

```
CAT GAG CAG CTG GAA GGA AAT GAG CGC TAT GAA GGC TAC TGT GTT GAT    1519
His Glu Gln Leu Glu Gly Asn Glu Arg Tyr Glu Gly Tyr Cys Val Asp
            440                 445                 450

TTA GCC TAT GAA ATA GCC AAA CAC GTA AGG ATC AAA TAC AAA TTG TCC    1567
Leu Ala Tyr Glu Ile Ala Lys His Val Arg Ile Lys Tyr Lys Leu Ser
        455                 460                 465

ATT GTC GGT GAT GGG AAA TAT GGC GCC AGA GAT CCA GAG ACT AAA ATA    1615
Ile Val Gly Asp Gly Lys Tyr Gly Ala Arg Asp Pro Glu Thr Lys Ile
        470                 475                 480

TGG AAT GGC ATG GTT GGG GAA CTT GTC TAT GGA AGA GCT GAT ATA GCT    1663
Trp Asn Gly Met Val Gly Glu Leu Val Tyr Gly Arg Ala Asp Ile Ala
    485                 490                 495

GTT GCT CCA CTC ACT ATA ACA TTG GTC CGT GAA GAA GTC ATA GAT TTC    1711
Val Ala Pro Leu Thr Ile Thr Leu Val Arg Glu Glu Val Ile Asp Phe
500                 505                 510                 515

TCA AAC GCA TTT ATG AGC CTG GGA ATC TCC ATC ATG ATA AAG AAG CCT    1759
Ser Asn Ala Phe Met Ser Leu Gly Ile Ser Ile Met Ile Lys Lys Pro
                520                 525                 530

CAG AAA TCA AAG CCA GGC GTC TTT TCA TTC CTG GAT CCT TTG GCT TAT    1807
Gln Lys Ser Lys Pro Gly Val Phe Ser Phe Leu Asp Pro Leu Ala Tyr
            535                 540                 545

GAA ATC TGG ATG TGC ATT GTC TTC GCT TAC ATT GGA GTC AGT GTA GTT    1855
Glu Ile Trp Met Cys Ile Val Phe Ala Tyr Ile Gly Val Ser Val Val
        550                 555                 560

CTC TTC CTA GTC AGC AGA TTT AGC CCT TAT GAA TGG CAC TTG GAA GAC    1903
Leu Phe Leu Val Ser Arg Phe Ser Pro Tyr Glu Trp His Leu Glu Asp
565                 570                 575

AAC AAT GAA GAA CCT CGT GAC CCA CAA AGC CCT CCT GAT CCT CCC AAT    1951
Asn Asn Glu Glu Pro Arg Asp Pro Gln Ser Pro Pro Asp Pro Pro Asn
580                 585                 590                 595

GAA TTT GGA ATA TTT AAC AGT CTT TGG TTT TCC TTG GGT GCT TTC ATG    1999
Glu Phe Gly Ile Phe Asn Ser Leu Trp Phe Ser Leu Gly Ala Phe Met
                600                 605                 610

CAG CAA GGA TGT GAT ATT TCT CCA AGA TCA CTT TCT GGG CGC ATT GTT    2047
Gln Gln Gly Cys Asp Ile Ser Pro Arg Ser Leu Ser Gly Arg Ile Val
            615                 620                 625

GGA GGG GTT TGG TGG TTC TTC ACC CTG ATC ATA ATC TCT TCC TAC ACT    2095
Gly Gly Val Trp Trp Phe Phe Thr Leu Ile Ile Ile Ser Ser Tyr Thr
        630                 635                 640

GCA AAC CTT GCT GCT TTC CTG ACT GTG GAG AGG ATG GTG TCC CCT ATA    2143
Ala Asn Leu Ala Ala Phe Leu Thr Val Glu Arg Met Val Ser Pro Ile
645                 650                 655

GAG AGC GCT GAA GAC TTA GCC AAG CAG ACT GAA ATT GCA TAT GGG ACC    2191
Glu Ser Ala Glu Asp Leu Ala Lys Gln Thr Glu Ile Ala Tyr Gly Thr
660                 665                 670                 675

CTG GAC TCT GGT TCA ACA AAA GAA TTT TTC AGA CGA TCC AAA ATT GCT    2239
Leu Asp Ser Gly Ser Thr Lys Glu Phe Phe Arg Arg Ser Lys Ile Ala
                680                 685                 690

GTG TAT GAG AAA ATG TGG TCT TAC ATG AAA TCC GCA GAG CCA TCT GTG    2287
Val Tyr Glu Lys Met Trp Ser Tyr Met Lys Ser Ala Glu Pro Ser Val
            695                 700                 705

TTT ACC AAA ACA ACA GCT GAC GGG GTA GCC CGA GTT CGG AAG TCC AAG    2335
Phe Thr Lys Thr Thr Ala Asp Gly Val Ala Arg Val Arg Lys Ser Lys
        710                 715                 720

GGA AAG TTC GCC TTC CTG CTG GAG TCG ACC ATG AAC GAG TAC ATT GAG    2383
Gly Lys Phe Ala Phe Leu Leu Glu Ser Thr Met Asn Glu Tyr Ile Glu
    725                 730                 735

CAG AGA AAG CCG TGC GAT ACG ATG AAA GTT GGT GGA AAT CTG GAT TCC    2431
Gln Arg Lys Pro Cys Asp Thr Met Lys Val Gly Gly Asn Leu Asp Ser
740                 745                 750                 755
```

```
AAA GGC TAT GGT GTG GCA ACC CCT AAA GGC TCA GCA TTA GGA AAT GCT        2479
Lys Gly Tyr Gly Val Ala Thr Pro Lys Gly Ser Ala Leu Gly Asn Ala
            760                 765                 770

GTT AAC CTG GCA GTA TTA AAA CTG AAT GAG CAA GGC CTC TTG GAC AAA        2527
Val Asn Leu Ala Val Leu Lys Leu Asn Glu Gln Gly Leu Leu Asp Lys
        775                 780                 785

TTG AAA AAC AAA TGG TGG TAC GAC AAA GGA GAG TGC GGC AGC GGG GGC        2575
Leu Lys Asn Lys Trp Trp Tyr Asp Lys Gly Glu Cys Gly Ser Gly Gly
        790                 795                 800

GGT GAC TCC AAG GAC AAG ACC AGT GCT CTA AGC CTG AGC AAT GTG GCA        2623
Gly Asp Ser Lys Asp Lys Thr Ser Ala Leu Ser Leu Ser Asn Val Ala
        805                 810                 815

GGC GTG TTC TAT ATA CTT GTC GGA GGT CTG GGC CTG GCC ATG ATG GTG        2671
Gly Val Phe Tyr Ile Leu Val Gly Gly Leu Gly Leu Ala Met Met Val
820                 825                 830                 835

GCT TTG ATA GAA TTC TGT TAC AAA TCA CGG GCA GAG TCC AAA CGC ATG        2719
Ala Leu Ile Glu Phe Cys Tyr Lys Ser Arg Ala Glu Ser Lys Arg Met
                840                 845                 850

AAA CTC ACA AAG AAC ACC CAA AAC TTT AAG CCT GCT CCT GCC ACC AAC        2767
Lys Leu Thr Lys Asn Thr Gln Asn Phe Lys Pro Ala Pro Ala Thr Asn
            855                 860                 865

ACT CAG AAT TAC GCT ACA TAC AGA GAA GGC TAC AAC GTG TAT GGA ACA        2815
Thr Gln Asn Tyr Ala Thr Tyr Arg Glu Gly Tyr Asn Val Tyr Gly Thr
        870                 875                 880

GAA AGT GTT AAG ATC TAGGGATCCC TTCCCACCAG AAGCATGCAA TGAGAGGAAA T      2871
Glu Ser Val Lys Ile
        885

CACTGAAAAC GTGGCTGCTT CAAGGATCCT GAGCCGGATT TCACTCTCCC TGGTGTCGGG      2931

CATGACACGA ATATTGCTGA TGGTGCAATG ACCTTTCAAT AGGAAAAACT GATTTTTTTT      2991

TTCCTTCAGT GCCTTATGGA ACACTCTGAG ACTTGCGACA ATGCAAACCA TCATTGAAAT      3051

CTTTTTGCTT TGCTTGAAAA AAAAAAAAA AA                                    3083
```

(2) INFORMATION FOR SEQ ID NO:6:

(i) SEQUENCE CHARACTERISTICS:
        (A) LENGTH: 888 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Gly Gln Ser Val Leu Arg Ala Val Phe Phe Leu Val Leu Gly Leu
1               5                   10                  15

Leu Gly His Ser His Gly Gly Phe Pro Asn Thr Ile Ser Ile Gly Gly
                20                  25                  30

Leu Phe Met Arg Asn Thr Val Gln Glu His Ser Ala Phe Arg Phe Ala
            35                  40                  45

Val Gln Leu Tyr Asn Thr Asn Gln Asn Thr Thr Glu Lys Pro Phe His
        50                  55                  60

Leu Asn Tyr His Val Asp His Leu Asp Ser Ser Asn Ser Phe Ser Val
65                  70                  75                  80

Thr Asn Ala Phe Cys Ser Gln Phe Ser Arg Gly Val Tyr Ala Ile Phe
                85                  90                  95

Gly Phe Tyr Asp Gln Met Ser Met Asn Thr Leu Thr Ser Phe Cys Gly
            100                 105                 110

Ala Leu His Thr Ser Phe Val Thr Pro Ser Phe Pro Thr Asp Ala Asp
        115                 120                 125
```

Val Gln Phe Val Ile Gln Met Arg Pro Ala Leu Lys Gly Ala Ile Leu
    130                 135                 140

Ser Leu Leu Ser Tyr Tyr Lys Trp Glu Lys Phe Val Tyr Leu Tyr Asp
145                 150                 155                 160

Thr Glu Arg Gly Phe Ser Val Leu Gln Ala Ile Met Glu Ala Ala Val
                165                 170                 175

Gln Asn Asn Trp Gln Val Thr Ala Arg Ser Val Gly Asn Ile Lys Asp
            180                 185                 190

Val Gln Glu Phe Arg Arg Ile Ile Glu Glu Met Asp Arg Arg Gln Glu
        195                 200                 205

Lys Arg Tyr Leu Ile Asp Cys Glu Val Glu Arg Ile Asn Thr Ile Leu
210                 215                 220

Glu Gln Val Val Ile Leu Gly Lys His Ser Arg Gly Tyr His Tyr Met
225                 230                 235                 240

Leu Ala Asn Leu Gly Phe Thr Asp Ile Leu Leu Glu Arg Val Met His
                245                 250                 255

Gly Gly Ala Asn Ile Thr Gly Phe Gln Ile Val Asn Asn Glu Asn Pro
            260                 265                 270

Met Val Gln Gln Phe Ile Gln Arg Trp Val Arg Leu Asp Glu Arg Glu
        275                 280                 285

Phe Pro Glu Ala Lys Asn Ala Pro Leu Lys Tyr Thr Ser Ala Leu Thr
290                 295                 300

His Asp Ala Ile Leu Val Ile Ala Glu Ala Phe Arg Tyr Leu Arg Arg
305                 310                 315                 320

Gln Arg Val Asp Val Ser Arg Arg Gly Ser Ala Gly Asp Cys Leu Ala
                325                 330                 335

Asn Pro Ala Val Pro Trp Ser Gln Gly Ile Asp Ile Glu Arg Ala Leu
            340                 345                 350

Lys Met Val Gln Val Gln Gly Met Thr Gly Asn Ile Gln Phe Asp Thr
        355                 360                 365

Tyr Gly Arg Arg Thr Asn Tyr Thr Ile Asp Val Tyr Glu Met Lys Val
370                 375                 380

Ser Gly Ser Arg Lys Ala Gly Tyr Trp Asn Glu Tyr Glu Arg Phe Val
385                 390                 395                 400

Pro Phe Ser Asp Gln Gln Ile Ser Asn Asp Ser Ser Ser Ser Glu Asn
                405                 410                 415

Arg Thr Ile Val Val Thr Thr Ile Leu Glu Ser Pro Tyr Val Met Tyr
            420                 425                 430

Lys Lys Asn His Glu Gln Leu Glu Gly Asn Glu Arg Tyr Glu Gly Tyr
        435                 440                 445

Cys Val Asp Leu Ala Tyr Glu Ile Ala Lys His Val Arg Ile Lys Tyr
450                 455                 460

Lys Leu Ser Ile Val Gly Asp Gly Lys Tyr Gly Ala Arg Asp Pro Glu
465                 470                 475                 480

Thr Lys Ile Trp Asn Gly Met Val Gly Glu Leu Val Tyr Gly Arg Ala
                485                 490                 495

Asp Ile Ala Val Ala Pro Leu Thr Ile Thr Leu Val Arg Glu Glu Val
            500                 505                 510

Ile Asp Phe Ser Asn Ala Phe Met Ser Leu Gly Ile Ser Ile Met Ile
        515                 520                 525

Lys Lys Pro Gln Lys Ser Lys Pro Gly Val Phe Ser Phe Leu Asp Pro
530                 535                 540

Leu Ala Tyr Glu Ile Trp Met Cys Ile Val Phe Ala Tyr Ile Gly Val

```
                545                 550                 555                 560
Ser Val Val Leu Phe Leu Val Ser Arg Phe Ser Pro Tyr Glu Trp His
                565                 570                 575
Leu Glu Asp Asn Asn Glu Glu Pro Arg Asp Pro Gln Ser Pro Pro Asp
                580                 585                 590
Pro Pro Asn Glu Phe Gly Ile Phe Asn Ser Leu Trp Phe Ser Leu Gly
                595                 600                 605
Ala Phe Met Gln Gln Gly Cys Asp Ile Ser Pro Arg Ser Leu Ser Gly
                610                 615                 620
Arg Ile Val Gly Gly Val Trp Trp Phe Phe Thr Leu Ile Ile Ile Ser
625                 630                 635                 640
Ser Tyr Thr Ala Asn Leu Ala Ala Phe Leu Thr Val Glu Arg Met Val
                645                 650                 655
Ser Pro Ile Glu Ser Ala Glu Asp Leu Ala Lys Gln Thr Glu Ile Ala
                660                 665                 670
Tyr Gly Thr Leu Asp Ser Gly Ser Thr Lys Glu Phe Phe Arg Arg Ser
                675                 680                 685
Lys Ile Ala Val Tyr Glu Lys Met Trp Ser Tyr Met Lys Ser Ala Glu
                690                 695                 700
Pro Ser Val Phe Thr Lys Thr Thr Ala Asp Gly Val Ala Arg Val Arg
705                 710                 715                 720
Lys Ser Lys Gly Lys Phe Ala Phe Leu Leu Glu Ser Thr Met Asn Glu
                725                 730                 735
Tyr Ile Glu Gln Arg Lys Pro Cys Asp Thr Met Lys Val Gly Gly Asn
                740                 745                 750
Leu Asp Ser Lys Gly Tyr Gly Val Ala Thr Pro Lys Gly Ser Ala Leu
                755                 760                 765
Gly Asn Ala Val Asn Leu Ala Val Leu Lys Leu Asn Glu Gln Gly Leu
                770                 775                 780
Leu Asp Lys Leu Lys Asn Lys Trp Trp Tyr Asp Lys Gly Glu Cys Gly
785                 790                 795                 800
Ser Gly Gly Gly Asp Ser Lys Asp Lys Thr Ser Ala Leu Ser Leu Ser
                805                 810                 815
Asn Val Ala Gly Val Phe Tyr Ile Leu Val Gly Gly Leu Gly Leu Ala
                820                 825                 830
Met Met Val Ala Leu Ile Glu Phe Cys Tyr Lys Ser Arg Ala Glu Ser
                835                 840                 845
Lys Arg Met Lys Leu Thr Lys Asn Thr Gln Asn Phe Lys Pro Ala Pro
850                 855                 860
Ala Thr Asn Thr Gln Asn Tyr Ala Thr Tyr Arg Glu Gly Tyr Asn Val
865                 870                 875                 880
Tyr Gly Thr Glu Ser Val Lys Ile
                885

(2) INFORMATION FOR SEQ ID NO:7:

(i) SEQUENCE CHARACTERISTICS:
         (A) LENGTH: 2971 base pairs
         (B) TYPE: nucleic acid
         (C) STRANDEDNESS: single
         (D) TOPOLOGY: linear (ii) MOLECULE TYPE: cDNA (vii) IMMEDIATE SOURCE:
         (B) CLONE: GluR4

(ix) FEATURE:
```

(A) NAME/KEY: Coding Sequence
(B) LOCATION: 162...2867
(D) OTHER INFORMATION:

(xi) SEQUENCE DESCRIPTION: SEQ ID NO:7:

```
GTAATGGAGT GTACGCAAAA TCCTCTGTCT GTGGACTCGC ACCAGAGCCT CCCAGAAAAC        60

CTGGGCGATC TGCGCCATCG TCTTCAATGC CTCTCTGAAA AGCCTTTAGC AAGACTGAGA       120

GAAAGAGAAA AGAGAGCGCG CCAGAGAGAG GAGCAAAGAA G ATG AGG ATT ATT TGC      176
                                             Met Arg Ile Ile Cys
                                              1               5

AGG CAG ATT GTC TTG TTG TTT TCT GGA TTT TGG GGA CTC GCC ATG GGA        224
Arg Gln Ile Val Leu Leu Phe Ser Gly Phe Trp Gly Leu Ala Met Gly
         10                  15                  20

GCC TTT CCA AGC AGC GTT CAA ATA GGT GGT CTC TTC ATC CGA AAC ACA        272
Ala Phe Pro Ser Ser Val Gln Ile Gly Gly Leu Phe Ile Arg Asn Thr
     25                  30                  35

GAC CAG GAA TAC ACT GCT TTT AGA CTG GCA ATC TTT CTT CAT AAC ACC        320
Asp Gln Glu Tyr Thr Ala Phe Arg Leu Ala Ile Phe Leu His Asn Thr
 40                  45                  50

AGC CCC AAT GCA TCG GAA GCT CCT TTC AAT TTG GTA CCT CAT GTG GAC        368
Ser Pro Asn Ala Ser Glu Ala Pro Phe Asn Leu Val Pro His Val Asp
55                  60                  65

AAC ATT GAG ACT GCC AAC AGT TTT GCT GTG ACA AAC GCC TTC TGT TCC        416
Asn Ile Glu Thr Ala Asn Ser Phe Ala Val Thr Asn Ala Phe Cys Ser
70                  75                  80                  85

CAG TAT TCT AGA GGG GTG TTT GCC ATT TTT GGA CTC TAT GAC AAG AGA        464
Gln Tyr Ser Arg Gly Val Phe Ala Ile Phe Gly Leu Tyr Asp Lys Arg
             90                  95                 100

TCC GTG CAT ACC TTG ACC TCG TTC TGC AGG CGT CTG CAC ATC TCT CTC        512
Ser Val His Thr Leu Thr Ser Phe Cys Arg Arg Leu His Ile Ser Leu
            105                 110                 115

ATC ACA CCA AGC TTT CCC ACT GAA GGG GAG AGC CAG TTT GTG CTG CAG        560
Ile Thr Pro Ser Phe Pro Thr Glu Gly Glu Ser Gln Phe Val Leu Gln
        120                 125                 130

CTA AGA CCT TCA CTG AGA GGT GCA CTC CTG AGC CTC CTG GAT CAC TAT        608
Leu Arg Pro Ser Leu Arg Gly Ala Leu Leu Ser Leu Leu Asp His Tyr
        135                 140                 145

GAG TGG AAC TGT TTC GTC TTC CTG TAT GAT ACA GAC AGG GGG TAT TCA        656
Glu Trp Asn Cys Phe Val Phe Leu Tyr Asp Thr Asp Arg Gly Tyr Ser
150                 155                 160                 165

ATA CTT CAA GCT ATA ATG GAA AAA GCA GGA CAA AAT GGA TGG CAT GTC        704
Ile Leu Gln Ala Ile Met Glu Lys Ala Gly Gln Asn Gly Trp His Val
                170                 175                 180

AGT GCA ATA TGT GTG GAA AAT TTT AAT GAT GTC AGC TAC AGG CAA CTG        752
Ser Ala Ile Cys Val Glu Asn Phe Asn Asp Val Ser Tyr Arg Gln Leu
            185                 190                 195

CTA GAA GAG CTT GAC AGA AGA CAA GAG AAG AAA TTT GTG ATA GAT TGT        800
Leu Glu Glu Leu Asp Arg Arg Gln Glu Lys Lys Phe Val Ile Asp Cys
        200                 205                 210

GAG ATA GAG AGG CTT CAA AAC ATT TTA GAA CAA ATT GTG AGT GTT GGG        848
Glu Ile Glu Arg Leu Gln Asn Ile Leu Glu Gln Ile Val Ser Val Gly
        215                 220                 225

AAG CAT GTC AAA GGC TAC CAT TAT ATC ATC GCA AAT TTG GGT TTC AAG        896
Lys His Val Lys Gly Tyr His Tyr Ile Ile Ala Asn Leu Gly Phe Lys
230                 235                 240                 245

GAT ATT TCT CTT GAG AGA TTT ATA CAT GGA GGA GCA AAT GTA ACA GGA        944
Asp Ile Ser Leu Glu Arg Phe Ile His Gly Gly Ala Asn Val Thr Gly
                250                 255                 260

TTC CAG TTG GTA GAT TTT AAT ACA CCC ATG GTA ACC AAA CTA ATG GAT        992
Phe Gln Leu Val Asp Phe Asn Thr Pro Met Val Thr Lys Leu Met Asp
```

-continued

|  | 265 | | | | | 270 | | | | | 275 | | |  |
|---|---|---|---|---|---|---|---|---|---|---|---|---|---|---|
| CGG | TGG | AAG | AAA | CTA | GAT | CAG | AGA | GAA | TAT | CCA | GGT | TCT | GAA | ACA | CCT | 1040 |
| Arg | Trp | Lys | Lys | Leu | Asp | Gln | Arg | Glu | Tyr | Pro | Gly | Ser | Glu | Thr | Pro |  |
|  |  | 280 |  |  |  |  | 285 |  |  |  |  | 290 |  |  |  |  |
| CCA | AAG | TAC | ACC | TCT | GCT | CTC | ACT | TAT | GAT | GGA | GTC | CTG | GTG | ATG | GCT | 1088 |
| Pro | Lys | Tyr | Thr | Ser | Ala | Leu | Thr | Tyr | Asp | Gly | Val | Leu | Val | Met | Ala |  |
|  | 295 |  |  |  |  | 300 |  |  |  |  | 305 |  |  |  |  |  |
| GAA | ACT | TTC | CGA | AGT | CTC | AGA | AGA | CAG | AAA | ATT | GAT | ATT | TCA | AGG | AGA | 1136 |
| Glu | Thr | Phe | Arg | Ser | Leu | Arg | Arg | Gln | Lys | Ile | Asp | Ile | Ser | Arg | Arg |  |
| 310 |  |  |  |  | 315 |  |  |  |  | 320 |  |  |  |  | 325 |  |
| GGA | AAT | GCT | GGG | GAC | TGT | CTG | GCA | AAC | CCT | GCT | GCT | CCC | TGG | GGC | CAG | 1184 |
| Gly | Asn | Ala | Gly | Asp | Cys | Leu | Ala | Asn | Pro | Ala | Ala | Pro | Trp | Gly | Gln |  |
|  |  |  | 330 |  |  |  |  | 335 |  |  |  |  | 340 |  |  |  |
| GGA | ATT | GAC | ATG | GAG | AGG | ACA | CTG | AAG | CAG | GTT | CGA | ATT | CAA | GGG | CTG | 1232 |
| Gly | Ile | Asp | Met | Glu | Arg | Thr | Leu | Lys | Gln | Val | Arg | Ile | Gln | Gly | Leu |  |
|  |  | 345 |  |  |  |  | 350 |  |  |  |  | 355 |  |  |  |  |
| ACT | GGG | AAT | GTT | CAA | TTT | GAC | CAT | TAT | GGA | CGT | AGA | GTT | AAT | TAC | ACA | 1280 |
| Thr | Gly | Asn | Val | Gln | Phe | Asp | His | Tyr | Gly | Arg | Arg | Val | Asn | Tyr | Thr |  |
|  | 360 |  |  |  |  | 365 |  |  |  |  | 370 |  |  |  |  |  |
| ATG | GAT | GTG | TTT | GAA | CTA | AAA | AGC | ACA | GGA | CCT | CGA | AAG | GTT | GGC | TAC | 1328 |
| Met | Asp | Val | Phe | Glu | Leu | Lys | Ser | Thr | Gly | Pro | Arg | Lys | Val | Gly | Tyr |  |
| 375 |  |  |  |  | 380 |  |  |  |  | 385 |  |  |  |  |  |  |
| TGG | AAT | GAT | ATG | GAT | AAA | TTA | GTC | TTG | ATT | CAA | GAT | ATG | CCT | ACT | CTG | 1376 |
| Trp | Asn | Asp | Met | Asp | Lys | Leu | Val | Leu | Ile | Gln | Asp | Met | Pro | Thr | Leu |  |
| 390 |  |  |  |  | 395 |  |  |  |  | 400 |  |  |  |  | 405 |  |
| GGC | AAT | GAC | ACA | GCA | GCT | ATT | GAG | AAC | AGA | ACA | GTG | GTT | GTA | ACC | ACA | 1424 |
| Gly | Asn | Asp | Thr | Ala | Ala | Ile | Glu | Asn | Arg | Thr | Val | Val | Val | Thr | Thr |  |
|  |  |  | 410 |  |  |  |  | 415 |  |  |  |  | 420 |  |  |  |
| ATT | ATG | GAA | TCT | CCC | TAT | GTT | ATG | TAC | AAG | AAA | AAT | CAT | GAA | ATG | TTT | 1472 |
| Ile | Met | Glu | Ser | Pro | Tyr | Val | Met | Tyr | Lys | Lys | Asn | His | Glu | Met | Phe |  |
|  |  | 425 |  |  |  |  | 430 |  |  |  |  | 435 |  |  |  |  |
| GAA | GGA | AAT | GAC | AAG | TAC | GAA | GGC | TAC | TGT | GTA | GAT | CTG | GCA | TCG | GAA | 1520 |
| Glu | Gly | Asn | Asp | Lys | Tyr | Glu | Gly | Tyr | Cys | Val | Asp | Leu | Ala | Ser | Glu |  |
|  | 440 |  |  |  |  | 445 |  |  |  |  | 450 |  |  |  |  |  |
| AGT | GCA | AAA | CAT | ATT | GGT | ATC | AAA | TAT | AAA | ATT | GCC | ATT | GTT | CCT | GAT | 1568 |
| Ser | Ala | Lys | His | Ile | Gly | Ile | Lys | Tyr | Lys | Ile | Ala | Ile | Val | Pro | Asp |  |
|  | 455 |  |  |  |  | 460 |  |  |  |  | 465 |  |  |  |  |  |
| GGA | AAA | TAT | GGA | GCA | AGG | GAC | GCA | GAC | ACT | AAG | ATC | TGG | AAT | GGG | ATG | 1616 |
| Gly | Lys | Tyr | Gly | Ala | Arg | Asp | Ala | Asp | Thr | Lys | Ile | Trp | Asn | Gly | Met |  |
| 470 |  |  |  |  | 475 |  |  |  |  | 480 |  |  |  |  | 485 |  |
| GTA | GGA | GAG | CTT | GTG | TAT | GGG | AAA | GCA | GAG | ATT | GCT | ATT | GCC | CCT | CTG | 1664 |
| Val | Gly | Glu | Leu | Val | Tyr | Gly | Lys | Ala | Glu | Ile | Ala | Ile | Ala | Pro | Leu |  |
|  |  |  | 490 |  |  |  |  | 495 |  |  |  |  | 500 |  |  |  |
| ACA | ATC | ACA | TTG | GTT | CGA | GAG | GAA | GTC | ATC | GAT | TTT | TCT | AAG | CCT | TTT | 1712 |
| Thr | Ile | Thr | Leu | Val | Arg | Glu | Glu | Val | Ile | Asp | Phe | Ser | Lys | Pro | Phe |  |
|  |  | 505 |  |  |  |  | 510 |  |  |  |  | 515 |  |  |  |  |
| ATG | AGT | TTA | GGC | ATC | TCT | ATC | ATG | ATC | AAA | AAA | CCT | CAG | AAA | TCT | AAA | 1760 |
| Met | Ser | Leu | Gly | Ile | Ser | Ile | Met | Ile | Lys | Lys | Pro | Gln | Lys | Ser | Lys |  |
|  |  | 520 |  |  |  |  | 525 |  |  |  |  | 530 |  |  |  |  |
| CCA | GGA | GTC | TTT | TCC | TTC | TTG | GAC | CCT | CTG | GCC | TAT | GAG | ATC | TGG | ATG | 1808 |
| Pro | Gly | Val | Phe | Ser | Phe | Leu | Asp | Pro | Leu | Ala | Tyr | Glu | Ile | Trp | Met |  |
|  | 535 |  |  |  |  | 540 |  |  |  |  | 545 |  |  |  |  |  |
| TGC | ATA | GTG | TTT | GCA | TAC | ATT | GGT | GTC | AGT | GTG | GTC | TTG | TTC | CTA | GTC | 1856 |
| Cys | Ile | Val | Phe | Ala | Tyr | Ile | Gly | Val | Ser | Val | Val | Leu | Phe | Leu | Val |  |
| 550 |  |  |  |  | 555 |  |  |  |  | 560 |  |  |  |  | 565 |  |
| AGT | AGG | TTT | AGC | CCA | TAT | GAG | TGG | CAC | ACA | GAA | GAA | CCT | GAG | GAT | GGG | 1904 |
| Ser | Arg | Phe | Ser | Pro | Tyr | Glu | Trp | His | Thr | Glu | Glu | Pro | Glu | Asp | Gly |  |
|  |  |  | 570 |  |  |  |  | 575 |  |  |  |  | 580 |  |  |  |
| AAG | GAA | GGA | CCC | AGT | GAC | CAG | CCT | CCC | AAT | GAA | TTT | GGC | ATC | TTT | AAC | 1952 |
| Lys | Glu | Gly | Pro | Ser | Asp | Gln | Pro | Pro | Asn | Glu | Phe | Gly | Ile | Phe | Asn |  |

```
                          585                     590                       595
AGC CTT TGG TTT TCC CTG GGT GCC TTT ATG CAA CAA GGA TGT GAC ATT          2000
Ser Leu Trp Phe Ser Leu Gly Ala Phe Met Gln Gln Gly Cys Asp Ile
            600                     605                     610

TCA CCC AGA TCC CTG TCA GGT CGG ATT GTT GGA GGC GTG TGG TGG TTC          2048
Ser Pro Arg Ser Leu Ser Gly Arg Ile Val Gly Gly Val Trp Trp Phe
    615                     620                     625

TTC ACA CTC ATC ATT ATA TCG TCC TAC ACT GCT AAT CTG GCT GCA TTC          2096
Phe Thr Leu Ile Ile Ile Ser Ser Tyr Thr Ala Asn Leu Ala Ala Phe
630                     635                     640                     645

CTT ACT GTG GAG AGA ATG GTC TCC CCC ATA GAA AGT GCA GAA GAC CTG          2144
Leu Thr Val Glu Arg Met Val Ser Pro Ile Glu Ser Ala Glu Asp Leu
                650                     655                     660

GCC AAA CAA ACA GAA ATT GCC TAT GGA ACA CTT GAT TCT GGG TCA ACA          2192
Ala Lys Gln Thr Glu Ile Ala Tyr Gly Thr Leu Asp Ser Gly Ser Thr
    665                     670                     675

AAA GAA TTC TTC AGA AGA TCA AAA ATA GCA GTG TAT GAA AAG ATG TGG          2240
Lys Glu Phe Phe Arg Arg Ser Lys Ile Ala Val Tyr Glu Lys Met Trp
            680                     685                     690

ACC TAC ATG CGA TCG GCA GAG CCG TCT GTG TTC ACT AGA ACT ACA GCT          2288
Thr Tyr Met Arg Ser Ala Glu Pro Ser Val Phe Thr Arg Thr Thr Ala
695                     700                     705

GAG GGC GTG GCT CGT GTC CGC AAG TCC AAG GGC AAA TTT GCC TTT CTC          2336
Glu Gly Val Ala Arg Val Arg Lys Ser Lys Gly Lys Phe Ala Phe Leu
710                     715                     720                     725

CTG GAG TCC ACG ATG AAT GAA TAC ATT GAG CAG CGA AAG CCC TGT GAC          2384
Leu Glu Ser Thr Met Asn Glu Tyr Ile Glu Gln Arg Lys Pro Cys Asp
                730                     735                     740

ACG ATG AAA GTG GGA GGA AAC CTG GAT TCC AAA GGC TAT GGT GTA GCA          2432
Thr Met Lys Val Gly Gly Asn Leu Asp Ser Lys Gly Tyr Gly Val Ala
            745                     750                     755

ACG CCC AAG GGT TCC TCA TTA AGA ACT CCT GTA AAC CTT GCC GTT TTG          2480
Thr Pro Lys Gly Ser Ser Leu Arg Thr Pro Val Asn Leu Ala Val Leu
    760                     765                     770

AAA CTC AGT GAG GCA GGC GTC TTA GAC AAG CTG AAA AAC AAA TGG TGG          2528
Lys Leu Ser Glu Ala Gly Val Leu Asp Lys Leu Lys Asn Lys Trp Trp
775                     780                     785

TAC GAT AAA GGT GAA TGT GGA CCC AAG GAC TCG GGA AGC AAG GAC AAG          2576
Tyr Asp Lys Gly Glu Cys Gly Pro Lys Asp Ser Gly Ser Lys Asp Lys
790                     795                     800                     805

ACG AGT GCC TTG AGC CTG AGC AAC GTA GCA GGC GTC TTC TAC ATT CTG          2624
Thr Ser Ala Leu Ser Leu Ser Asn Val Ala Gly Val Phe Tyr Ile Leu
                810                     815                     820

GTT GGC GGC CTG GGC TTG GCA ATG CTG GTG GCT TTG ATA GAG TTC TGT          2672
Val Gly Gly Leu Gly Leu Ala Met Leu Val Ala Leu Ile Glu Phe Cys
            825                     830                     835

TAC AAG TCC AGG GCA GAG GCG AAG AGA ATG AAG CTG ACT TTT TCC GAA          2720
Tyr Lys Ser Arg Ala Glu Ala Lys Arg Met Lys Leu Thr Phe Ser Glu
    840                     845                     850

GCC ATA AGA AAC AAA GCC AGG TTA TCC ATC ACT GGG AGT GTG GGA GAA          2768
Ala Ile Arg Asn Lys Ala Arg Leu Ser Ile Thr Gly Ser Val Gly Glu
855                     860                     865

AAC GGC CGT GTG CTT ACC CCT GAC TGC CCC AAG GCC GTA CAC ACA GGA          2816
Asn Gly Arg Val Leu Thr Pro Asp Cys Pro Lys Ala Val His Thr Gly
870                     875                     880                     885

ACT GCA ATT AGA CAA AGT TCG GGA TTG GCT GTC ATT GCA TCG GAC CTA          2864
Thr Ala Ile Arg Gln Ser Ser Gly Leu Ala Val Ile Ala Ser Asp Leu
                890                     895                     900

CCA TAAAACCAA AAAAATAATT GAGTGCCTTA ATCAAACTGT GTTGGTGACT GACTGA        2923
Pro
```

AACGCAGCCC TGAGGGAAAG GCCAAGAGTG GGTCTTGACT AAATCCAT                    2971

(2) INFORMATION FOR SEQ ID NO:8:

(i) SEQUENCE CHARACTERISTICS:
        (A) LENGTH: 902 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Met Arg Ile Ile Cys Arg Gln Ile Val Leu Leu Phe Ser Gly Phe Trp
 1               5                  10                  15

Gly Leu Ala Met Gly Ala Phe Pro Ser Val Gln Ile Gly Gly Leu
             20                  25                  30

Phe Ile Arg Asn Thr Asp Gln Glu Tyr Thr Ala Phe Arg Leu Ala Ile
             35                  40                  45

Phe Leu His Asn Thr Ser Pro Asn Ala Ser Glu Ala Pro Phe Asn Leu
         50                  55                  60

Val Pro His Val Asp Asn Ile Glu Thr Ala Asn Ser Phe Ala Val Thr
65                  70                  75                  80

Asn Ala Phe Cys Ser Gln Tyr Ser Arg Gly Val Phe Ala Ile Phe Gly
                 85                  90                  95

Leu Tyr Asp Lys Arg Ser Val His Thr Leu Thr Ser Phe Cys Arg Arg
                100                 105                 110

Leu His Ile Ser Leu Ile Thr Pro Ser Phe Pro Thr Glu Gly Glu Ser
            115                 120                 125

Gln Phe Val Leu Gln Leu Arg Pro Ser Leu Arg Gly Ala Leu Leu Ser
        130                 135                 140

Leu Leu Asp His Tyr Glu Trp Asn Cys Phe Val Phe Leu Tyr Asp Thr
145                 150                 155                 160

Asp Arg Gly Tyr Ser Ile Leu Gln Ala Ile Met Glu Lys Ala Gly Gln
                165                 170                 175

Asn Gly Trp His Val Ser Ala Ile Cys Val Glu Asn Phe Asn Asp Val
            180                 185                 190

Ser Tyr Arg Gln Leu Leu Glu Glu Leu Asp Arg Arg Gln Glu Lys Lys
        195                 200                 205

Phe Val Ile Asp Cys Glu Ile Glu Arg Leu Gln Asn Ile Leu Glu Gln
    210                 215                 220

Ile Val Ser Val Gly Lys His Val Lys Gly Tyr His Tyr Ile Ile Ala
225                 230                 235                 240

Asn Leu Gly Phe Lys Asp Ile Ser Leu Glu Arg Phe Ile His Gly Gly
                245                 250                 255

Ala Asn Val Thr Gly Phe Gln Leu Val Asp Phe Asn Thr Pro Met Val
            260                 265                 270

Thr Lys Leu Met Asp Arg Trp Lys Lys Leu Asp Gln Arg Glu Tyr Pro
        275                 280                 285

Gly Ser Glu Thr Pro Pro Lys Tyr Thr Ser Ala Leu Thr Tyr Asp Gly
    290                 295                 300

Val Leu Val Met Ala Glu Thr Phe Arg Ser Leu Arg Arg Gln Lys Ile
305                 310                 315                 320

Asp Ile Ser Arg Arg Gly Asn Ala Gly Asp Cys Leu Ala Asn Pro Ala
                325                 330                 335

Ala Pro Trp Gly Gln Gly Ile Asp Met Glu Arg Thr Leu Lys Gln Val
```

-continued

```
               340                 345                 350
Arg Ile Gln Gly Leu Thr Gly Asn Val Gln Phe Asp His Tyr Gly Arg
            355                 360                 365
Arg Val Asn Tyr Thr Met Asp Val Phe Glu Leu Lys Ser Thr Gly Pro
        370                 375                 380
Arg Lys Val Gly Tyr Trp Asn Asp Met Asp Lys Leu Val Leu Ile Gln
385                 390                 395                 400
Asp Met Pro Thr Leu Gly Asn Asp Thr Ala Ala Ile Glu Asn Arg Thr
                405                 410                 415
Val Val Val Thr Thr Ile Met Glu Ser Pro Tyr Val Met Tyr Lys Lys
            420                 425                 430
Asn His Glu Met Phe Glu Gly Asn Asp Lys Tyr Glu Gly Tyr Cys Val
        435                 440                 445
Asp Leu Ala Ser Glu Ser Ala Lys His Ile Gly Ile Lys Tyr Lys Ile
    450                 455                 460
Ala Ile Val Pro Asp Gly Lys Tyr Gly Ala Arg Asp Ala Asp Thr Lys
465                 470                 475                 480
Ile Trp Asn Gly Met Val Gly Glu Leu Val Tyr Gly Lys Ala Glu Ile
                485                 490                 495
Ala Ile Ala Pro Leu Thr Ile Thr Leu Val Arg Glu Glu Val Ile Asp
            500                 505                 510
Phe Ser Lys Pro Phe Met Ser Leu Gly Ile Ser Ile Met Ile Lys Lys
        515                 520                 525
Pro Gln Lys Ser Lys Pro Gly Val Phe Ser Phe Leu Asp Pro Leu Ala
    530                 535                 540
Tyr Glu Ile Trp Met Cys Ile Val Phe Ala Tyr Ile Gly Val Ser Val
545                 550                 555                 560
Val Leu Phe Leu Val Ser Arg Phe Ser Pro Tyr Glu Trp His Thr Glu
                565                 570                 575
Glu Pro Glu Asp Gly Lys Glu Gly Pro Ser Asp Gln Pro Pro Asn Glu
            580                 585                 590
Phe Gly Ile Phe Asn Ser Leu Trp Phe Ser Leu Gly Ala Phe Met Gln
        595                 600                 605
Gln Gly Cys Asp Ile Ser Pro Arg Ser Leu Ser Gly Arg Ile Val Gly
    610                 615                 620
Gly Val Trp Trp Phe Phe Thr Leu Ile Ile Ile Ser Ser Tyr Thr Ala
625                 630                 635                 640
Asn Leu Ala Ala Phe Leu Thr Val Glu Arg Met Val Ser Pro Ile Glu
                645                 650                 655
Ser Ala Glu Asp Leu Ala Lys Gln Thr Glu Ile Ala Tyr Gly Thr Leu
            660                 665                 670
Asp Ser Gly Ser Thr Lys Glu Phe Phe Arg Arg Ser Lys Ile Ala Val
        675                 680                 685
Tyr Glu Lys Met Trp Thr Tyr Met Arg Ser Ala Glu Pro Ser Val Phe
    690                 695                 700
Thr Arg Thr Thr Ala Glu Gly Val Ala Arg Val Arg Lys Ser Lys Gly
705                 710                 715                 720
Lys Phe Ala Phe Leu Leu Glu Ser Thr Met Asn Glu Tyr Ile Glu Gln
                725                 730                 735
Arg Lys Pro Cys Asp Thr Met Lys Val Gly Gly Asn Leu Asp Ser Lys
            740                 745                 750
Gly Tyr Gly Val Ala Thr Pro Lys Gly Ser Ser Leu Arg Thr Pro Val
        755                 760                 765
```

```
Asn Leu Ala Val Leu Lys Leu Ser Glu Ala Gly Val Leu Asp Lys Leu
    770                 775                 780
Lys Asn Lys Trp Trp Tyr Asp Lys Gly Glu Cys Gly Pro Lys Asp Ser
785                 790                 795                 800
Gly Ser Lys Asp Lys Thr Ser Ala Leu Ser Leu Ser Asn Val Ala Gly
                805                 810                 815
Val Phe Tyr Ile Leu Val Gly Gly Leu Gly Leu Ala Met Leu Val Ala
            820                 825                 830
Leu Ile Glu Phe Cys Tyr Lys Ser Arg Ala Glu Ala Lys Arg Met Lys
            835                 840                 845
Leu Thr Phe Ser Glu Ala Ile Arg Asn Lys Ala Arg Leu Ser Ile Thr
    850                 855                 860
Gly Ser Val Gly Glu Asn Gly Arg Val Leu Thr Pro Asp Cys Pro Lys
865                 870                 875                 880
Ala Val His Thr Gly Thr Ala Ile Arg Gln Ser Ser Gly Leu Ala Val
                885                 890                 895
Ile Ala Ser Asp Leu Pro
                900
```

(2) INFORMATION FOR SEQ ID NO:9:

(i) SEQUENCE CHARACTERISTICS:
        (A) LENGTH: 3250 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: GluR5

(ix) FEATURE:
        (A) NAME/KEY: Coding Sequence
        (B) LOCATION: 188...2947
        (D) OTHER INFORMATION:

(xi) SEQUENCE DESCRIPTION: SEQ ID NO:9:

```
GGCTAGGAAG CCCGCTTCAC GTCCCCACGC TTGTTCCCTC CACCTCGCTC TCCTGAGAGC      60

AGAGAGCGCG CGGTGTGCAG ACTCGGAGCA TTCCGGGAGG ATGAGGCGGG GACCCAGCCC     120

AAGTTGGGTG CATCTTGCGG GCGTGAGGCC ACAACTGGGT TTCGGCATGA ATTAAGAAGC     180

TTGAAAG ATG GAG CGC AGC ACA GTC CTT ATC CAA CCC GGG CTC TGG ACC      229
        Met Glu Arg Ser Thr Val Leu Ile Gln Pro Gly Leu Trp Thr
        1               5                   10

AGG GAC ACC AGC TGG ACA CTC CTC TAT TTC CTG TGC TAC ATC CTC CCT      277
Arg Asp Thr Ser Trp Thr Leu Leu Tyr Phe Leu Cys Tyr Ile Leu Pro
 15                  20                  25                  30

CAG ACC TCC CCT CAA GTG CTC AGG ATC GGA GGG ATT TTT GAA ACT GTG      325
Gln Thr Ser Pro Gln Val Leu Arg Ile Gly Gly Ile Phe Glu Thr Val
                35                  40                  45

GAA AAT GAA CCT GTT AAT GTT GAA GAA TTA GCT TTC AAG TTT GCA GTC      373
Glu Asn Glu Pro Val Asn Val Glu Glu Leu Ala Phe Lys Phe Ala Val
            50                  55                  60

ACC AGT ATT AAC CGA AAC CGA ACC TTG ATG CCC AAT ACC ACA TTA ACC      421
Thr Ser Ile Asn Arg Asn Arg Thr Leu Met Pro Asn Thr Thr Leu Thr
                65                  70                  75

TAT GAC ATC CAG AGA ATT AAT CTT TTT GAT AGT TTT GAA GCC TCC CGA      469
Tyr Asp Ile Gln Arg Ile Asn Leu Phe Asp Ser Phe Glu Ala Ser Arg
 80                  85                  90

AGA GCA TGC GAC CAG CTG GCT CTC GGG GTG GCC GCA CTC TTC GGC CCT      517
Arg Ala Cys Asp Gln Leu Ala Leu Gly Val Ala Ala Leu Phe Gly Pro
```

```
            95                    100                   105                   110
TCC CAC AGC TCC TCC GTC AGT GCT GTA CAG TCT ATT TGC AAT GCT CTG        565
Ser His Ser Ser Ser Val Ser Ala Val Gln Ser Ile Cys Asn Ala Leu
                        115                   120                   125

GAA GTT CCA CAC ATT CAG ACT CGC TGG AAA CAC CCT TCC GTG GAC AGC        613
Glu Val Pro His Ile Gln Thr Arg Trp Lys His Pro Ser Val Asp Ser
                130                   135                   140

AGA GAC CTA TTT TAT ATC AAC CTC TAC CCG GAC TAT GCG GCT ATC AGC        661
Arg Asp Leu Phe Tyr Ile Asn Leu Tyr Pro Asp Tyr Ala Ala Ile Ser
            145                   150                   155

AGG GCG GTC CTG GAT TTG GTC CTC TAT TAC AAC TGG AAA ACA GTG ACG        709
Arg Ala Val Leu Asp Leu Val Leu Tyr Tyr Asn Trp Lys Thr Val Thr
        160                   165                   170

GTG GTG TAT GAA GAT AGC ACA GGT CTA ATT CGT CTG CAA GAG CTC ATC        757
Val Val Tyr Glu Asp Ser Thr Gly Leu Ile Arg Leu Gln Glu Leu Ile
175                   180                   185                   190

AAA GCT CCC TCC AGA TAC AAC ATT AAA ATC AAA ATC CGC CAG CTT CCC        805
Lys Ala Pro Ser Arg Tyr Asn Ile Lys Ile Lys Ile Arg Gln Leu Pro
                        195                   200                   205

CCT GCG AAT AAA GAC GCC AAA CCT CTG CTC AAG GAG ATG AAG AAA AGC        853
Pro Ala Asn Lys Asp Ala Lys Pro Leu Leu Lys Glu Met Lys Lys Ser
                210                   215                   220

AAA GAG TTC TAT GTG ATA TTT GAT TGT TCG CAC GAA ACA GCT GCG GAA        901
Lys Glu Phe Tyr Val Ile Phe Asp Cys Ser His Glu Thr Ala Ala Glu
            225                   230                   235

ATT CTT AAG CAG ATT TTG TTC ATG GGC ATG ATG ACT GAA TAT TAT CAC        949
Ile Leu Lys Gln Ile Leu Phe Met Gly Met Met Thr Glu Tyr Tyr His
        240                   245                   250

TAC TTC TTC ACA ACC CTG GAC TTG TTT GCT TTA GAT CTG GAA CTC TAT        997
Tyr Phe Phe Thr Thr Leu Asp Leu Phe Ala Leu Asp Leu Glu Leu Tyr
255                   260                   265                   270

AGG TAC AGC GGT GTA AAT ATG ACT GGA TTT CGG TTG CTG AAT ATT GAC       1045
Arg Tyr Ser Gly Val Asn Met Thr Gly Phe Arg Leu Leu Asn Ile Asp
                        275                   280                   285

AAC CCT CAC GTG TCA TCC ATC ATT GAG AAG TGG TCC ATG GAG AGG TTG       1093
Asn Pro His Val Ser Ser Ile Ile Glu Lys Trp Ser Met Glu Arg Leu
                290                   295                   300

CAG GCC CCG CCC AGA CCC GAG ACT GGT CTT CTG GAT GGC ATG ATG ACA       1141
Gln Ala Pro Pro Arg Pro Glu Thr Gly Leu Leu Asp Gly Met Met Thr
            305                   310                   315

ACT GAA GCA GCG CTG ATG TAC GAT GCT GTG TAC ATG GTA GCC ATT GCG       1189
Thr Glu Ala Ala Leu Met Tyr Asp Ala Val Tyr Met Val Ala Ile Ala
        320                   325                   330

TCC CAC CGT GCC TCT CAG CTG ACC GTC AGC TCC CTG CAG TGC CAT CGA       1237
Ser His Arg Ala Ser Gln Leu Thr Val Ser Ser Leu Gln Cys His Arg
335                   340                   345                   350

CAT AAG CCA TGG CGC CTT GGA CCC AGA TTT ATG AAC CTC ATC AAA GAG       1285
His Lys Pro Trp Arg Leu Gly Pro Arg Phe Met Asn Leu Ile Lys Glu
                        355                   360                   365

GCT CGG TGG GAC GGC TTG ACT GGG CGG ATC ACC TTC AAT AAG ACC GAT       1333
Ala Arg Trp Asp Gly Leu Thr Gly Arg Ile Thr Phe Asn Lys Thr Asp
                370                   375                   380

GGC TTG AGA AAG GAT TTT GAC CTG GAC ATT ATC AGT CTC AAA GAG GAA       1381
Gly Leu Arg Lys Asp Phe Asp Leu Asp Ile Ile Ser Leu Lys Glu Glu
            385                   390                   395

GGA ACT GAA AAG GCC TCT GGT GAA GTG TCT AAA CAC TTG TAT AAA GTG       1429
Gly Thr Glu Lys Ala Ser Gly Glu Val Ser Lys His Leu Tyr Lys Val
        400                   405                   410

TGG AAG AAG ATT GGG ATT TGG AAC TCC AAC AGT GGG CTG AAC ATG ACG       1477
Trp Lys Lys Ile Gly Ile Trp Asn Ser Asn Ser Gly Leu Asn Met Thr
```

```
          415                 420                 425                 430
GAT GGC AAC AGA GAC AGG TCC AAC AAT ATC ACG GAC TCG CTG GCT AAC          1525
Asp Gly Asn Arg Asp Arg Ser Asn Asn Ile Thr Asp Ser Leu Ala Asn
                    435                 440                 445

CGC ACA CTC ATT GTC ACC ACT ATT CTG GAA GAG CCC TAC GTG ATG TAC          1573
Arg Thr Leu Ile Val Thr Thr Ile Leu Glu Glu Pro Tyr Val Met Tyr
                450                 455                 460

AGG AAA TCC GAT AAG CCC TTG TAT GGA AAC GAC AGG TTT GAA GGA TAT          1621
Arg Lys Ser Asp Lys Pro Leu Tyr Gly Asn Asp Arg Phe Glu Gly Tyr
            465                 470                 475

TGC CTG GAT CTG CTG AAA GAA CTG TCC AAT ATC CTG GGT TTT CTT TAC          1669
Cys Leu Asp Leu Leu Lys Glu Leu Ser Asn Ile Leu Gly Phe Leu Tyr
        480                 485                 490

GAT GTT AAA CTG GTT CCT GAT GGC AAA TAT GGA GCA CAG AAT GAC AAA          1717
Asp Val Lys Leu Val Pro Asp Gly Lys Tyr Gly Ala Gln Asn Asp Lys
495                 500                 505                 510

GGG GAA TGG AAT GGG ATG GTA AAA GAA CTC ATC GAC CAC AGA GCT GAC          1765
Gly Glu Trp Asn Gly Met Val Lys Glu Leu Ile Asp His Arg Ala Asp
                    515                 520                 525

CTG GCA GTG GCC CCT CTC ACC ATC ACA TAC GTA CGG GAG AAA GTC ATT          1813
Leu Ala Val Ala Pro Leu Thr Ile Thr Tyr Val Arg Glu Lys Val Ile
                530                 535                 540

GAC TTC TCC AAG CCC TTC ATG ACC CTG GGC ATT AGC ATC CTT TAC CGG          1861
Asp Phe Ser Lys Pro Phe Met Thr Leu Gly Ile Ser Ile Leu Tyr Arg
            545                 550                 555

AAG CCC AAT GGA ACC AAC CCG GGT GTC TTC TCC TTC CTC AAC CCC CTA          1909
Lys Pro Asn Gly Thr Asn Pro Gly Val Phe Ser Phe Leu Asn Pro Leu
        560                 565                 570

TCT CCG GAC ATT TGG ATG TAC GTG CTG CTC GCC TGC CTA GGA GTC AGT          1957
Ser Pro Asp Ile Trp Met Tyr Val Leu Leu Ala Cys Leu Gly Val Ser
575                 580                 585                 590

TGT GTA CTG TTT GTG ATT GCG AGG TTC ACA CCC TAC GAG TGG TAT AAC          2005
Cys Val Leu Phe Val Ile Ala Arg Phe Thr Pro Tyr Glu Trp Tyr Asn
                    595                 600                 605

CCC CAC CCA TGC AAC CCC GAC TCA GAC GTG GTG GAA AAC AAT TTC ACT          2053
Pro His Pro Cys Asn Pro Asp Ser Asp Val Val Glu Asn Asn Phe Thr
                610                 615                 620

TTG CTA AAT AGT TTC TGG TTT GGA GTT GGA GCT CTC ATG CAG CAA GGA          2101
Leu Leu Asn Ser Phe Trp Phe Gly Val Gly Ala Leu Met Gln Gln Gly
            625                 630                 635

TCA GAG CTG ATG CCC AAG GCT CTA TCG ACC AGA ATA GTT GGA GGA ATA          2149
Ser Glu Leu Met Pro Lys Ala Leu Ser Thr Arg Ile Val Gly Gly Ile
        640                 645                 650

TGG TGG TTT TTC ACC CTA ATC ATC ATT TCA TCC TAC ACG GCC AAC CTG          2197
Trp Trp Phe Phe Thr Leu Ile Ile Ile Ser Ser Tyr Thr Ala Asn Leu
655                 660                 665                 670

GCT GCC TTC TTG ACG GTA GAA AGA ATG GAA TCC CCC ATC GAT TCC GCA          2245
Ala Ala Phe Leu Thr Val Glu Arg Met Glu Ser Pro Ile Asp Ser Ala
                    675                 680                 685

GAC GAT CTG GCC AAA CAA ACC AAG ATA GAA TAT GGG GCA GTC AGA GAT          2293
Asp Asp Leu Ala Lys Gln Thr Lys Ile Glu Tyr Gly Ala Val Arg Asp
                690                 695                 700

GGC TCG ACG ATG ACC TTC TTC AAG AAA TCA AAG ATC TCC ACC TAT GAG          2341
Gly Ser Thr Met Thr Phe Phe Lys Lys Ser Lys Ile Ser Thr Tyr Glu
            705                 710                 715

AAA ATG TGG GCT TTC ATG AGC AGT AGA CAG CAG AGC GCA CTG GTT AAA          2389
Lys Met Trp Ala Phe Met Ser Ser Arg Gln Gln Ser Ala Leu Val Lys
        720                 725                 730

AAC AGT GAC GAG GGG ATC CAA AGG GTG CTC ACC ACC GAC TAC GCA CTG          2437
Asn Ser Asp Glu Gly Ile Gln Arg Val Leu Thr Thr Asp Tyr Ala Leu
```

```
                     735                 740                 745                 750
CTG ATG GAG TCC ACC AGC ATT GAG TAT GTG ACG CAG AGG AAC TGC AAC                    2485
Leu Met Glu Ser Thr Ser Ile Glu Tyr Val Thr Gln Arg Asn Cys Asn
                         755                 760                 765

CTC ACT CAG ATC GGG GGC CTC ATA GAC TCC AAA GGC TAT GGA GTG GGG                    2533
Leu Thr Gln Ile Gly Gly Leu Ile Asp Ser Lys Gly Tyr Gly Val Gly
                 770                 775                 780

ACG CCT ATC GGC TCC CCT TAC CGG GAT AAA ATT ACG ATT GCC ATT CTT                    2581
Thr Pro Ile Gly Ser Pro Tyr Arg Asp Lys Ile Thr Ile Ala Ile Leu
             785                 790                 795

CAA CTG CAA GAA GAA GGG AAG CTT CAT ATG ATG AAA GAG AAG TGG TGG                    2629
Gln Leu Gln Glu Glu Gly Lys Leu His Met Met Lys Glu Lys Trp Trp
         800                 805                 810

AGG GGG AAT GGC TGC CCT GAA GAA GAC AGT AAG GAA GCC AGT GCT CTG                    2677
Arg Gly Asn Gly Cys Pro Glu Glu Asp Ser Lys Glu Ala Ser Ala Leu
815                 820                 825                 830

GGA GTG GAA AAT ATC GGC GGC ATC TTC ATT GTT CTG GCT GCA GGA CTC                    2725
Gly Val Glu Asn Ile Gly Gly Ile Phe Ile Val Leu Ala Ala Gly Leu
                         835                 840                 845

GTG CTT TCT GTG TTT GTA GCC ATT GGA GAA TTT TTA TAC AAA TCA CGG                    2773
Val Leu Ser Val Phe Val Ala Ile Gly Glu Phe Leu Tyr Lys Ser Arg
                 850                 855                 860

AAG AAC AAT GAC GTT GAG CAG TGT CTC TCT TTC AAT GCC ATC ATG GAA                    2821
Lys Asn Asn Asp Val Glu Gln Cys Leu Ser Phe Asn Ala Ile Met Glu
             865                 870                 875

GAG CTG GGA ATA TCC CTC AAG AAT CAG AAA AAA TTA AAG AAA AAG TCA                    2869
Glu Leu Gly Ile Ser Leu Lys Asn Gln Lys Lys Leu Lys Lys Lys Ser
         880                 885                 890

AGA ACT AAG GGC AAA TCT TCT TTC ACA AGT ATC CTT ACT TGT CAC CAG                    2917
Arg Thr Lys Gly Lys Ser Ser Phe Thr Ser Ile Leu Thr Cys His Gln
895                 900                 905                 910

AGA CGA ACT CAG AGA AAA GAG ACA GTG GCG TGATCAAAGA ACACACCTGT AAG                  2970
Arg Arg Thr Gln Arg Lys Glu Thr Val Ala
                         915                 920

AAGAAAAAGC CCACACGTCC GCTGCACATA TTTGGAGGAC AGATTTCAGA GGACTATGTC                  3030

TTTATCCATA ACCCCAGTCG TGGACAGAGG GGGAAGAAAT GCACAATTTT TAAAGCTCAC                  3090

ATAGATATTA CTTGAGAAGT GAAACTGATT CTTTTCAGAT GAATTTGTAT GCACACTTAT                  3150

TTTGAATTTT TCCATTTCCT CCGATAAATT GCTATGTGTG CTTTCTAAAT AATAATAAAC                  3210

AAGCGGACTT TGTTTTTCAT AAAAAAAAAA AAAAAAAAA                                         3250

(2) INFORMATION FOR SEQ ID NO:10:

(i) SEQUENCE CHARACTERISTICS:
        (A) LENGTH: 920 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Met Glu Arg Ser Thr Val Leu Ile Gln Pro Gly Leu Trp Thr Arg Asp
 1               5                  10                  15

Thr Ser Trp Thr Leu Leu Tyr Phe Leu Cys Tyr Ile Leu Pro Gln Thr
             20                  25                  30

Ser Pro Gln Val Leu Arg Ile Gly Gly Ile Phe Glu Thr Val Glu Asn
         35                  40                  45

Glu Pro Val Asn Val Glu Glu Leu Ala Phe Lys Phe Ala Val Thr Ser
     50                  55                  60
```

-continued

```
Ile Asn Arg Asn Arg Thr Leu Met Pro Asn Thr Thr Leu Thr Tyr Asp
 65                  70                  75                  80

Ile Gln Arg Ile Asn Leu Phe Asp Ser Phe Glu Ala Ser Arg Arg Ala
                 85                  90                  95

Cys Asp Gln Leu Ala Leu Gly Val Ala Leu Phe Gly Pro Ser His
                100                 105                 110

Ser Ser Ser Val Ser Ala Val Gln Ser Ile Cys Asn Ala Leu Glu Val
            115                 120                 125

Pro His Ile Gln Thr Arg Trp Lys His Pro Ser Val Asp Ser Arg Asp
        130                 135                 140

Leu Phe Tyr Ile Asn Leu Tyr Pro Asp Tyr Ala Ala Ile Ser Arg Ala
145                 150                 155                 160

Val Leu Asp Leu Val Leu Tyr Tyr Asn Trp Lys Thr Val Thr Val Val
                165                 170                 175

Tyr Glu Asp Ser Thr Gly Leu Ile Arg Leu Gln Glu Leu Ile Lys Ala
            180                 185                 190

Pro Ser Arg Tyr Asn Ile Lys Ile Lys Ile Arg Gln Leu Pro Pro Ala
        195                 200                 205

Asn Lys Asp Ala Lys Pro Leu Leu Lys Glu Met Lys Lys Ser Lys Glu
210                 215                 220

Phe Tyr Val Ile Phe Asp Cys Ser His Glu Thr Ala Ala Glu Ile Leu
225                 230                 235                 240

Lys Gln Ile Leu Phe Met Gly Met Met Thr Glu Tyr Tyr His Tyr Phe
                245                 250                 255

Phe Thr Thr Leu Asp Leu Phe Ala Leu Asp Leu Glu Leu Tyr Arg Tyr
            260                 265                 270

Ser Gly Val Asn Met Thr Gly Phe Arg Leu Leu Asn Ile Asp Asn Pro
        275                 280                 285

His Val Ser Ser Ile Ile Glu Lys Trp Ser Met Glu Arg Leu Gln Ala
        290                 295                 300

Pro Pro Arg Pro Glu Thr Gly Leu Leu Asp Gly Met Met Thr Thr Glu
305                 310                 315                 320

Ala Ala Leu Met Tyr Asp Ala Val Tyr Met Val Ala Ile Ala Ser His
                325                 330                 335

Arg Ala Ser Gln Leu Thr Val Ser Ser Leu Gln Cys His Arg His Lys
            340                 345                 350

Pro Trp Arg Leu Gly Pro Arg Phe Met Asn Leu Ile Lys Glu Ala Arg
        355                 360                 365

Trp Asp Gly Leu Thr Gly Arg Ile Thr Phe Asn Lys Thr Asp Gly Leu
370                 375                 380

Arg Lys Asp Phe Asp Leu Asp Ile Ile Ser Leu Lys Glu Glu Gly Thr
385                 390                 395                 400

Glu Lys Ala Ser Gly Glu Val Ser Lys His Leu Tyr Lys Val Trp Lys
                405                 410                 415

Lys Ile Gly Ile Trp Asn Ser Asn Ser Gly Leu Asn Met Thr Asp Gly
            420                 425                 430

Asn Arg Asp Arg Ser Asn Asn Ile Thr Asp Ser Leu Ala Asn Arg Thr
        435                 440                 445

Leu Ile Val Thr Thr Ile Leu Glu Glu Pro Tyr Val Met Tyr Arg Lys
450                 455                 460

Ser Asp Lys Pro Leu Tyr Gly Asn Asp Arg Phe Glu Gly Tyr Cys Leu
465                 470                 475                 480

Asp Leu Leu Lys Glu Leu Ser Asn Ile Leu Gly Phe Leu Tyr Asp Val
```

-continued

```
                485                 490                 495
Lys Leu Val Pro Asp Gly Lys Tyr Gly Ala Gln Asn Asp Lys Gly Glu
                500                 505                 510

Trp Asn Gly Met Val Lys Glu Leu Ile Asp His Arg Ala Asp Leu Ala
                515                 520                 525

Val Ala Pro Leu Thr Ile Thr Tyr Val Arg Glu Lys Val Ile Asp Phe
            530                 535                 540

Ser Lys Pro Phe Met Thr Leu Gly Ile Ser Ile Leu Tyr Arg Lys Pro
545                 550                 555                 560

Asn Gly Thr Asn Pro Gly Val Phe Ser Phe Leu Asn Pro Leu Ser Pro
                565                 570                 575

Asp Ile Trp Met Tyr Val Leu Leu Ala Cys Leu Gly Val Ser Cys Val
                580                 585                 590

Leu Phe Val Ile Ala Arg Phe Thr Pro Tyr Glu Trp Tyr Asn Pro His
            595                 600                 605

Pro Cys Asn Pro Asp Ser Asp Val Val Glu Asn Asn Phe Thr Leu Leu
        610                 615                 620

Asn Ser Phe Trp Phe Gly Val Gly Ala Leu Met Gln Gln Gly Ser Glu
625                 630                 635                 640

Leu Met Pro Lys Ala Leu Ser Thr Arg Ile Val Gly Gly Ile Trp Trp
                645                 650                 655

Phe Phe Thr Leu Ile Ile Ile Ser Ser Tyr Thr Ala Asn Leu Ala Ala
            660                 665                 670

Phe Leu Thr Val Glu Arg Met Glu Ser Pro Ile Asp Ser Ala Asp Asp
            675                 680                 685

Leu Ala Lys Gln Thr Lys Ile Glu Tyr Gly Ala Val Arg Asp Gly Ser
        690                 695                 700

Thr Met Thr Phe Phe Lys Lys Ser Lys Ile Ser Thr Tyr Glu Lys Met
705                 710                 715                 720

Trp Ala Phe Met Ser Ser Arg Gln Gln Ser Ala Leu Val Lys Asn Ser
                725                 730                 735

Asp Glu Gly Ile Gln Arg Val Leu Thr Thr Asp Tyr Ala Leu Leu Met
            740                 745                 750

Glu Ser Thr Ser Ile Glu Tyr Val Thr Gln Arg Asn Cys Asn Leu Thr
        755                 760                 765

Gln Ile Gly Gly Leu Ile Asp Ser Lys Gly Tyr Gly Val Gly Thr Pro
        770                 775                 780

Ile Gly Ser Pro Tyr Arg Asp Lys Ile Thr Ile Ala Ile Leu Gln Leu
785                 790                 795                 800

Gln Glu Glu Gly Lys Leu His Met Met Lys Glu Lys Trp Trp Arg Gly
                805                 810                 815

Asn Gly Cys Pro Glu Glu Asp Ser Lys Glu Ala Ser Ala Leu Gly Val
                820                 825                 830

Glu Asn Ile Gly Gly Ile Phe Ile Val Leu Ala Ala Gly Leu Val Leu
            835                 840                 845

Ser Val Phe Val Ala Ile Gly Glu Phe Leu Tyr Lys Ser Arg Lys Asn
        850                 855                 860

Asn Asp Val Glu Gln Cys Leu Ser Phe Asn Ala Ile Met Glu Glu Leu
865                 870                 875                 880

Gly Ile Ser Leu Lys Asn Gln Lys Lys Leu Lys Lys Ser Arg Thr
                885                 890                 895

Lys Gly Lys Ser Ser Phe Thr Ser Ile Leu Thr Cys His Gln Arg Arg
            900                 905                 910
```

Thr Gln Arg Lys Glu Thr Val Ala
        915                 920

(2) INFORMATION FOR SEQ ID NO:11:

(i) SEQUENCE CHARACTERISTICS:
        (A) LENGTH: 4608 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: GluR6

(ix) FEATURE:
        (A) NAME/KEY: Coding Sequence
        (B) LOCATION: 307...2958
        (D) OTHER INFORMATION:

(xi) SEQUENCE DESCRIPTION: SEQ ID NO:11:

```
GAATTCGGGC TCGCAAGGGC TTCGCAGGCT GGACATTGTG CTTGCTGGAT TTTTCCCGGA      60

TGCTCCCGGA CTAACATGGA TGTCCCACCA TCCCTTGCAG TGGAAGCTTG CTCCTTGGCG     120

CAGTGAGAGT GAAGAACATG CAGCGACTGC TAATGGGTTT GGGAAGCGGA GACTCCTTCC     180

TCTTTCTGTG ACCATGCCGT GATTGTGTCT GCGGCCACTA CTCCACGCAT CTTCCTTCTC     240

GTCCAAGCCC GGAGCCTAAC GCTAGATCGG GGAAGTGGGT GCCGCGCGCG CAGGCACGGA     300
```

AACATC ATG AAG ATT ATT TCC CCA GTT TTA AGT AAT CTA GTC TTC AGT        348
       Met Lys Ile Ile Ser Pro Val Leu Ser Asn Leu Val Phe Ser
         1               5                  10

CGC TCC ATT AAA GTC CTG CTC TGC TTA TTG TGG ATC GGA TAT TCG CAA       396
Arg Ser Ile Lys Val Leu Leu Cys Leu Leu Trp Ile Gly Tyr Ser Gln
 15              20                  25                  30

GGA ACC ACA CAT GTG TTA AGA TTC GGT GGT ATA TTT GAA TAT GTG GAA       444
Gly Thr Thr His Val Leu Arg Phe Gly Gly Ile Phe Glu Tyr Val Glu
                 35                  40                  45

TCT GGC CCC ATG GGA GCA GAA GAA CTT GCA TTC AGA TTT GCT GTG AAT       492
Ser Gly Pro Met Gly Ala Glu Glu Leu Ala Phe Arg Phe Ala Val Asn
             50                  55                  60

ACC ATC AAC AGA AAC AGG ACT TTG CTG CCC AAC ACC ACT TTA ACT TAT       540
Thr Ile Asn Arg Asn Arg Thr Leu Leu Pro Asn Thr Thr Leu Thr Tyr
 65                  70                  75

GAT ACT CAG AAG ATC AAT CTC TAT GAC AGT TTT GAA GCA TCT AAG AAA       588
Asp Thr Gln Lys Ile Asn Leu Tyr Asp Ser Phe Glu Ala Ser Lys Lys
 80                  85                  90

GCT TGT GAT CAG CTG TCT CTT GGG GTG GCT GCT ATC TTC GGT CCT TCA       636
Ala Cys Asp Gln Leu Ser Leu Gly Val Ala Ala Ile Phe Gly Pro Ser
 95                 100                 105                 110

CAC AGT TCA TCA GCC AAT GCT GTG CAG TCC ATC TGC AAT GCT CTG GGG       684
His Ser Ser Ser Ala Asn Ala Val Gln Ser Ile Cys Asn Ala Leu Gly
                 115                 120                 125

GTT CCC CAC ATA CAG ACC CGC TGG AAG CAC CAG GTG TCA GAC AAC AAG       732
Val Pro His Ile Gln Thr Arg Trp Lys His Gln Val Ser Asp Asn Lys
             130                 135                 140

GAT TCC TTC TAC GTC AGT CTC TAC CCA GAC TTC TCT TCC CTG AGC CGC       780
Asp Ser Phe Tyr Val Ser Leu Tyr Pro Asp Phe Ser Ser Leu Ser Arg
145                 150                 155

GCC ATC TTG GAT TTG GTG CAG TTT TTT AAG TGG AAA ACT GTC ACA GTT       828
Ala Ile Leu Asp Leu Val Gln Phe Phe Lys Trp Lys Thr Val Thr Val
             160                 165                 170

GTG TAT GAC GAC AGC ACT GGT CTC ATT CGC TTG CAA GAG CTC ATC AAA       876
Val Tyr Asp Asp Ser Thr Gly Leu Ile Arg Leu Gln Glu Leu Ile Lys

-continued

| | | | |
|---|---|---|---|
| 175 | 180 | 185 | 190 |

```
GCT CCA TCG AGG TAC AAT CTT CGA CTT AAA ATT CGT CAG CTG CCA GCT      924
Ala Pro Ser Arg Tyr Asn Leu Arg Leu Lys Ile Arg Gln Leu Pro Ala
            195             200             205

GAT ACC AAA GAT GCA AAA CCT TTG CTG AAG GAG ATG AAA AGA GGC AAG      972
Asp Thr Lys Asp Ala Lys Pro Leu Leu Lys Glu Met Lys Arg Gly Lys
            210             215             220

GAG TTC CAC GTG ATC TTC GAC TGC AGC CAT GAG ATG GCA GCA GGC ATT     1020
Glu Phe His Val Ile Phe Asp Cys Ser His Glu Met Ala Ala Gly Ile
            225             230             235

TTA AAA CAG GCA TTA GCT ATG GGA ATG ATG ACA GAA TAC TAT CAC TAT     1068
Leu Lys Gln Ala Leu Ala Met Gly Met Met Thr Glu Tyr Tyr His Tyr
    240             245             250

ATA TTT ACA ACT CTG GAC CTC TTT GCT CTT GAC GTG GAG CCC TAC AGA     1116
Ile Phe Thr Thr Leu Asp Leu Phe Ala Leu Asp Val Glu Pro Tyr Arg
255             260             265             270

TAC AGT GGC GTA AAT ATG ACA GGG TTC AGG ATA CTA AAT ACA GAG AAT     1164
Tyr Ser Gly Val Asn Met Thr Gly Phe Arg Ile Leu Asn Thr Glu Asn
                275             280             285

ACC CAA GTC TCC TCC ATC ATC GAA AAG TGG TCT ATG GAA CGG TTA CAG     1212
Thr Gln Val Ser Ser Ile Ile Glu Lys Trp Ser Met Glu Arg Leu Gln
            290             295             300

GCG CCT CCA AAA CCT GAC TCA GGT TTG CTG GAT GGA TTT ATG ACG ACT     1260
Ala Pro Pro Lys Pro Asp Ser Gly Leu Leu Asp Gly Phe Met Thr Thr
            305             310             315

GAT GCT GCT CTG ATG TAT GAT GCA GTG CAC GTT GTG TCT GTG GCT GTC     1308
Asp Ala Ala Leu Met Tyr Asp Ala Val His Val Val Ser Val Ala Val
            320             325             330

CAA CAG TTT CCC CAG ATG ACA GTC AGC TCC TTG CAA TGC AAT CGA CAC     1356
Gln Gln Phe Pro Gln Met Thr Val Ser Ser Leu Gln Cys Asn Arg His
335             340             345             350

AAA CCC TGG CGC TTT GGG ACC CGC TTC ATG AGT CTA ATT AAA GAG GCT     1404
Lys Pro Trp Arg Phe Gly Thr Arg Phe Met Ser Leu Ile Lys Glu Ala
                355             360             365

CAC TGG GAA GGT CTC ACA GGC AGA ATA ACA TTT AAC AAA ACC AAT GGA     1452
His Trp Glu Gly Leu Thr Gly Arg Ile Thr Phe Asn Lys Thr Asn Gly
            370             375             380

TTA CGG ACA GAT TTT GAT TTG GAT GTG ATC AGT CTC AAG GAA GAA GGT     1500
Leu Arg Thr Asp Phe Asp Leu Asp Val Ile Ser Leu Lys Glu Glu Gly
            385             390             395

CTG GAG AAG ATT GGA ACT TGG GAT CCA GCC AGT GGC CTG AAT ATG ACA     1548
Leu Glu Lys Ile Gly Thr Trp Asp Pro Ala Ser Gly Leu Asn Met Thr
            400             405             410

GAA AGT CAG AAA GGA AAG CCA GCA AAT ATC ACA GAC TCA TTG TCT AAT     1596
Glu Ser Gln Lys Gly Lys Pro Ala Asn Ile Thr Asp Ser Leu Ser Asn
415             420             425             430

CGT TCT TTG ATT GTT ACC ACC ATT TTG GAA GAA CCG TAT GTT CTG TTT     1644
Arg Ser Leu Ile Val Thr Thr Ile Leu Glu Glu Pro Tyr Val Leu Phe
                435             440             445

AAG AAG TCT GAC AAA CCA CTC TAT GGG AAT GAT CGA TTT GAA GGC TAC     1692
Lys Lys Ser Asp Lys Pro Leu Tyr Gly Asn Asp Arg Phe Glu Gly Tyr
            450             455             460

TGT ATT GAT CTC CTA CGA GAG TTA TCT ACA ATC CTT GGC TTT ACA TAT     1740
Cys Ile Asp Leu Leu Arg Glu Leu Ser Thr Ile Leu Gly Phe Thr Tyr
            465             470             475

GAG ATT AGG CTT GTG GAG GAT GGG AAA TAT GGA GCC CAG GAT GAT GTG     1788
Glu Ile Arg Leu Val Glu Asp Gly Lys Tyr Gly Ala Gln Asp Asp Val
            480             485             490

AAC GGA CAA TGG AAT GGA ATG GTT CGT GAA CTA ATC GAT CAT AAA GCT     1836
Asn Gly Gln Trp Asn Gly Met Val Arg Glu Leu Ile Asp His Lys Ala
```

-continued

```
    495                 500                 505                 510
GAC CTT GCA GTT GCT CCA CTG GCT ATA ACC TAT GTT CGT GAG AAG GTC     1884
Asp Leu Ala Val Ala Pro Leu Ala Ile Thr Tyr Val Arg Glu Lys Val
                515                 520                 525

ATC GAC TTT TCA AAG CCG TTT ATG ACA CTT GGA ATA AGT ATT TTG TAC     1932
Ile Asp Phe Ser Lys Pro Phe Met Thr Leu Gly Ile Ser Ile Leu Tyr
                530                 535                 540

CGC AAG CCC AAT GGT ACA AAC CCA GGC GTC TTC TCC TTC CTG AAT CCT     1980
Arg Lys Pro Asn Gly Thr Asn Pro Gly Val Phe Ser Phe Leu Asn Pro
                545                 550                 555

CTC TCC CCT GAT ATC TGG ATG TAT GTT CTG CTG GCT TGC TTG GGT GTC     2028
Leu Ser Pro Asp Ile Trp Met Tyr Val Leu Leu Ala Cys Leu Gly Val
                560                 565                 570

AGT TGT GTG CTC TTT GTC ATA GCC AGG TTT AGT CCC TAT GAG TGG TAT     2076
Ser Cys Val Leu Phe Val Ile Ala Arg Phe Ser Pro Tyr Glu Trp Tyr
575                 580                 585                 590

AAC CCA CAC CCT TGC AAC CCT GAC TCA GAC GTG GTG GAA AAC AAT TTT     2124
Asn Pro His Pro Cys Asn Pro Asp Ser Asp Val Val Glu Asn Asn Phe
                595                 600                 605

ACC TTG CTA AAT AGT TTC TGG TTT GGA GTT GGA GCT CTC ATG CGG CAA     2172
Thr Leu Leu Asn Ser Phe Trp Phe Gly Val Gly Ala Leu Met Arg Gln
                610                 615                 620

GGT TCT GAG CTC ATG CCC AAA GCA CTC TCC ACC AGG ATA GTG GGA GGC     2220
Gly Ser Glu Leu Met Pro Lys Ala Leu Ser Thr Arg Ile Val Gly Gly
                625                 630                 635

ATT TGG TGG TTT TTC ACA CTT ATC ATC ATT TCT TCG TAT ACC GCT AAC     2268
Ile Trp Trp Phe Phe Thr Leu Ile Ile Ile Ser Ser Tyr Thr Ala Asn
                640                 645                 650

CTA GCC GCC TTT CTG ACT GTG GAA CGC ATG GAG TCG CCC ATT GAC TCT     2316
Leu Ala Ala Phe Leu Thr Val Glu Arg Met Glu Ser Pro Ile Asp Ser
655                 660                 665                 670

GCT GAC GAT TTA GCT AAG CAA ACC AAG ATA GAG TAT GGA GCA GTG GAG     2364
Ala Asp Asp Leu Ala Lys Gln Thr Lys Ile Glu Tyr Gly Ala Val Glu
                675                 680                 685

GAC GGC GCA ACC ATG ACG TTT TTT AAG AAA TCA AAA ATT TCA ACG TAT     2412
Asp Gly Ala Thr Met Thr Phe Phe Lys Lys Ser Lys Ile Ser Thr Tyr
                690                 695                 700

GAT AAA ATG TGG GCG TTT ATG AGC AGC AGG AGA CAG TCT GTG CTT GTC     2460
Asp Lys Met Trp Ala Phe Met Ser Ser Arg Arg Gln Ser Val Leu Val
                705                 710                 715

AAA AGC AAT GAG GAA GGG ATC CAA CGA GTC CTC ACC TCG GAT TAT GCT     2508
Lys Ser Asn Glu Glu Gly Ile Gln Arg Val Leu Thr Ser Asp Tyr Ala
                720                 725                 730

TTC TTA ATG GAG TCA ACA ACC ATC GAG TTT GTT ACA CAG CGG AAC TGT     2556
Phe Leu Met Glu Ser Thr Thr Ile Glu Phe Val Thr Gln Arg Asn Cys
735                 740                 745                 750

AAC CTC ACG CAG ATT GGC GGC CTT ATA GAC TCC AAA GGC TAT GGC GTT     2604
Asn Leu Thr Gln Ile Gly Gly Leu Ile Asp Ser Lys Gly Tyr Gly Val
                755                 760                 765

GGC ACT CCT ATG GGC TCT CCA TAT CGA GAC AAA ATC ACC ATA GCA ATT     2652
Gly Thr Pro Met Gly Ser Pro Tyr Arg Asp Lys Ile Thr Ile Ala Ile
                770                 775                 780

CTT CAG CTG CAG GAG GAA GGC AAG CTG CAC ATG ATG AAG GAG AAA TGG     2700
Leu Gln Leu Gln Glu Glu Gly Lys Leu His Met Met Lys Glu Lys Trp
                785                 790                 795

TGG CGG GGC AAT GGC TGC CCA GAG GAG GAG AGC AAA GAG GCC AGT GCT     2748
Trp Arg Gly Asn Gly Cys Pro Glu Glu Glu Ser Lys Glu Ala Ser Ala
                800                 805                 810

CTG GGG GTG CAG AAT ATT GGT GGT ATC TTC ATT GTC CTG GCA GCC GGC     2796
Leu Gly Val Gln Asn Ile Gly Gly Ile Phe Ile Val Leu Ala Ala Gly
```

-continued

```
            815                 820                 825                 830
TTG GTG CTC TCA GTT TTT GTG GCA GTG GGA GAG TTT TTA TAC AAA TCC            2844
Leu Val Leu Ser Val Phe Val Ala Val Gly Glu Phe Leu Tyr Lys Ser
                        835                 840                 845

AAA AAA AAC GCT CAA TTG GAA AAG AGG TCC TTC TGT AGC GCT ATG GTG            2892
Lys Lys Asn Ala Gln Leu Glu Lys Arg Ser Phe Cys Ser Ala Met Val
                850                 855                 860

GAA GAG CTG AGA ATG TCC CTG AAG TGC CAG CGT CGG CTC AAA CAT AAG            2940
Glu Glu Leu Arg Met Ser Leu Lys Cys Gln Arg Arg Leu Lys His Lys
            865                 870                 875

CCA CAG CCC CAG TTA TTG TGAAAACAGA AGAAGTTATC AACATGCACA CATTTAAC          2996
Pro Gln Pro Gln Leu Leu
        880

GACAGAAGGT TGCCAGGTAA AGAAACCATG GCATGAAGCT GGGAGGCCAA TCACCCAAGC          3056

ACAAACTGTC GTCTTTTTTT TTTTTTTTTC CAAACAATTT AGCGAGAATG TTTCCTGTGG          3116

AAATATGCAA CCTGTGCAAA ATAAAATGAG TTACCTCATG CCGCTGTGTC TATGAACTAG          3176

AGACTCTGTG ATCTAAGCAG TTTCAGTGAT CAGACTTGAT TTACAAGCAC CGTGGATCAA          3236

CCAAGTTACA CGGGGTTACA CTGTTTATCA TAGGTTCCTC CCTTCCTTTG AGTGAATGTT          3296

ACATGCAAAT GTTGTGGCTG GTTTCAAATG CAGTCCAGGG AGAAACTGCT GGTTCCTTCT          3356

GAAGCTCAGC TGTCGTCAGG AGATGGAATG CCGGTGCCCA AAAGGGTAAC CAATAAAAAT          3416

GCCATAAAAA TTTTAAAAAA ATGCGTGAGA TCGGCAAAAA TTATAGTGTT ACAAGAAACA          3476

GTACAGTCCC ATGGTCACCA ACACAATAGA GGTGATAATG TTACTAGCCC CCAATACTCA          3536

GTAAAATCGT CATCTGAATA GATAATATGT GTTCATAGAA TGTGAAAAAA AATGTAATGC          3596

GAGACACACC AGTATCAATA GAAGTGGAAC TGAAGGCAGA ACATCATCAG TTACTTTTCT          3656

TTTTCAATAG TCTGTGTCAT GGATTGTGAT ATAGATGGCA ATTATCAAGC CAATAATTTT          3716

TTTTCTGAAA ATACCTATGG CAAATATTTT AATAGGCAAC TTGCTCCCAC AAATCCCTAC          3776

TCTAACCTCC CCCAGAAATA TAAAAGGAAC CATTGGTTTA GAGATTGGTA TGTAAGAGAT          3836

GATGTTTTGC AAGCCTTGTC GTGCATTGTA AAAGGGCTCA GTGTTACTGG TTACAGGGAA          3896

GACTGAAGCT TTCACCCTGA CATTCTGAAA TGTCAACCGA AACTCTCCTT CCTCCTGTAA          3956

AGGACCTTGA TGGGGCAGAT TCCATTGATC AAAGAATGGG GACTTGTCAC CTATACAATG          4016

GTACGTGACA GAACTTTGAG GTGGACTGCA TTTAATAATA GTCACAATGT TAAAAGAACA          4076

AAATTCTTGA GCAGTTTTTT TTTTTTGTTT TGTTTTGTTT TCAAAAAATG TTCAGGTTTA          4136

TTTGTGGAAA TGCAAGATTT CTATAAAATA GTTTTTGTAT GGAAATTTTT GTAATACTTT          4196

TTATCAACAA AATAAGAACA CATGTTTCTG TCAGGGGTGT GAGGTCAAGC ATGAACGGTA          4256

GTGCGTGTGC ACCACCAACG TTTGGTGAAA CTATTTTTAT CAAGAAAAAG GAATCATAGA          4316

AGAGAAATAT TTTCAAGTTA GATACTATAA AAGCTAGGTG CACTACCACC ACGGCTTGTC          4376

GCGCCACACC CCTGAGTCCA CAAGGTGGAT AACATATTGT AATGAACAGT TGTGTGTAAA          4436

ATGGCAAAAG ACACAGACCT CTTGACAACA TTGTGAAAAC AGTTGAGTGC ACACAGTTTG          4496

CTGTTTGAAT CCAATGCACA AAAATTTTAC AAAAATCCAT TAAAATTATG TCCGTTTTAA          4556

AACCTGCAGC CCGGGGGATC CACTAGTTCT AGAGCCGGTG CCCAATTCGC CC                 4608
```

(2) INFORMATION FOR SEQ ID NO:12:

(i) SEQUENCE CHARACTERISTICS:
        (A) LENGTH: 884 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Met Lys Ile Ile Ser Pro Val Leu Ser Asn Leu Val Phe Ser Arg Ser
 1               5                  10                  15

Ile Lys Val Leu Leu Cys Leu Leu Trp Ile Gly Tyr Ser Gln Gly Thr
            20                  25                  30

Thr His Val Leu Arg Phe Gly Gly Ile Phe Glu Tyr Val Glu Ser Gly
        35                  40                  45

Pro Met Gly Ala Glu Glu Leu Ala Phe Arg Phe Ala Val Asn Thr Ile
    50                  55                  60

Asn Arg Asn Arg Thr Leu Leu Pro Asn Thr Thr Leu Thr Tyr Asp Thr
65                  70                  75                  80

Gln Lys Ile Asn Leu Tyr Asp Ser Phe Glu Ala Ser Lys Lys Ala Cys
                85                  90                  95

Asp Gln Leu Ser Leu Gly Val Ala Ala Ile Phe Gly Pro Ser His Ser
            100                 105                 110

Ser Ser Ala Asn Ala Val Gln Ser Ile Cys Asn Ala Leu Gly Val Pro
        115                 120                 125

His Ile Gln Thr Arg Trp Lys His Gln Val Ser Asp Asn Lys Asp Ser
    130                 135                 140

Phe Tyr Val Ser Leu Tyr Pro Asp Phe Ser Ser Leu Ser Arg Ala Ile
145                 150                 155                 160

Leu Asp Leu Val Gln Phe Phe Lys Trp Lys Thr Val Thr Val Val Tyr
                165                 170                 175

Asp Asp Ser Thr Gly Leu Ile Arg Leu Gln Glu Leu Ile Lys Ala Pro
            180                 185                 190

Ser Arg Tyr Asn Leu Arg Leu Lys Ile Arg Gln Leu Pro Ala Asp Thr
        195                 200                 205

Lys Asp Ala Lys Pro Leu Leu Lys Glu Met Lys Arg Gly Lys Glu Phe
    210                 215                 220

His Val Ile Phe Asp Cys Ser His Glu Met Ala Ala Gly Ile Leu Lys
225                 230                 235                 240

Gln Ala Leu Ala Met Gly Met Met Thr Glu Tyr Tyr His Tyr Ile Phe
                245                 250                 255

Thr Thr Leu Asp Leu Phe Ala Leu Asp Val Glu Pro Tyr Arg Tyr Ser
            260                 265                 270

Gly Val Asn Met Thr Gly Phe Arg Ile Leu Asn Thr Glu Asn Thr Gln
        275                 280                 285

Val Ser Ser Ile Ile Glu Lys Trp Ser Met Glu Arg Leu Gln Ala Pro
    290                 295                 300

Pro Lys Pro Asp Ser Gly Leu Leu Asp Gly Phe Met Thr Thr Asp Ala
305                 310                 315                 320

Ala Leu Met Tyr Asp Ala Val His Val Val Ser Val Ala Val Gln Gln
                325                 330                 335

Phe Pro Gln Met Thr Val Ser Ser Leu Gln Cys Asn Arg His Lys Pro
            340                 345                 350

Trp Arg Phe Gly Thr Arg Phe Met Ser Leu Ile Lys Glu Ala His Trp
        355                 360                 365

Glu Gly Leu Thr Gly Arg Ile Thr Phe Asn Lys Thr Asn Gly Leu Arg
    370                 375                 380

Thr Asp Phe Asp Leu Asp Val Ile Ser Leu Lys Glu Glu Gly Leu Glu
385                 390                 395                 400
```

```
Lys Ile Gly Thr Trp Asp Pro Ala Ser Gly Leu Asn Met Thr Glu Ser
            405                 410                 415

Gln Lys Gly Lys Pro Ala Asn Ile Thr Asp Ser Leu Ser Asn Arg Ser
        420                 425                 430

Leu Ile Val Thr Thr Ile Leu Glu Pro Tyr Val Leu Phe Lys Lys
        435                 440                 445

Ser Asp Lys Pro Leu Tyr Gly Asn Asp Arg Phe Glu Gly Tyr Cys Ile
        450                 455                 460

Asp Leu Leu Arg Glu Leu Ser Thr Ile Leu Gly Phe Thr Tyr Glu Ile
465                 470                 475                 480

Arg Leu Val Glu Asp Gly Lys Tyr Gly Ala Gln Asp Val Asn Gly
                485                 490                 495

Gln Trp Asn Gly Met Val Arg Glu Leu Ile Asp His Lys Ala Asp Leu
            500                 505                 510

Ala Val Ala Pro Leu Ala Ile Thr Tyr Val Arg Glu Lys Val Ile Asp
        515                 520                 525

Phe Ser Lys Pro Phe Met Thr Leu Gly Ile Ser Ile Leu Tyr Arg Lys
        530                 535                 540

Pro Asn Gly Thr Asn Pro Gly Val Phe Ser Phe Leu Asn Pro Leu Ser
545                 550                 555                 560

Pro Asp Ile Trp Met Tyr Val Leu Leu Ala Cys Leu Gly Val Ser Cys
                565                 570                 575

Val Leu Phe Val Ile Ala Arg Phe Ser Pro Tyr Glu Trp Tyr Asn Pro
            580                 585                 590

His Pro Cys Asn Pro Asp Ser Asp Val Val Glu Asn Asn Phe Thr Leu
        595                 600                 605

Leu Asn Ser Phe Trp Phe Gly Val Gly Ala Leu Met Arg Gln Gly Ser
        610                 615                 620

Glu Leu Met Pro Lys Ala Leu Ser Thr Arg Ile Val Gly Gly Ile Trp
625                 630                 635                 640

Trp Phe Phe Thr Leu Ile Ile Ile Ser Ser Tyr Thr Ala Asn Leu Ala
                645                 650                 655

Ala Phe Leu Thr Val Glu Arg Met Glu Ser Pro Ile Asp Ser Ala Asp
            660                 665                 670

Asp Leu Ala Lys Gln Thr Lys Ile Glu Tyr Gly Ala Val Glu Asp Gly
        675                 680                 685

Ala Thr Met Thr Phe Phe Lys Lys Ser Lys Ile Ser Thr Tyr Asp Lys
        690                 695                 700

Met Trp Ala Phe Met Ser Ser Arg Arg Gln Ser Val Leu Val Lys Ser
705                 710                 715                 720

Asn Glu Glu Gly Ile Gln Arg Val Leu Thr Ser Asp Tyr Ala Phe Leu
                725                 730                 735

Met Glu Ser Thr Thr Ile Glu Phe Val Thr Gln Arg Asn Cys Asn Leu
            740                 745                 750

Thr Gln Ile Gly Gly Leu Ile Asp Ser Lys Gly Tyr Gly Val Gly Thr
        755                 760                 765

Pro Met Gly Ser Pro Tyr Arg Asp Lys Ile Thr Ile Ala Ile Leu Gln
        770                 775                 780

Leu Gln Glu Glu Gly Lys Leu His Met Met Lys Glu Lys Trp Trp Arg
785                 790                 795                 800

Gly Asn Gly Cys Pro Glu Glu Glu Ser Lys Glu Ala Ser Ala Leu Gly
                805                 810                 815

Val Gln Asn Ile Gly Gly Ile Phe Ile Val Leu Ala Ala Gly Leu Val
            820                 825                 830
```

```
Leu Ser Val Phe Val Ala Val Gly Glu Phe Leu Tyr Lys Ser Lys Lys
        835                 840                 845

Asn Ala Gln Leu Glu Lys Arg Ser Phe Cys Ser Ala Met Val Glu Glu
    850                 855                 860

Leu Arg Met Ser Leu Lys Cys Gln Arg Arg Leu Lys His Lys Pro Gln
865                 870                 875                 880

Pro Gln Leu Leu
```

(2) INFORMATION FOR SEQ ID NO:13:

(i) SEQUENCE CHARACTERISTICS:
        (A) LENGTH: 3344 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: GluR7

(ix) FEATURE:
        (A) NAME/KEY: Coding Sequence
        (B) LOCATION: 1...2763
        (D) OTHER INFORMATION:

(xi) SEQUENCE DESCRIPTION: SEQ ID NO:13:

```
GGG GCC GTG GCG GGC TCC CTG GGG CGC CTC CGG AGT CTG GTT TGG GAA    48
Gly Ala Val Ala Gly Ser Leu Gly Arg Leu Arg Ser Leu Val Trp Glu
1               5                   10                  15

TAC TGG GCC GGG TTC CTC GTG TGC GCC TTC TGG ATC CCA GAC TCG CGC    96
Tyr Trp Ala Gly Phe Leu Val Cys Ala Phe Trp Ile Pro Asp Ser Arg
                20                  25                  30

GGG ATG CCC CAC GTC ATC CGG ATC GGC GGA ATC TTT GAG TAC GCG GAC   144
Gly Met Pro His Val Ile Arg Ile Gly Gly Ile Phe Glu Tyr Ala Asp
            35                  40                  45

GGC CCC AAC GCC CAG GTC ATG AAC GCT GAG GAG CAC GCC TTT CGG TTT   192
Gly Pro Asn Ala Gln Val Met Asn Ala Glu Glu His Ala Phe Arg Phe
        50                  55                  60

TCT GCC AAT ATC ATC AAC AGG AAC AGA ACT CTG CTG CCC AAC ACG ACC   240
Ser Ala Asn Ile Ile Asn Arg Asn Arg Thr Leu Leu Pro Asn Thr Thr
65                  70                  75                  80

CTG ACC TAC GAC ATT CAG AGG ATT CAC TTC CAT GAC AGT TTT GAG GCC   288
Leu Thr Tyr Asp Ile Gln Arg Ile His Phe His Asp Ser Phe Glu Ala
                85                  90                  95

ACC AAG AAG GCC TGT GAC CAG TTG GCG CTC GGT GTG GTA GCC ATC TTT   336
Thr Lys Lys Ala Cys Asp Gln Leu Ala Leu Gly Val Val Ala Ile Phe
                100                 105                 110

GGG CCA TCC CAG GGC TCC TGC ATC AAT GCC GTC CAG TCC ATC TGC AAT   384
Gly Pro Ser Gln Gly Ser Cys Ile Asn Ala Val Gln Ser Ile Cys Asn
            115                 120                 125

GCC TTG GAG GTT CCT CAC ATC CAA CTG CGC TGG AAG CAC CAC CCC CTG   432
Ala Leu Glu Val Pro His Ile Gln Leu Arg Trp Lys His His Pro Leu
        130                 135                 140

GAC AAC AAG GAC ACC TTC TAC GTG AAC CTC TAC CCC GAC TAC GCC TCT   480
Asp Asn Lys Asp Thr Phe Tyr Val Asn Leu Tyr Pro Asp Tyr Ala Ser
145                 150                 155                 160

CTC AGC CAC GCC ATC CTC GAC TTG GTC CAG TCC CTC AAG TGG CGG TCA   528
Leu Ser His Ala Ile Leu Asp Leu Val Gln Ser Leu Lys Trp Arg Ser
                165                 170                 175

GCC ACC GTA GTC TAT GAT GAC AGT ACA GGT CTC ATC CGG CTG CAG GAG   576
Ala Thr Val Val Tyr Asp Asp Ser Thr Gly Leu Ile Arg Leu Gln Glu
                180                 185                 190
```

```
CTC ATC ATG GCT CCA TCT AGG TAC AAC ATC CGC CTG AAG ATT CGC CAG        624
Leu Ile Met Ala Pro Ser Arg Tyr Asn Ile Arg Leu Lys Ile Arg Gln
        195                 200                 205

CTC CCC ATC GAC TCC GAT GAC TCA CGC CCC TTG CTC AAA GAG ATG AAG        672
Leu Pro Ile Asp Ser Asp Asp Ser Arg Pro Leu Leu Lys Glu Met Lys
210                 215                 220

CGG GGC CGG GAG TTC CGT ATC ATC TTT GAC TGC AGT CAC ACC ATG GCA        720
Arg Gly Arg Glu Phe Arg Ile Ile Phe Asp Cys Ser His Thr Met Ala
225                 230                 235                 240

GCC CAG ATC CTC AAG CAG GCC ATG GCC ATG GGC ATG ATG ACG GAA TAC        768
Ala Gln Ile Leu Lys Gln Ala Met Ala Met Gly Met Met Thr Glu Tyr
            245                 250                 255

TAC CAC TTC ATC TTC ACC ACT CTG GAT CTC TAT GCG CTA GAC CTG GAA        816
Tyr His Phe Ile Phe Thr Thr Leu Asp Leu Tyr Ala Leu Asp Leu Glu
                260                 265                 270

CCC TAC CGC TAC TCG GGA GTG AAC CTG ACT GGG TTC CGC ATA CTC AAC        864
Pro Tyr Arg Tyr Ser Gly Val Asn Leu Thr Gly Phe Arg Ile Leu Asn
            275                 280                 285

GTG GAC AAC CCC CAT GTC TCA GCC ATT GTG GAG AAG TGG TCC ATG GAG        912
Val Asp Asn Pro His Val Ser Ala Ile Val Glu Lys Trp Ser Met Glu
290                 295                 300

CGG CTA CAG GCA GCT CCC CGG GCA GAG TCA GGC CTG CTG GAT GGA GTG        960
Arg Leu Gln Ala Ala Pro Arg Ala Glu Ser Gly Leu Leu Asp Gly Val
305                 310                 315                 320

ATG ATG ACC GAT GCA GCC CTG CTC TAC GAT GCG GTC CAC ATT GTG TCT       1008
Met Met Thr Asp Ala Ala Leu Leu Tyr Asp Ala Val His Ile Val Ser
                325                 330                 335

GTG TGC TAC CAG CGA GCG CCG CAG ATG ACT GTG AAC TCC CTA CAG TGC       1056
Val Cys Tyr Gln Arg Ala Pro Gln Met Thr Val Asn Ser Leu Gln Cys
            340                 345                 350

CAT CGG CAC AAG GCC TGG CGC TTC GGT GGC CGC TTC ATG AAC TTC ATC       1104
His Arg His Lys Ala Trp Arg Phe Gly Gly Arg Phe Met Asn Phe Ile
        355                 360                 365

AAG GAG GCT CAA TGG GAA GGA TTA ACT GGA CGG ATT GTT TTC AAC AAA       1152
Lys Glu Ala Gln Trp Glu Gly Leu Thr Gly Arg Ile Val Phe Asn Lys
        370                 375                 380

ACC AGT GGC TTG CGG ACT GAT TTT GAT CTG GAC ATC ATC AGC CTC AAG       1200
Thr Ser Gly Leu Arg Thr Asp Phe Asp Leu Asp Ile Ile Ser Leu Lys
385                 390                 395                 400

GAA GAT GGC CTC GAG AAG GTC GGG GTG TGG AGT CCA GCT GAC GGT CTC       1248
Glu Asp Gly Leu Glu Lys Val Gly Val Trp Ser Pro Ala Asp Gly Leu
                405                 410                 415

AAT ATC ACT GAG GTT GCC AAA GGC CGA GGT CCT AAT GTC ACC GAC TCT       1296
Asn Ile Thr Glu Val Ala Lys Gly Arg Gly Pro Asn Val Thr Asp Ser
            420                 425                 430

CTG ACC AAC AGG TCA CTC ATC GTC ACC ACT CTG CTG GAG GAG CCT TTT       1344
Leu Thr Asn Arg Ser Leu Ile Val Thr Thr Leu Leu Glu Glu Pro Phe
        435                 440                 445

GTC ATG TTC CGC AAG TCT GAT AGG ACC CTT TAC GGC AAT GAC CGG TTC       1392
Val Met Phe Arg Lys Ser Asp Arg Thr Leu Tyr Gly Asn Asp Arg Phe
        450                 455                 460

GAG GGC TAC TGC ATC GAC TTG CTC AAG GAG CTG GCG CAC ATC CTG GGC       1440
Glu Gly Tyr Cys Ile Asp Leu Leu Lys Glu Leu Ala His Ile Leu Gly
465                 470                 475                 480

TTC TCC TAC GAG ATC CGG CTG GTG GAA GAC GGC AAG TAC GGG GCA CAG       1488
Phe Ser Tyr Glu Ile Arg Leu Val Glu Asp Gly Lys Tyr Gly Ala Gln
                485                 490                 495

GAC GAC AAG GGC CAG TGG AAC GGC ATG GTC AAG GAA CTC ATT GAC CAC       1536
Asp Asp Lys Gly Gln Trp Asn Gly Met Val Lys Glu Leu Ile Asp His
            500                 505                 510
```

```
AAA GCA GAT CTG GCT GTG GCT CCC CTG ACC ATC ACC CAT GTC CGA GAG        1584
Lys Ala Asp Leu Ala Val Ala Pro Leu Thr Ile Thr His Val Arg Glu
        515                 520                 525

AAG GCC ATT GAC TTC TCT AAG CCT TTT ATG ACC CTC GGA GTG AGC ATC        1632
Lys Ala Ile Asp Phe Ser Lys Pro Phe Met Thr Leu Gly Val Ser Ile
        530                 535                 540

TTA TAT CGA AAA CCC AAT GGC ACC AAC CCC AGT GTC TTC TCC TTC CTC        1680
Leu Tyr Arg Lys Pro Asn Gly Thr Asn Pro Ser Val Phe Ser Phe Leu
545                 550                 555                 560

AAC CCC CTG TCC CCA GAC ATC TGG ATG TAC GTG CTA CTC GCC TAC CTG        1728
Asn Pro Leu Ser Pro Asp Ile Trp Met Tyr Val Leu Leu Ala Tyr Leu
                565                 570                 575

GGT GTC AGC TGT GTC CTC TTC GTC ATT GCC AGA TTC AGC CCT TAT GAA        1776
Gly Val Ser Cys Val Leu Phe Val Ile Ala Arg Phe Ser Pro Tyr Glu
        580                 585                 590

TGG TAT GAT GCC CAC CCC TGC AAC CCC GGC TCT GAG GTG GTG GAG AAT        1824
Trp Tyr Asp Ala His Pro Cys Asn Pro Gly Ser Glu Val Val Glu Asn
        595                 600                 605

AAC TTC ACG CTG CTC AAC AGC TTC TGG TTT GGA ATG GGC TCC CTG ATG        1872
Asn Phe Thr Leu Leu Asn Ser Phe Trp Phe Gly Met Gly Ser Leu Met
        610                 615                 620

CAA CAA GGA TCT GAA CTG ATG CCC AAA GCT CTG TCT ACC CGC ATC ATT        1920
Gln Gln Gly Ser Glu Leu Met Pro Lys Ala Leu Ser Thr Arg Ile Ile
625                 630                 635                 640

GGC GGC ATC TGG TGG TTC TTC ACC CTT ATT ATC ATC TCC TCC TAC ACG        1968
Gly Gly Ile Trp Trp Phe Phe Thr Leu Ile Ile Ile Ser Ser Tyr Thr
                645                 650                 655

GCC AAC CTG GCT GCC TTC CTG ACC GTG GAG CGC ATG GAG TCA CCC ATC        2016
Ala Asn Leu Ala Ala Phe Leu Thr Val Glu Arg Met Glu Ser Pro Ile
                660                 665                 670

GAC TCT GCC GAT GAC CTG GCC AAG CAG ACC AAA ATA GAG TAC GGT GCT        2064
Asp Ser Ala Asp Asp Leu Ala Lys Gln Thr Lys Ile Glu Tyr Gly Ala
        675                 680                 685

GTC AAG GAT GGG GCC ACC ATG ACC TTC TTC AAG AAA TCC AAG ATC TCC        2112
Val Lys Asp Gly Ala Thr Met Thr Phe Phe Lys Lys Ser Lys Ile Ser
        690                 695                 700

ACC TTT GAG AAG ATG TGG GCC TTC ATG AGC AGC AAG CCC TCG GCT CTG        2160
Thr Phe Glu Lys Met Trp Ala Phe Met Ser Ser Lys Pro Ser Ala Leu
705                 710                 715                 720

GTG AAG AAC AAT GAG GAG GGC ATC CAG CGG ACA CTC ACA GCT GAC TAC        2208
Val Lys Asn Asn Glu Glu Gly Ile Gln Arg Thr Leu Thr Ala Asp Tyr
                725                 730                 735

GCT CTG CTC ATG GAG TCC ACG ACC ATA GAG TAC ATC ACA CAA AGG AAC        2256
Ala Leu Leu Met Glu Ser Thr Thr Ile Glu Tyr Ile Thr Gln Arg Asn
        740                 745                 750

TGC AAT CTC ACC CAG ATC GGC GGC CTC ATC GAT TCC AAG GGC TAC GGC        2304
Cys Asn Leu Thr Gln Ile Gly Gly Leu Ile Asp Ser Lys Gly Tyr Gly
        755                 760                 765

ATC GGC ACG CCC ATG GGC TCC CCC TAC AGG GAC AAA ATC ACC ATC GCC        2352
Ile Gly Thr Pro Met Gly Ser Pro Tyr Arg Asp Lys Ile Thr Ile Ala
        770                 775                 780

ATT CTG CAG CTG CAG GAG GAG GAC AAG CTG CAC ATC ATG AAG GAG AAG        2400
Ile Leu Gln Leu Gln Glu Glu Asp Lys Leu His Ile Met Lys Glu Lys
785                 790                 795                 800

TGG TGG CGA GGC AGC GGG TGC CCC GAG GAG GAG AAC AAG GAG GCC AGC        2448
Trp Trp Arg Gly Ser Gly Cys Pro Glu Glu Glu Asn Lys Glu Ala Ser
                805                 810                 815

GCA CTG GGC ATC CAG AAG ATT GGC GGC ATC TTC ATC GTC CTG GCT GCC        2496
Ala Leu Gly Ile Gln Lys Ile Gly Gly Ile Phe Ile Val Leu Ala Ala
        820                 825                 830
```

```
GGC TTA GTC CTG TCC GTG TTG GTG GCA GTG GGC GAG TTT ATA TAC AAA      2544
Gly Leu Val Leu Ser Val Leu Val Ala Val Gly Glu Phe Ile Tyr Lys
        835                 840                 845

CTC CGC AAG ACA GCG GAA CGG GAG CAG CGC TCT TTC TGC AGC ACA GTG      2592
Leu Arg Lys Thr Ala Glu Arg Glu Gln Arg Ser Phe Cys Ser Thr Val
850                 855                 860

GCC GAC GAG ATC CGC TTC TCC CTC ACC TGC CAG CGG CGT CTC AAG CAC      2640
Ala Asp Glu Ile Arg Phe Ser Leu Thr Cys Gln Arg Arg Leu Lys His
865                 870                 875                 880

AAG CCA CAG CCT CCT ATG ATG GTC AAG ACA GAT GCG GTT ATC AAC ATG      2688
Lys Pro Gln Pro Pro Met Met Val Lys Thr Asp Ala Val Ile Asn Met
                885                 890                 895

CAC ACC TTT AAT GAC CGA AGG CTT CCA GGC AAG GAC AGC ATG AGC TGC      2736
His Thr Phe Asn Asp Arg Arg Leu Pro Gly Lys Asp Ser Met Ser Cys
            900                 905                 910

AGC ACC TCG CTA GCC CCT GTC TTC CCT TAGACTTGGG TCCAGCGGGG ACTTCAG    2790
Ser Thr Ser Leu Ala Pro Val Phe Pro
        915                 920

GCCCGGTCCA CGCAGAGGAA GGCAAAGGAG ACCCGAAAGG ACATCCTCAT CTCATGCTGG    2850

CCTTGGGGAT GGAGCTGCTG CCCGCATCCG GCTGTGAACC ATCAGCTCTT ACCTACCGGG    2910

GAAACCCATG GGCCCTCAGC AGCTGCTTGG GCTTCATCTC CTCTTGTCTT TTTTGTGGCT    2970

TTCTGAAGCT GTGAAGGCCA GCGGAAGCAC ACGCCTCTCA GGCTGCACTC ACCGACCATC    3030

TCCATAGCCA GCTACTTCGG CCAGGGCTCT GCAGAGGCCT CGGAACACCA GAGATAGCTC    3090

TTACACCTCC CTCCCTCCCC TCAAGTCCAG GCCTTCTAGC ACGCACCCAT GAGAGCAGAG    3150

ACTCCAGCTC AGAACGCCTT GAGGGTGTTC TGAGGAGGCC ACCAGTGGGA GCCCCAAGGC    3210

AGCCATCCAT ACCTGGACAG AAGCAAAGCT TCAGCCCTTA AGGGCTATTC ACCTGGGTCT    3270

GCCCTCCCCA ACGTGGCTTC GCCCTCGTGC CGAATTCGAT ATCAAGCTTA TCGATACCGT    3330

CGACCTCGAG GGGG                                                     3344

(2) INFORMATION FOR SEQ ID NO:14:

(i) SEQUENCE CHARACTERISTICS:
        (A) LENGTH: 921 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Gly Ala Val Ala Gly Ser Leu Gly Arg Leu Arg Ser Leu Val Trp Glu
 1               5                  10                  15

Tyr Trp Ala Gly Phe Leu Val Cys Ala Phe Trp Ile Pro Asp Ser Arg
            20                  25                  30

Gly Met Pro His Val Ile Arg Ile Gly Gly Ile Phe Glu Tyr Ala Asp
        35                  40                  45

Gly Pro Asn Ala Gln Val Met Asn Ala Glu Glu His Ala Phe Arg Phe
    50                  55                  60

Ser Ala Asn Ile Ile Asn Arg Asn Arg Thr Leu Leu Pro Asn Thr Thr
65                  70                  75                  80

Leu Thr Tyr Asp Ile Gln Arg Ile His Phe His Asp Ser Phe Glu Ala
                85                  90                  95

Thr Lys Lys Ala Cys Asp Gln Leu Ala Leu Gly Val Val Ala Ile Phe
            100                 105                 110

Gly Pro Ser Gln Gly Ser Cys Ile Asn Ala Val Gln Ser Ile Cys Asn
```

-continued

```
            115                 120                 125
Ala Leu Glu Val Pro His Ile Gln Leu Arg Trp Lys His His Pro Leu
130                 135                 140
Asp Asn Lys Asp Thr Phe Tyr Val Asn Leu Tyr Pro Asp Tyr Ala Ser
145                 150                 155                 160
Leu Ser His Ala Ile Leu Asp Leu Val Gln Ser Leu Lys Trp Arg Ser
                165                 170                 175
Ala Thr Val Val Tyr Asp Asp Ser Thr Gly Leu Ile Arg Leu Gln Glu
            180                 185                 190
Leu Ile Met Ala Pro Ser Arg Tyr Asn Ile Arg Leu Lys Ile Arg Gln
        195                 200                 205
Leu Pro Ile Asp Ser Asp Ser Arg Pro Leu Leu Lys Glu Met Lys
210                 215                 220
Arg Gly Arg Glu Phe Arg Ile Ile Phe Asp Cys Ser His Thr Met Ala
225                 230                 235                 240
Ala Gln Ile Leu Lys Gln Ala Met Ala Met Gly Met Met Thr Glu Tyr
                245                 250                 255
Tyr His Phe Ile Phe Thr Thr Leu Asp Leu Tyr Ala Leu Asp Leu Glu
            260                 265                 270
Pro Tyr Arg Tyr Ser Gly Val Asn Leu Thr Gly Phe Arg Ile Leu Asn
        275                 280                 285
Val Asp Asn Pro His Val Ser Ala Ile Val Glu Lys Trp Ser Met Glu
290                 295                 300
Arg Leu Gln Ala Ala Pro Arg Ala Glu Ser Gly Leu Leu Asp Gly Val
305                 310                 315                 320
Met Met Thr Asp Ala Ala Leu Leu Tyr Asp Ala Val His Ile Val Ser
                325                 330                 335
Val Cys Tyr Gln Arg Ala Pro Gln Met Thr Val Asn Ser Leu Gln Cys
            340                 345                 350
His Arg His Lys Ala Trp Arg Phe Gly Gly Arg Phe Met Asn Phe Ile
        355                 360                 365
Lys Glu Ala Gln Trp Glu Gly Leu Thr Gly Arg Ile Val Phe Asn Lys
370                 375                 380
Thr Ser Gly Leu Arg Thr Asp Phe Asp Leu Asp Ile Ile Ser Leu Lys
385                 390                 395                 400
Glu Asp Gly Leu Glu Lys Val Gly Val Trp Ser Pro Ala Asp Gly Leu
                405                 410                 415
Asn Ile Thr Glu Val Ala Lys Gly Arg Gly Pro Asn Val Thr Asp Ser
            420                 425                 430
Leu Thr Asn Arg Ser Leu Ile Val Thr Thr Leu Leu Glu Glu Pro Phe
        435                 440                 445
Val Met Phe Arg Lys Ser Asp Arg Thr Leu Tyr Gly Asn Asp Arg Phe
450                 455                 460
Glu Gly Tyr Cys Ile Asp Leu Leu Lys Glu Leu Ala His Ile Leu Gly
465                 470                 475                 480
Phe Ser Tyr Glu Ile Arg Leu Val Glu Asp Gly Lys Tyr Gly Ala Gln
                485                 490                 495
Asp Asp Lys Gly Gln Trp Asn Gly Met Val Lys Glu Leu Ile Asp His
            500                 505                 510
Lys Ala Asp Leu Ala Val Ala Pro Leu Thr Ile Thr His Val Arg Glu
        515                 520                 525
Lys Ala Ile Asp Phe Ser Lys Pro Phe Met Thr Leu Gly Val Ser Ile
530                 535                 540
```

```
Leu Tyr Arg Lys Pro Asn Gly Thr Asn Pro Ser Val Phe Ser Phe Leu
545                 550                 555                 560

Asn Pro Leu Ser Pro Asp Ile Trp Met Tyr Val Leu Leu Ala Tyr Leu
                565                 570                 575

Gly Val Ser Cys Val Leu Phe Val Ile Ala Arg Phe Ser Pro Tyr Glu
                580                 585                 590

Trp Tyr Asp Ala His Pro Cys Asn Pro Gly Ser Glu Val Val Glu Asn
            595                 600                 605

Asn Phe Thr Leu Leu Asn Ser Phe Trp Phe Gly Met Gly Ser Leu Met
        610                 615                 620

Gln Gln Gly Ser Glu Leu Met Pro Lys Ala Leu Ser Thr Arg Ile Ile
625                 630                 635                 640

Gly Gly Ile Trp Trp Phe Phe Thr Leu Ile Ile Ile Ser Ser Tyr Thr
                645                 650                 655

Ala Asn Leu Ala Ala Phe Leu Thr Val Glu Arg Met Glu Ser Pro Ile
                660                 665                 670

Asp Ser Ala Asp Asp Leu Ala Lys Gln Thr Lys Ile Glu Tyr Gly Ala
            675                 680                 685

Val Lys Asp Gly Ala Thr Met Thr Phe Phe Lys Lys Ser Lys Ile Ser
        690                 695                 700

Thr Phe Glu Lys Met Trp Ala Phe Met Ser Ser Lys Pro Ser Ala Leu
705                 710                 715                 720

Val Lys Asn Asn Glu Glu Gly Ile Gln Arg Thr Leu Thr Ala Asp Tyr
                725                 730                 735

Ala Leu Leu Met Glu Ser Thr Thr Ile Glu Tyr Ile Thr Gln Arg Asn
                740                 745                 750

Cys Asn Leu Thr Gln Ile Gly Gly Leu Ile Asp Ser Lys Gly Tyr Gly
            755                 760                 765

Ile Gly Thr Pro Met Gly Ser Pro Tyr Arg Asp Lys Ile Thr Ile Ala
        770                 775                 780

Ile Leu Gln Leu Gln Glu Glu Asp Lys Leu His Ile Met Lys Glu Lys
785                 790                 795                 800

Trp Trp Arg Gly Ser Gly Cys Pro Glu Glu Glu Asn Lys Glu Ala Ser
                805                 810                 815

Ala Leu Gly Ile Gln Lys Ile Gly Gly Ile Phe Ile Val Leu Ala Ala
            820                 825                 830

Gly Leu Val Leu Ser Val Leu Val Ala Val Gly Glu Phe Ile Tyr Lys
        835                 840                 845

Leu Arg Lys Thr Ala Glu Arg Glu Gln Arg Ser Phe Cys Ser Thr Val
850                 855                 860

Ala Asp Glu Ile Arg Phe Ser Leu Thr Cys Gln Arg Arg Leu Lys His
865                 870                 875                 880

Lys Pro Gln Pro Pro Met Met Val Lys Thr Asp Ala Val Ile Asn Met
                885                 890                 895

His Thr Phe Asn Asp Arg Arg Leu Pro Gly Lys Asp Ser Met Ser Cys
            900                 905                 910

Ser Thr Ser Leu Ala Pro Val Phe Pro
        915                 920
```

GLUTAMATE RECEPTOR COMPOSITIONS AND METHOD

PRIOR APPLICATIONS

This application is a divisional application of U.S. Ser. No. 08/013,767, filed Feb. 4, 1993, now abandoned which is a divisional of U.S. Ser. No. 07/718,575, filed Jun. 21, 1991, now U.S. Pat. No. 5,202,257, which is a continuation of PCT Application No. US90/06153, filed Oct. 25, 1990, which is a continuation-in-part application of U.S. Ser. No. 07/428,116, filed October 27, 1989, now abandoned.

ACKNOWLEDGEMENT

This invention was made with Government support under Grant Numbers NS 11549 and NS 28709.01, awarded by the National Institutes of Health. The Government has certain rights in this invention.

FIELD OF THE INVENTION

The present invention relates to a family of novel DNA sequences and receptor proteins encoded thereby that comprise the glutamate neurotransmitter system. The invention also relates to methods for making such glutamate receptors and for using the receptor proteins in assays designed to identify and characterize compounds which affect the function of such receptor s, e.g., glutamate agonists and antagonists.

BACKGROUND OF THE INVENTION

The amino acid L-glutamate is a major excitatory neurotransmitter in the mammalian central nervous system. Anatomical, biochemical and electrophysiological analyses suggest that glutamatergic systems are involved in a broad array of neuronal processes, including fast excitatory synaptic transmission, regulation of neurotransmitter releases, long-term potentiation, learning and memory, developmental synaptic plasticity, hypoxic-ischemic damage and neuronal cell death, epileptiform seizures, as well as the pathogenesis of several neurodegenerative disorders. See generally, Monaghan et al., Ann. Rev. Pharmacol. Toxicol. 29:365–402 (1980). This extensive repertoire of functions, especially those related to learning, neurotoxicity and neuropathology, has stimulated recent attempts to describe and define the mechanisms through which glutamate exerts its effects.

Currently, glutamate receptor classification schemes are based on pharmacological criteria which serve to define five receptor subtypes or classes: those activated by N-methyl-D-aspartic acid (NMDA), kainic acid (KA), α-amino-3-hydroxy-5-methyl-isoxazole-4-propionic acid (AMPA, formally called the quisqualic acid or QUIS receptor), 2-amino-4-phosphonobutyric acid (AP4 or APB), and 1-amino-cyclopentyl-1,3-dicarboxylic acid (ACPD). The effects of glutamate are mediated primarily through interactions with cation-selective, ionotropic receptors [Foster and Fagg, Brain Res. 7:103–164 (1984); Strange, Biochem. J. 249:309–318 (1988)]. An exception is the ACPD receptor subtype which has the properties of a metabotropic receptor. This class of glutamate receptors alters synaptic physiology via GTP-binding proteins and the second messengers diacylglycerol and inositol 1,4,5-triphosphate [Gundersen et al., Proc. R. Soc. London Ser. 221:127 (1984); Sladeczek et al., Nature 317:717 (1985); Nicoletti et al., J. Neurosci. 6:1905 (1986); Sugiyama et al., Nature 325:531 (1987)].

The electrophysiological and pharmacological properties of the glutamate receptors have been extensively studied and are now well established. See, for example, Foster and Fagg, Brain Res. Rev. 7:103 (1984); Cotman et al., Trends Neurosci. 10:263 (1987); Mayer and Westbrook, Prog. Neurobiol. 28:197 (1987); Watkins and Olvermann, Trends Neurosci. 10:265 (1987); and Blair et al., Science 242:577 (1988). This is in contrast to their biochemical characteristics and structure at the molecular level, which, until the teaching of the present invention, remained largely unknown.

SUMMARY OF THE INVENTION

The present invention discloses a family of novel glutamate receptor proteins and DNA sequences that encode them. The glutamate receptors of the invention have electrophysiological and pharmacological properties characteristic of glutamate receptors of the central and peripheral nervous system. The glutamate receptors of the present invention are exemplified by cation-selective ion channel-type proteins encoded by cDNA clones, GluR1, GluR2, GluR3, GluR4, GluR5, GluR6 and GluR7. In addition to being useful for the production of glutamate receptor proteins, these CDNAS are also useful as probes, thus enabling those skilled in the art, without undue experimentation, to identify and isolate additional proteins in the glutamate receptor family.

The novel functional glutamate receptors of the present invention can be assembled from a plurality of either individual GluR subunit proteins (homomeric) or from combinations of subunit proteins (heteromeric). GluR1, GluR2, GluR3, GluR4, GluR5, GluR6 and GluR7 are examples of presently preferred subunit proteins for forming homomeric receptors, while the combinations of GluR1, GluR2, GluR3, GluR4, GluR5, GluR6 and GluR7 are examples of presently preferred subunit proteins for forming heteromeric receptors.

In addition to disclosing novel glutamate receptor proteins, the present invention also comprises methods for using such receptors to identify and characterize compounds which affect the function of such receptors, e.g., agonists, antagonists, and modulators of glutamate receptor function. The invention also comprises methods for determining whether unknown protein(s) are functional as glutamate receptors.

BRIEF DESCRIPTION OF THE FIGURES

FIG. 1 (a and b) comprises two sequence homology analyses. FIG. 1a compares the extracellular region located between amino acid residues 89 and 106 of GluR1 with the "Cys-Cys-loop" region found in all other ligand-gated ion channels, showing sequence homology. FIG. 1b compares the putative TMD II region of GluR1 with hypothetical TMD II regions of other ligand-gated ion channels, suggesting protein sequence conservation.

FIG. 2A is a drawing which shows the alignment of deduced amino acid sequences for the GluR1, GluR2, GluR3, GluR4 and GluR5 (GluR5-1) subunits of the glutamate receptor gene family.

FIG. 2B is a drawing which shows the alignment of deduced amino acid signal sequences for the GluR1, GluR2, GluR3, GluR4, GluR5 (GluR5-1), GluR6 and GluR7 subunits of the glutamate receptor gene family.

Figure 3A:
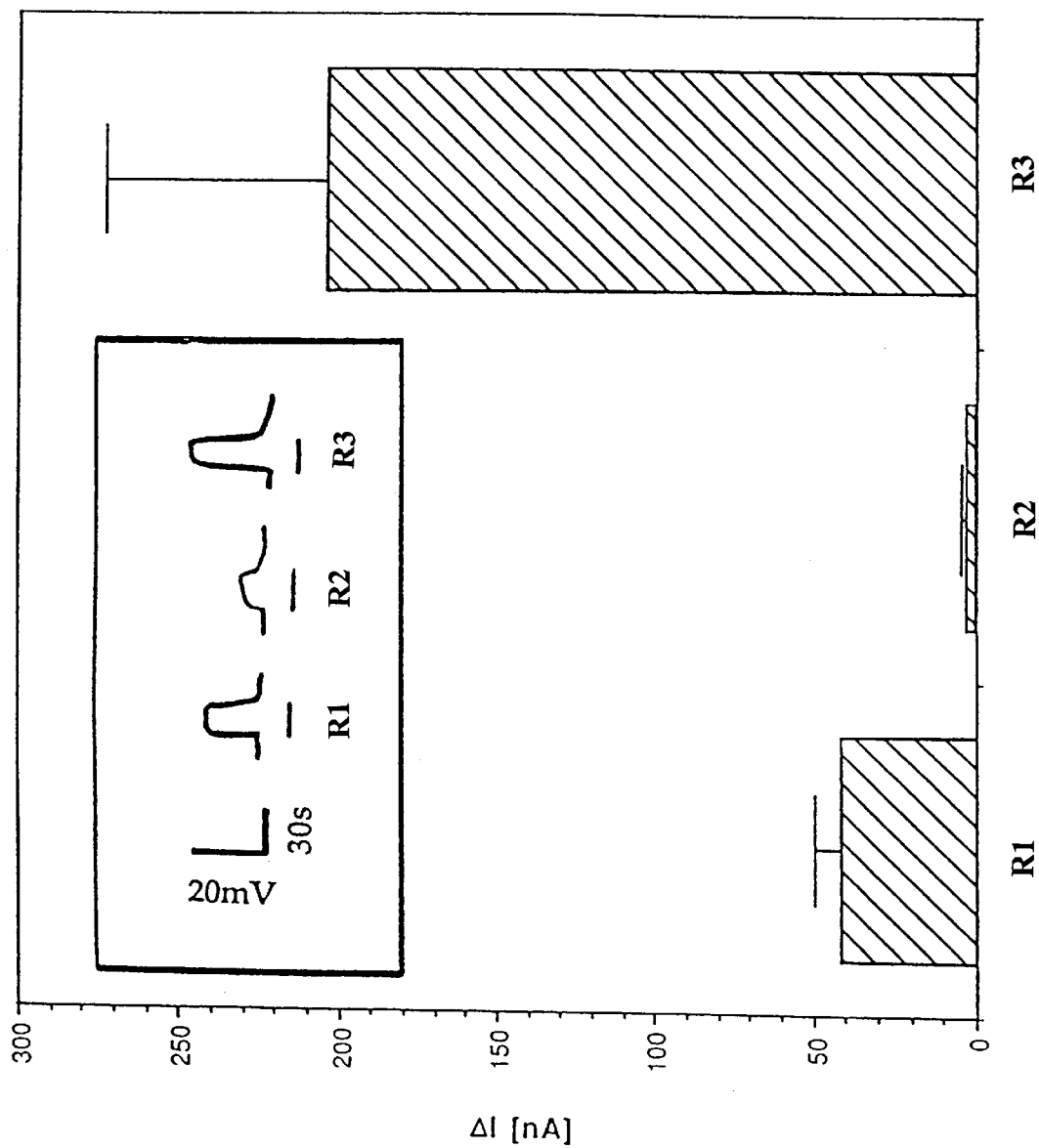
FIG. 3 (A and B) is comprised of two graphs which compare current responses measured in Xenopus) oocytes injected with individual GluR1, GluR2 and GluR3 subunit RNAs (FIG. 3A) or rat brain hippocampus poly(A)$^+$RNA (FIG. 3B).

The amino acids appearing herein may be identified according to the following three-letter or one-letter abbreviations:

| Amino Acid | 3 Letter Abbreviation | 1 Letter Abbreviation |
| --- | --- | --- |
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

The nucleotides appearing herein have the usual single-letter designations (A, G, T, C or U) routinely used in the art.

DETAILED DESCRIPTION OF THE INVENTION

The present invention discloses a family of glutamate receptors, novel DNA sequences that encode these receptors, and various applications thereof.

As used herein, glutamate receptors refer to neurotransmitter receptor proteins that are activated by L-glutamate and related compounds. These receptor proteins are classified on the basis of their "pharmacology". Currently there are five classes of receptors, i.e., receptors activated by (1) N-methyl-D-aspartate (NMDA), which is a ligand (agonist) for the NMDA glutamate receptor subtype; (2) kainic acid (KA), which is a ligand (agonist) for the kainate glutamate receptor subtype; (3) a-amino-3-hydroxy-5-methyl-isoxazole-4-propionic acid (AMPA), which is a ligand (agonist) for the AMPA glutamate receptor subtype, formerly called the quisqualic acid or QUIS receptor, wherein QUIS means quisqualic acid or quisqualate, which is a ligand (agonist) for the pharmacologically defined receptor subtype previously referred to as the QUIS (quisqualate) receptor; (4) 2-amino-4-phosphonobutyric acid (AP4 or APB), which is a ligand (agonist) for the APB glutamate receptor subtype; the acronym AP4 is also used to refer to this receptor subtype; and (5) 1-aminocyclopentyl-1,3-dicarboxylic acid (ACPD), which is a ligand (agonist) for the ACPD glutamate receptor subtype.

The effects of glutamate on the first four subtypes described above are mediated primarily through interactions with cation-selective, ionotropic receptors. The ACPD receptor subtype, however, is an exception in that it has the properties of a metabotropic receptor. Metabotropic receptors alter synaptic physiology via GTP-binding proteins and second messengers (i.e., diacylglycerol and inositol 1,4,5-triphosphate).

In one aspect, the present invention comprises substantially pure proteins, or functional fragments thereof, having electrophysiological and pharmacological properties characteristic of at least one ionotropic glutamate receptor subtype selected from the N-methyl-D-aspartate (NMDA) subtype, the α-amino-3-hydroxy-5-methylisoxazole-4-propionic acid (AMPA) subtype, kainate (KA) subtype or the 2-amino-4-phosphonobutyrate (APB) subtype.

When used herein as a modifier of glutamate receptor protein(s) of the present invention, the phrase "having electrophysiological and pharmacological properties characteristic of a glutamate receptor" means that the neuronal signal(s) generated by receptor protein in response to glutamate or glutamate-like ligands will be comparable to those of known glutamate receptors.

The term "functional", when used herein as a modifier of glutamate receptor protein(s) of the present invention (or fragments thereof), means that binding of glutamate (or glutamate-like) ligand to receptor protein(s) causes membrane "ion channels" to open. This allows ions to move across the membrane, which in turn depolarizes the cell and generates a neuronal signal. Stated another way, "functional" means that a neuronal signal is generated as a consequence of ligand binding to receptor protein(s).

As used herein, the words "protein", "peptide" and "polypeptide" are considered to be equivalent terms and are used interchangeably.

Also contemplated by the present invention are homomeric and heteromeric (or multimeric) combinations of the above-described receptor subtypes.

As used herein, homomeric means receptors comprised of a plurality of only one type of subunit protein, e.g., homodimers, homotrimers, etc.

As used herein, heteromeric or multimeric means receptors comprised of more than one type of subunit protein.

In another aspect, the invention comprises antibodies generated against the above-described receptor proteins. Such antibodies can be used to modulate the ion channel activity of glutamate receptors, by contacting such receptors with an effective amount of such antibody.

In yet another aspect, the invention comprises substantially pure DNA encoding proteins or functional fragments thereof, as described hereinabove.

Use of the phrase "substantially pure" in the present specification and claims as a modifier of DNA, RNA, polypeptides or proteins means that the DNA, RNA, polypeptides or proteins so designated have been separated from their in vivo cellular environment. As a result of this separation and purification, the substantially pure DNAs, RNAs, polypeptides and proteins are useful in ways that the non-separated, impure DNAs, RNAs, polypeptides or proteins are not.

In still another aspect, the invention comprises cells transformed with DNAs of the invention.

In another aspect, the invention comprises substantially pure sense or antisense mRNA transcribed from the above-described DNAs, wherein the DNAs encode substantially pure functional proteins that have electrophysiological and pharmacological properties characteristic of a glutamate receptor.

In still another aspect, the invention comprises Xenopus oocytes to which mRNA of the invention has been introduced, e.g., by injection.

Still further, the invention comprises novel glutamate receptors made by expression of DNA sequences of the invention, or translation of the corresponding mRNAs. Such novel receptors include the individual GluR1, GluR2, GluR3, GluR4, GluR5, GluR6 and GluR7 receptors, fragments thereof, plus functional combinations of the receptors or fragments.

Still further, the invention comprises DNA, RNA and proteins that are functionally equivalent to the DNAs, RNAs and proteins of the present invention. Such functionally equivalent DNAs, RNAs and proteins will function in substantially the same manner as the DNAs, RNAs and proteins of the invention.

Presently preferred proteins of the invention, or functional fragments thereof, or functional combinations of these proteins and/or fragments, are proteins or functional fragments or functional combinations thereof which have electrophysiological and pharmacological properties characteristic of KA and/or AMPA glutamate receptor subtypes.

The invention proteins, or functional fragments thereof, or functional combinations of the proteins and/or the fragments, can be characterized as being encoded by DNA having at least about 40% nucleic acid homology with at least one member of the group consisting of GluR1 DNA (see, for example, Sequence ID No. 1), GluR2 DNA (see, for example, Sequence ID No. 3), GluR3 DNA (see, for example, Sequence ID No. 5), GluR4 DNA (see, for example, Sequence ID No. 7), GluR5 DNA (see, for example, Sequence ID No. 9), GluR6 DNA (see, for example Sequence ID No. 11) and GluR7 DNA (see, for example, Sequence ID No. 13), as well as substantially pure functional proteins having substantial sequence homology with the substantially pure functional proteins of the invention.

The phrase "substantial sequence homology", as used in the present specification and claims, means that the DNA, RNA or amino acid sequences which have slight and non-consequential sequence variations from the actual sequences disclosed and claimed herein are considered to be equivalent to the sequences of the present invention, and as such are within the scope of the appended claims. In this regard, "slight and non-consequential sequence variations" mean that "homologous" sequences (i.e., the sequences that have substantial sequence homology with the DNA, RNA, or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

Alternatively, the invention proteins, or functional fragments thereof, or functional combinations of the proteins and/or the fragments can be characterized as receptors which have at least about 40% overall amino acid homology with at least one member of the group consisting of GluR1 (see, for example, Sequence ID No. 2), GluR2 (see, for example, Sequence ID No. 4), GluR3 (see, for example, Sequence ID No. 6), GluR4 (see, for example, Sequence ID No. 8), GluR5 (see, for example, Sequence ID No. 10), GluR6 (see, for example, Sequence ID No. 12) and GluR7 (see, for example, Sequence ID No. 14), as well as substantially pure functional proteins having substantial sequence homology with the substantially pure functional proteins of the invention.

Presently preferred receptor proteins of the invention, or functional fragments thereof, or functional combinations of such proteins and/or fragments are characterized as receptors having at least about 50% amino acid homology in the C-terminal domain thereof with the C-terminal domain of at least one member of the group consisting of GluR1 (see, for example, Sequence ID No. 2), GluR2 (see, for example, Sequence ID No. 4), GluR3 (see, for example, Sequence ID No. 6), GluR4 (see, for example, Sequence ID No. 8), GluR5 (see, for example, Sequence ID No. 10), GluR6 (see, for example, Sequence ID No. 12) and GluR7 (see, for example, Sequence ID No. 14), as well as substantially pure functional proteins having substantial sequence homology with the substantially pure functional proteins of the invention.

Exemplary receptors of the invention comprise substantially pure proteins selected from GluR1, GluR2, GluR3, GluR4, GluR5, GluR6 and GluR7, and combinations thereof wherein said combinations are functional as glutamate receptor(s).

As used herein, GluR1 refers to a cDNA clone which encodes a single glutamate receptor subunit protein of the same name having a $M_r$ (of the non-glycosylated receptor) of approximately 99.8 kilodaltons (kD). GluR1 was the first glutamate receptor subunit encoding cDNA to be isolated; it was previously referred to as GluR-K1. GluR-K1 has been renamed glutamate receptor subunit gene 1 or, more simply, GluR1. Additional glutamate receptor subunits or subunit related genes are called GluR2, GluR3, GluR4, GluR5, GluR6, GluR7 and so forth. GluR1 cDNA was deposited with the American Type Culture Collection on Oct. 19, 1989; and has been accorded ATCC Accession No. 68134.

As used herein GluR2 refers to a cDNA clone which encodes a single glutamate receptor subunit protein of the same name having a $M_r$ (of the non-glycosylated receptor) of approximately 96.4 kD. GluR2 cDNA was deposited with the American Type Culture Collection on Oct. 19, 1989; and has been accorded ATCC Accession No. 68132.

As used herein, GluR3 refers to a cDNA clone which encodes a single glutamate receptor subunit protein of the same name having a $M_r$ (of the non-glycosylated receptor) of approximately 98.0 kD. GluR3 cDNA was deposited with the American Type Culture Collection on Oct. 19, 1989; and has been accorded ATCC Accession No. 68133.

As used herein, GluR4 refers to a cDNA clone which encodes a single protein of the same name having a $M_r$ (of the non-glycosylated receptor) of approximately 98.5 kD. GluR4 cDNA was deposited with the American Type Culture Collection on Aug. 2, 1990; and has been accorded ATCC Accession No. 68375.

As used herein, GluR5 refers to a GluR5 cDNA clone which encodes a single protein of the same name having a $M_r$ (of the non-glycosylated receptor) of approximately 100 kD. GluR5 cDNA (as GluR5-1) was deposited with the American Type Culture Collection on Aug. 2, 1990; and has been accorded ATCC Accession No. 68374. There are two length variants of GluR5 cDNA, referred to herein as GluR5-1 and GluR5-2. Translation of the GluR5 cDNAs predicts a single long open reading frame of 920 amino acids. The difference between GluR5-1 and GluR5-2 DNA derives from an insertion of 45 nucleotides (15 amino acids) in the GluR5-1 DNA which does not interrupt this reading frame. The 15 amino acid insertion in the GluR5-1 receptor protein is unique among the receptor proteins disclosed herein; thus the shorter GluR5-2 variant is the counterpart of the GluR1, GluR2, GluR3, GluR4, GluR6 and GluR7 subunits.

As used herein, GluR6 refers to a cDNA clone which encodes a single protein of the same name having a $M_r$ (of the non-glycosylated receptor) of approximately 100 kD.

As used herein, GluR7 refers to a cDNA clone which encodes a single protein of the same name having a $M_r$ (of the non-glycosylated receptor) of approximately 100 kD.

As used herein, GluR1, GluR2, GluR3, GluR4, GluR5, GluR6 and GluR7 are each used interchangeably to refer to genes, cDNA clones and the glutamate receptor proteins they encode.

Presently preferred receptors of the invention comprise substantially pure proteins having $M_r$s (of the non-glycosylated receptor) of about 99.8 kD (GluR1), 96.4 kD (GluR2), 98.0 kD (GluR3), 98.5 kD (GluR4), 100 kD (GluR5), 100 kD (GluR6), and 100 kD (GluR7), as well as channels which possess the electrophysiological and pharmacological properties characteristic of glutamate receptors of the KA and/or AMPA subtypes.

In accordance with yet another embodiment of the present invention, there are provided antibodies generated against the above-described receptor proteins. Such antibodies can be employed for diagnostic applications, therapeutic applications, and the like. Preferably, for therapeutic applications, the antibodies employed will be monoclonal antibodies.

The above-described antibodies can be prepared employing standard techniques, as are well known to those of skill in the art, using the invention receptor proteins as antigens for antibody production.

In accordance with still another embodiment of the present invention, there are provided methods for modulating the ion channel activity of receptor(s) of the invention by contacting said receptor(s) with an effective amount of the above-described antibodies.

The antibodies of the invention can be administered to a subject employing standard methods, such as, for example, by intraperitoneal, intramuscular, intravenous, or subcutaneous injection, implant or transdermal modes of administration, and the like. One of skill in the art can readily determine dose forms, treatment regiments, etc, depending on the mode of administration employed.

The invention DNA can be characterized as comprising substantially pure DNA having at least about 50% overall nucleic acid homology with at least one member of the group consisting of GluR1 DNA, GluR2 DNA, GluR3 DNA, GluR4 DNA, GluR5 DNA, GluR6 DNA and GluR7 DNA.

Alternatively, the invention DNA comprises substantially pure DNA encoding proteins having at least about 40% overall amino acid homology with at least one member of the group consisting of GluR1 (see, for example, Sequence ID No. 2), GluR2 (See, for example, Sequence ID No. 4), GluR3 (see, for example, Sequence ID No. 6) GluR4 (see, for example, Sequence ID No. 8), GluR5 (see, for example, Sequence ID No. 10), GluR6 (see, for example, Sequence ID No. 12), and GluR7 (see, for example, Sequence ID No. 14).

Presently preferred DNA are substantially pure DNA encoding substantially pure proteins having $M_r$s (of the non-glycosylated receptor) of about 99.8 kD (GluR1), 96.4 kD (GluR2), 98.0 kD (GluR3), 98.5 kD (GluR4), 100 kD (GluR5), 100 kD (GluR6), and 100 kD (GluR7), as well as combinations thereof that form ion channels which possess the electrophysiological and pharmacological properties characteristic of a glutamate receptor of the KA and/or AMPA subtypes.

Especially preferred DNA sequences of the invention comprise substantially pure DNA selected from GluR1 DNA (see, for example, Sequence ID No. 1), GluR2 DNA (see, for example, Sequence ID No. 3), GluR3 DNA (see, for example, Sequence ID No. 5), GluR4 DNA (see, for example, Sequence ID No. 7), GluR5 DNA (see, for example, Sequence ID No. 9), GluR6 DNA (see, for example, Sequence ID No. 11) and GluR7 DNA (see, for example, Sequence ID No. 13).

Also contemplated by the present invention are substantially pure DNA that are functionally equivalent to any of the substantially pure DNAs of the invention, wherein functionally equivalent means that the substantially pure DNA will encode proteins, or functional fragments thereof, which will form ion channel(s) in response to ligands for glutamate receptors.

Representative clones of the above-described DNA sequences have been deposited with the American Type Culture Collection. The representative cDNA clones include: GluR1 (ATCC No. 68134), GluR2 (ATCC No. 68132), GluR3 (ATCC No. 68133), GluR4 (ATCC No. 68375), and GluR5 (ATCC No. 65374).

Either the full length cDNA clones or fragments thereof can be used as probes, preferably labeled with suitable label means for ready detection. When fragments are used as probes, preferably the DNA sequences will be from the carboxyl encoding portion of the DNA, and most preferably will include ion channel encoding portions of the DNA sequence. These probes can be used, for example, for the identification and isolation of additional members of the glutamate receptor family.

In another aspect, the invention comprises functional peptide fragments, and functional combinations thereof, encoded by the DNAs of the invention. Such functional peptide fragments can be produced by those skilled in the art, without undue experimentation, by eliminating some or all of the amino acids in the sequence not essential for the peptide to function as a glutamate receptor. A determination of the amino acids that are essential for glutamate receptor function is made, for example, by systematic digestion of the DNAs encoding the peptides and/or by the introduction of deletions into the DNAs. The modified (e.g., deleted or digested) DNAs are expressed, for example, by transcribing the DNA and then introducing the resulting mRNA into Xenopus oocytes, where translation of the mRNAs will occur. Functional analysis of the proteins thus expressed in the oocytes is accomplished by exposing the oocytes to ligands known to bind to and functionally activate glutamate receptors, and then monitoring the oocytes to see if the expressed fragments form ion channel(s). If ion channel(s) are detected, the fragments are functional as glutamate receptors.

In addition to DNA, RNA and protein compositions of matter, several novel methods are contemplated by the present invention. The first is a method for identifying DNA that is homologous to DNA known to encode glutamate receptor protein(s). This method comprises contacting an "unknown" or test sample of DNA with a glutamate receptor DNA probe (e.g., GluR1, GluR2, GluR3, GluR4, GluR5, GluR6, GluR7, etc.) under suitable hybridization conditions, and then identifying "unknown" or test DNA which hybridizes with the glutamate probe DNA as glutamate receptor homologous DNA.

Such screening is initially carried out under low-stringency conditions, which comprise a temperature of about 37° C. or less, a formamide concentration of less than about 50%, and a moderate to low salt (SSC) concentration; or, alternatively, a temperature of about 50° C. or less, and a moderate to high salt (SSPE) concentration. Presently preferred conditions for such screening comprise a temperature of about 37° C., a formamide concentration of about 20%, and a salt concentration of about 5×standard saline citrate (SSC; 20×SSC contains 3M sodium chloride, 0.3M sodium citrate, pH 7.0); or a temperature of about 50° C., and a salt concentration of about 2×SSPE (1×SSPE contains 180 mM NaCl, 9 mM $Na_2HPO_4$, 0.9 mM $NaH_2PO_4$ and 1 mM EDTA, pH 7.4). Such conditions will allow the identification of sequences which have a substantial degree of similarity with the probe sequence, without requiring perfect homology for the identification of a stable hybrid. The phrase "substantial similarity" refers to sequences which share at least 50% overall sequence identity. Preferably, hybridization conditions will be selected which allow the identification of sequences having at least 70% sequence identity with the probe, while discriminating against sequences which have a lower level of sequence identity with respect to the probe.

After low stringency hybridization has been used to identify several clones having a substantial degree of similarity with the probe sequence, this subset of clones is then subjected to high stringency hybridization, so as to identify those clones having particularly high level of homology with respect to the probe sequences. High stringency conditions comprise a temperature of about 42° C. or less, a formamide concentration of less than about 20%, and a low salt (SSC) concentration; or, alternatively, a temperature of about 65° C. or less, and a low salt (SSPE) concentration. Presently preferred conditions for such screening comprise a temperature of about 42° C., a formamide concentration of about 20%, and a salt concentration of about 2×SSC; or a temperature of about 65° C., and a salt concentration of about 0.2×SSPE.

Another method of the invention is directed to identifying functional glutamate receptors (i.e., glutamate receptors that form ion channels). This method comprises contacting glutamate receptor proteins, preferably in an oocyte expression system, with at least one ligand known to activate such receptors, measuring ion channel response to the ligand(s), and identifying as functional glutamate receptor(s) those proteins which exhibit an ion channel response as a consequence of the contact.

In accordance with a further embodiment of the present invention, there is provided a binding assay employing receptors of the invention, whereby a large number of compounds can be rapidly screened to determine which compounds, if any, are capable of binding to glutamate receptors. Subsequently, more detailed assays can be carried out with those compounds found to bind, to further determine whether such compounds act as modulators, agonists or antagonists of invention receptors.

Another application of the binding assay of the invention is the assay of test samples (e.g., biological fluids) for the presence or absence of receptors of the present invention. Thus, for example, serum from a patient displaying symptoms related to glutamate pathway dysfunction can be assayed to determine if the observed symptoms are perhaps caused by over- or under-production of such receptor(s).

The binding assays contemplated by the present invention can be carried out in a variety of ways, as can readily be identified by one of skill in the art. For example, competitive binding assays can be employed, as well as radioimmunoassays, ELISA, ERMA, and the like.

Yet another method of the invention involves determining whether a substance is a functional ligand for glutamate receptor protein (i.e., a modulator, an agonist or an antagonist of glutamate receptor(s)). According to this method, proteins known to function as glutamate receptors are contacted with an "unknown" or test substance (in the further presence of a known glutamate agonist, when antagonist activity is being tested), the ion channel activity of the known glutamate receptor is monitored subsequent to the contact with the "unknown" or test substance, and those substances which increase or decrease the ion channel response of the known glutamate receptor(s) are identified as functional ligands (i.e., modulators, agonists or antagonists) for receptor proteins.

As yet another application of the invention sequences, genetic screening can be carried out using the nucleotide sequences of the invention as probes. Thus, patients having neuropathological conditions suspected of involving alteration/modification of any one or more of the glutamate receptors can be screened with appropriate probes to determine if any abnormalities exist with respect to any of the endogenous glutamate receptors. Similarly, patients having a family history of disease states related to glutamate receptor dysfunction can be screened to determine if they are also predisposed to such disease states.

Turning now to some of the specific DNAs of the invention, cDNA clone GluR1 was isolated from a rat forebrain cDNA library by screening for expression of kainate-gated ion channels in Xenonus oocytes. An insert from clone GluR1 was used as a probe to screen cDNA brain libraries (first under low-stringency hybridization conditions and then under higher stringency conditions) in order to find cDNA clones that encode other members of the glutamate receptor family. Use of the GluR1 probe cDNA led to the identification and isolation of the GluR2 and GluR3 clones. A probe from GluR2 was used to identify and isolate clones GluR4 and GluR5, and GluR5 was used to isolate clones for GluR6 and GluR7.

cDNA clone GluR1 encodes a functional glutamate receptor subunit which consists of a single protein having a $M_r$ (of the non-glycosylated receptor) of about 99.8 kD, before any post-translational modifications. This protein forms an ion channel which possesses the electrophysiological and pharmacological properties of KA and AMPA receptors.

The proteins encoded by the GluR1, GluR2, GluR3, GluR4, GluR5, GluR6 and GluR7 genes exhibit considerable inter-subunit amino acid sequence identity, as summarized in Table 1.

TABLE 1

The Percent Amino Acid Sequence Identity Among Pairwise Combination of Members of the Glutamate Receptor Subunit Gene Family

| | GluR1 | GluR2 | GluR3 | GluR4 | GluR5 | GluR6 | GluR7 |
|---|---|---|---|---|---|---|---|
| A. N-terminal domain | | | | | | | |
| GluR1 | 100 | 58 | 57 | 55 | 34 | 33 | 33 |
| GluR2 | | 100 | 62 | 62 | 33 | 33 | 33 |
| GluR3 | | | 100 | 64 | 34 | 34 | 32 |
| GluR4 | | | | 100 | 32 | 31 | 31 |
| GluR5 | | | | | 100 | 75 | 70 |
| GluR6 | | | | | | 100 | 77 |
| GluR7 | | | | | | | 100 |
| B. C-terminal domain | | | | | | | |
| GluR1 | 100 | 86 | 84 | 84 | 49 | 51 | 48 |
| GluR2 | | 100 | 89 | 88 | 49 | 51 | 50 |
| GluR3 | | | 100 | 87 | 51 | 54 | 50 |
| GluR4 | | | | 100 | 51 | 52 | 48 |
| GluR5 | | | | | 100 | 89 | 79 |
| GluR6 | | | | | | 100 | 87 |
| GluR7 | | | | | | | 100 |
| C. Overall amino acid sequence identity | | | | | | | |
| GluR1 | 100 | 70 | 69 | 68 | 40 | 41 | 39 |
| GluR2 | | 100 | 73 | 72 | 40 | 41 | 40 |
| GluR3 | | | 100 | 73 | 41 | 42 | 40 |
| GluR4 | | | | 100 | 41 | 40 | 39 |
| GluR5 | | | | | 100 | 80 | 78 |
| GluR6 | | | | | | 100 | 79 |
| GluR7 | | | | | | | 100 |

The sequences were compared using sequence analysis software from the University of Wisconsin Genetics Computer Group [Devereux et al., Nucl. Acids Res. 12:387 (1984)]. The percent sequence identity between paired sequences was calculated by dividing the number of aligned positions with identical amino acids by the total number of aligned positions in the shortest of the sequences examined and multiplying the quotient by 100.

These proteins have been found to form distinct homomeric and heteromeric KA/AMPA-sensitive ion channels in Xenopus oocytes. For example, single protein subunits of glutamate receptors, GluR1, GluR2, GluR3, GluR4 and GluR5 are sufficient to form homomeric functional receptor ion-channel complexes activated by KA, AMPA, and QUIS but not by NMDA and APB. While GluR2 subunits can form functional homomeric complexes, this subunit more efficiently assembles receptor-ion channel complexes in heteromeric combination with GluR1 or GluR3 subunits. GluR6 forms homomeric ion channels which are responsive to KA, but not to AMPA.

The GluR5 protein in Xenopus oocytes forms a homomeric ion channel which is weakly responsive to glutamate but not to N-methyl-D-aspartate, kainate, quisqualate and 2-amino-4-phosphonobutyrate. The fact that oocytes expressing GluR5 are responsive to L-glutamate but not to KA, quisqualate or AMPA indicates that this protein can participate in the formation of receptors with a different pharmacological profile than the KA/AMPA subunits.

During embryonic and postnatal development the GluR5 gene is expressed in subsets of neuronal cells in the central nervous system (CNS) and the peripheral nervous system (PNS). The spatial and temporal expression pattern of the GluR5 gene is largely overlapping with the KA/AMPA subunit GluR4. However, in adult brains, the GluR5 gene is expressed in a pattern distinct from those of the KA/AMPA subunit genes, consistent with GluR5 being a subtype of glutamate receptors different from the KA/AMPA receptors.

DEPOSITS cDNA clones encoding representative glutamate receptor protein subunits of the present invention have been deposited with the American Type Culture Collection, Rockville, Md., U.S.A. (ATCC). The deposits have been made under the terms of the Budapest Treaty on the International Recognition of Deposits of Microorganisms for Purposes of Patent Procedure and the Regulations promulgated under this Treaty. Samples of the cloned DNA sequences are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted.

Without further elaboration, one of ordinary skill in the art can, using the preceding description, and the following Examples, utilize the present invention to its fullest extent. The material disclosed in the examples is disclosed for illustrative purposes and therefore should not be construed as being limiting in any way of the appended claims.

EXAMPLES

As used herein, bp means base pairs. Kbp means kilobase pairs, or 1000 base pairs.

As used herein, all temperatures are given in degrees Centigrade unless indicated otherwise.

Example I

Production of Brain cDNA Libraries

Poly(A)$^+$ RNA from various regions of the brain, e.g., mammalian brain, or a suitable cell line, e.g., the NCB-20 cell line, is purified by the guanidine thiocyanate-CsCl method [Chirgwin et al., Biochem 18:5294 (1979)]. The purified RNA is used as a template to prepare double strand cDNA. A poly-dT primer linked to a XhoI restriction site is used as a primer to prime the Moloney reverse transcriptase for the synthesis of the first strand using 5-methyl dCTP instead of CCTP as a precursor. RNaseH and DNA polymerase I are added to complete the second strand. The cDNA is blunt-ended with T4 DNA polymerase which increases the chance of making a full-length cDNA. EcoRI adapters are ligated to the blunt-end and the ends are kinased. The cDNA is then digested with the restriction enzyme, XhoI. This enzyme only cleaves the un-methylated XhoI restriction site attached to the dT-primer at the 3' end of the mRNA. The resulting double stranded cDNA has a XhoI restriction site at the 3' end of the mRNA and an EcoRI site at the 5' end. This cDNA is then placed into an appropriate vector, such as λZAP vector, which is part of the λZAP-cDNA cloning system from Stratagene. When the λZAP vector is used, the cDNA is placed into the vector so that the 5' end of the mRNA is near the lacZ promoter. The λZAP vector has a T3 RNA polymerase promoter at one end of the cDNA insert and a T7 RNA polymerase promoter at the other end which makes it possible to synthesize either sense or antisense RNA for further experiments, including expression in oocytes.

Example II

Low and High Stringency Hybridization cDNA libraries are preferably made with the λZAP-cDNA system described in Example I. A hybridization probe is preferably made from DNA obtained from GluR1, GluR2, GluR3, GluR4, GluR5, GluR6 or GluR7 clones or another suitable clone or source. The DNA is labeled by the random prime method, preferably using the Amersham Multiprime DNA labeling kit (Amersham Corporation, Chicago, Ill.). Preferably, low stringency hybridization conditions are used, at least at first. A suitable hybridization solution is as follows:

1 M NaCl, 50 mM Tris [pH 8.0], 0.5% SDS, 0.1% sodium pyrophosphate, 100 mg/ml denatured herring sperm DNA, 0.1% [w/v] each of Ficoll, polyvinylpyrrolidone and bovine serum albumin.

For low stringency screening, a temperature of 50° C. is preferable, and library filters are washed in 2×SSPE (wherein 1×SSPE is 180 mM NaCl, 9 mM $Na_2HPO_4$, 0.9 mM $NaH_2PO_4$ and 1 mM EDTA, pH 7.4) at room temperature and exposed to Kodak XAR-5 film at −70° C.

Under these low-stringency hybridization conditions, about one in two thousand brain cDNA clones show some hybridization to the probe made from the glutamate receptor cDNA insert.

For high stringency screening, the temperature is adjusted to 65° C. and the filters are washed at this temperature in 0.2×SSPE containing 0.5% sodium dodecyl sulfate. Filters are exposed to Kodak XAR-5 film with Cronex Quanta II/III intensifying screens at −70° C. for 18–48 hours.

Example III

Analysis of Clones Identified by Hybridization

At least two different approaches can be used to analyze clones that are identified by low-stringency hybridization screening. One approach is to pick positive λZAP clones and pool them into mixtures of about 100 clones. mRNA is made in vitro from these pools of λZAP clones and the mRNA is injected into oocytes in order to test the ability of the mRNA to direct synthesis of functional glutamate receptors. If a positive clone is found, the individual λZAP cDNA clone is isolated by subdividing the pool until the functional clone is isolated. (See Example V, below, for a discussion of how this approach was used to isolate the GluR1 clone.)

A second approach that can be used to evaluate positive clones is to analyze each insert individually. Although this is tedious, the "individual clone" approach has the advantage that initially it does not require functional expression. When the "individual clone" approach is used, each clone is plaque purified and the cDNA insert is analyzed individually. This is facilitated by the fact that, at least in the λZAP cDNA system, the cDNA is cloned into a cassette flanked by the bacteriophage f1 origin of replication. The cDNA is contained within a pBluescript plasmid which can be rescued from the λZAP bacteriophage by helper infection. Once this is done, the cDNA is in the small pBluescript plasmid (which is much easier to work with than the much larger λ-bacteriophage). Sense or antisense RNA is made from the cDNA insert in the pBluescript plasmid using either the T3 (sense) or T7 (anti-sense) promoter.

cDNA inserts can also be analyzed by mapping with restriction enzymes. For example, the cDNA inserts are cut with frequent cutting restriction enzymes, and the resulting fragments size fractionated on a gel. Subsequently, the fragments are transferred to a filter for Southern blot analysis. The filters are hybridized with a probe made from DNA encoding known glutamate receptor subunits, e.g., GluR1, GluR2, GluR3, GluR5, GluR5, GluR6 or GluR7. The hybridizing fragments from each clone are subcloned into the single-stranded vector M13 (mp18 or mp19), and the fragments sequenced. DNA sequencing is performed using standard techniques, such as the dideoxynucleotide chain termination method of Sanger et al. Proc. Natl. Acad. Sci. USA 74:5463 (1977), or an automatic sequencer such as one manufactured by Applied Biosystems. The sequence is preferably analyzed by computer using software such as the programs developed by Intelligenetics, Staden and the University of Wisconsin.

mRNA made from full-length or nearly full-length clones are expressed in the oocyte system and the functional properties of the new receptors are characterized. If a clone is not functional when expressed by itself, it is tested in the presence of mRNA made from other candidate clones.

Example IV

Expression Cloning and Assay in XenoPus Oocytes

This assay is an adaptation of the assay of Masu et al., Nature 329:836 (1987). It depends upon the fact that when foreign mRNA is injected into Xenopus oocytes, the mRNA is translated into functional protein.

Either a λZAP cDNA preparation, or a plasmid containing the cDNA to be tested, are cut downstream from the cDNA insert with a restriction enzyme. The post-restriction digest is digested with Proteinase K and then extracted with two phenol: chloroform (1:1) extractions. The resulting DNA fragments are then ethanol precipitated. The precipitated fragments are mixed with either T3 RNA polymerase (to make sense strand), or T7 RNA polymerase (to make anti-sense strand), plus rATP, rCTP, rGTP, rUTP, and RNase inhibitor. Simultaneously, the RNA transcripts are capped with a sodium diguanosine triphosphate [G(5')ppp(5')G] cap. The water used for the above procedures is treated with diethylpyrocarbonate to inactivate RNases.

The in vitro synthesized mRNA transcripts are injected into Xenopus oocytes. 50 nl of an RNA solution, 0.2–0.6 mg/ml, is injected into the stage V oocytes. The injected oocytes are incubated at 16° C. in Barth's medium for 2–7 days before they are analyzed for the presence of functional receptors.

Voltage recordings are made by penetrating the oocyte with a micro-electrode filled with 3M KCl and connected to the bridge circuit of an appropriate voltage clamp unit, e.g., the Dagan 8500 voltage clamp unit. Voltage recordings are preferably obtained with two electrodes, a voltage electrode filled with 3M KCl and a current electrode filled with 0.25 M CsCl, 0.25 M CsF and 50 mM EGTA (ethylene glycol tetraacetic acid). Example VI provides a discussion of results of recordings from oocytes injected with RNA from GluR1 cDNA encoding a KA/AMPA glutamate receptor.

Oocytes employed herein are obtained from ovarian tissue from anesthetized adult female Xenopus. The ovarian tissue is treated with collagenase, 2 mg/ml, for two hours and then the ovarian epithelium and follicular cells are dissected away.

Example V

Expression Cloning of the GluR1 Receptor

Xenopus oocytes were injected with poly(A)⁺ RNA isolated from rat forebrain. 2–10 days later, the oocytes were tested electrophysiologically for their ability to respond to selective agonists for glutamate receptor subtypes. Both glutamate and quisqualate induce membrane depolarizations. These responses display a biphasic pattern composed of a fast acting, smooth (presumably ligand-gated ion channel) response, and a longer lasting, fluctuating, (probably second-messenger mediated) response. NMDA and KA elicited smooth responses with fast onsets, while APB gave no response.

A directional cDNA library (λZAPII RTB1; complexity: 8×10$^5$ elements), consisting of 18 independent sublibraries of 44,000 clones each, was constructed from this poly(A)$^+$ RNA using the bacteriophage expression vector λZAPII. A pool of in vitro transcripts, comprised of transcripts made separately from all 18 amplified sublibraries, was injected into oocytes. Small depolarizations (1–3 mV) were seen in voltage recordings from oocytes challenged with 100 μM kainate 10 days after injection. No responses to NMDA or quisqualate were detected. Neither uninjected oocytes nor water-injected oocytes showed any responses to glutamate receptor agonists. Subsequently, pools of 44,000 clones (=the single sublibraries), 4,000, 400 and 40 clones were tested. In each of these tests at least one pool responded to KA.

The following criteria were used throughout the screening procedure to assure that the very small responses observed initially were not recording artifacts: (a) responses in a given oocyte were reproducible, (b) responses were fast (within one second of agonist application), (c) responses were readily reversible upon superfusion of the oocyte with control Ringer solution, (d) 10 μM domoate gave a response similar to the one elicited by 100 μM kainate.

The pools yielding the largest responses at each stage were selected for further subdivision. The clones in the final positive pool of 40 clones were analyzed for their insert size, and the 12 clones with the largest inserts (all>2 kb) were tested individually for their ability to direct the synthesis of a functional kainate receptor. Only one clone, carrying a 3.0 kb insert, was found to elicit kainate responses and was named λZAPII-GluR1.

Example VI

Electrophysiological and Pharmacological Characterization of the GluR1 Clone

The plasmid pGluR1 was subsequently rescued from bacteriophage λZAPII-GluR1. Upon transcription and translation in vitro, the translation product of sense RNA (but not antisense RNA) induced kainate responses when injected into oocytes. The GluR1 translation product from as little as 10 pg of GluR1 sense transcript gave detectable responses to 100 μM KA under voltage-clamp conditions (−70 mV holding potential).

In order to rule out the possibility that GluR1 codes for a transcription factor, oocytes injected with pGluR1 in vitro transcripts were kept in medium supplemented with 50 μg/ml actinomycin D to inhibit endogenous transcription. These oocytes exhibited the same responses to kainate as those kept in control medium. Therefore, injection-induced transcription from the oocyte genome does not contribute to the observed responses.

L-glutamate evoked much smaller responses than did KA, and even at 1 mM elicited only 50% of the depolarization seen with 30 μM KA. This is consistent with the observation that glutamate is only a weak agonist for the KA receptor subtype [Monaghan et al., Nature 306:176 (1983)]. Other glutamate receptor agonists such as NMDA, quisqualate and L-aspartate evoked no responses when applied at 150 μM, 10 μM, and 100 μM, respectively. Unrelated neurotransmitter receptor agonists such as glycine, γ-aminobutyric acid (GABA$_A$), serotonin and nicotine also failed to evoke responses, even when tested at concentrations as high as 1 mM. Glycine did not potentiate the KA response. Dose-response curves for KA and domoate were recorded and EC$_{50}$ values of 39 μM and 1.8 μM, respectively, were derived. The average reversal potential was 10 mV, as extrapolated from current responses to 10 μM kainate obtained at a series of holding potentials between 0 and −130 mV. Responses to KA did not desensitize, even after prolonged (up to 10 minutes) superfusion with high concentrations (100 μM) of agonist.

Similarly, the pharmacological profile of GluR1, as revealed by the inhibiting properties of various known glutamate receptor antagonists (see Table 2), is consistent with previous reports for KA receptors in systems where total poly(A)$^+$ RNA was used as a source of kainate receptor message [Hirono et al., Neurosci. Res. 6:106 (1988); Lerma et al., Proc. Natl. Acad. Sci. USA 86:2083 (1989)].

As used herein, the term antagonist refers to a substance that interferes with receptor function. Antagonists are of two types: competitive and non-competitive. A competitive antagonist (also known as a competitive blocker) competes with an agonist for overlapping binding sites. A non-competitive antagonist or blocker inactivates the functioning of the receptor by binding to a site on the receptor other than the agonist binding site.

TABLE 2

Pharmacology of the Glutamate Receptor Encoded by GluR1: Properties of various Glutamate Receptor Antagonists as Measured in Oocytes Injected With GluR1 in vitro RNA$^a$

| Compound Tested$^b$ | Compound Alone (%)$^c$ | Compound Plus Kainate (%)$^d$ |
|---|---|---|
| kainate (agonist control) | 100.0 | 100.0 |
| Kynurenic acid | 3.4 ± 0.2 | 9.6 ± 1.3 |
| γ-DGG | −0.1 ± 0.5 | 30.8 ± 1.1 |
| GAMS | 1.0 ± 0.6 | 30.7 ± 1.1 |
| GDEE | 24.8 ± 5.7 | 97.8 ± 6.6 |
| PDA | 2.5 ± 0.7 | 31.3 ± 2.0 |
| APV | 3.1 ± 1.4 | 73.7 ± 3.2 |
| CPP | 9.1 ± 0.7 | 78.8 ± 0.9 |

$^a$Oocytes had been injected with 1.25 ng of GluR1 in vitro sense RNA 3 days prior to the recording. The oocytes were voltage-clamped at −70 mV, and the test compounds (all at 1 mM, except kainate, which was 30 μM) applied by rapid superfusion, with 5 minute intervals between drugs. Peak currents were recorded; each number represents the average of 3 recordings from 3 different oocytes, ± SEM. The 100% current response corresponds to 40–200 nA, depending on the oocyte.
$^b$ = Abbreviations for the compounds used refer to: γ-DGG means γ-D-glutamylglycine; GAMS means γ-D-glutamylamino-methyl-sulphonate; GDEE means glutamate diethyl-ester; PDA means 2,3-cis-piperidine dicarboxylic acid; APV means 2-amino-5-phospho-novaleric acid; CPP means 3-(2-carboxypiperazin-4-yl)propyl-1-phosphate.
$^c$ = % of the response evoked by 30 μM kainate immediately before drug application.
$^d$ = % of the response seen with 30 μM kainate alone immediately before application of drug/kainate mixture Of all the compounds tested (each at 1 mM), the road specificity glutamate receptor antagonist kynurenic acid clearly was the most potent inhibitor of the kainate-evoked depolarizations in oocytes injected with GluR1 RNA synthesized in vitro. To a lesser extent, γ-DGG, reported to preferentially block KA and NMDA receptors but not quisqualate receptors [Davies and Watkins, Brain Res. 206:173 (1981)], inhibited kainate responses, as did GAMS, which reportedly prefers KA and AMPA receptors [Fagg, Trends Neurosci. 8:207 (1985)]. Similarly, PDA, which is known to block all subtypes of glutamate receptors [Foster and Fagg, Brain Res. Rev. 7:103 (1984)], blocked the GluR1 response. GDEE, which is thought to preferentially inhibit AMPA-type glutamate receptors [Foster and Fagg, supra], did not block the response significantly, but instead displayed weak agonist properties. The NMDA receptor antagonists APV and CPP, as well as NMDA itself, slightly inhibited the KA responses, thus acting as weak antagonists. They did not show any agonist properties.

Taken together, the electrophysiological properties observed in oocytes injected with GluR1 transcript, as well as the observed pharmacological properties, indicate that GluR1 represents a functional KA receptor indistinguishable from the one observed in oocytes injected with total poly $(A)^+$ RNA. Thus, the single protein subunit encoded by GluR1 is sufficient to form an active receptor-ion channel complex.

Example VII

Sequencing and Primary Structure of GluR1

The cDNA insert of the plasmid pGluR1 was subcloned into M13mp19 and sequenced (see Sequence ID No. 1). An open reading frame of 2721 bp was found within the total length of 2992 bp. The predicted protein consists of 889 amino acids, with a calculated $M_r$ (of the non-glycosylated form of the receptor subunit) of about 99.8 kD. The deduced protein sequence contains a putative signal peptide of 18 amino acids at its N-terminus, with a predicted cleavage site that conforms to empirical rules [von Heijne, Nucl. Acids Res. 14:4683 (1986)]. The N-terminus of the protein therefore is expected to be located extracellularly. Nucleotides 198 to 251 encode the putative signal peptide, and bases 1 through 197 represent a 5'-untranslated region. At the 3'-terminus of the clone, 71 nucleotides of untranslated sequence were found.

The deduced amino acid sequence for GluR1 is shown in Sequence ID No. 1, along with the nucleotide sequence. The numbering for the amino acid sequence starts with the first residue of the precursor protein, with the first residue of the mature protein being residue 19 (following cleavage of the putative signal sequence). Possible extracellular N-glycosylation sites are present at amino acid residues 63, 249, 257, 363, 401, and 406. The region between amino acids 107–131 bears some resemblance to the ligand-gated ion channel signature postulated by some workers [Grenningloh et al., Nature 330:25 (1987); Barnard et al., TINS 10:502 (1987)]. Sequence comparisons with other sequenced ligand-gated ion channels, the nicotinic acetylcholine receptors, $GABA_A$ receptors and glycine receptors, reveals little overall homology.

The insert cDNA of the bacteriophage clone λZAPII-GluR-K1 was cut out with EcoRI/XhoI, blunt-ended and subcloned into the SmaI-site of the bacteriophage vector M13mp19 [Messing et al., Proc. Natl. Acad. Sci. USA 74:3642 (1977)], yielding clones with both orientations of the cDNA. Overlapping deleted subclones were constructed for each strand orientation using the Cyclone™ kit from United States Biochemical Corporation (Cleveland, Ohio). Single-stranded sequencing by the dideoxynucleotide chain-termination method [Sanger et al., Proc. Natl. Acad. Sci. USA 74:5463 (1977)], was carried out with all 45 subclones, and additionally, 10 oligonucleotide primers were synthesized to facilitate sequencing across areas where compressions or gaps were encountered in the sequences derived from the deletion subclones. Complete sequences for both strands were thus obtained. IntelliGenetics software packages (IntelliGenetics version 5.0, and PC/Gene™ (IntelliGenetics, Inc., Mountain View, Calif.) were used for analyzing sequences.

All ligand-gated ion channel subunits sequenced prior to the present invention have a conserved extracellular region characterized by 2 cysteine residues spaced 14 amino acids apart from each other, with conserved proline and aspartate residues located 8 and 10 amino acids, respectively, downstream from the first of these two cysteines [Barnard et al., Trends Neurosci. 10:502 (1987)]. This hypothetical signature for neurotransmitter receptor-channel complexes is poorly conserved in the protein encoded by GluR1. The proline and aspartate residues are present, but the first cysteine residue is located only 7 residues upstream from the proline residue, and the second cysteine residue is absent.

A hydropathy plot analysis of GluR1 revealed several regions which are candidates for transmembrane domains (TMDs). The region between amino acids 481 and 827 was notable because its hydropathy profile resembled that seen in the other ligand-gated ion channels: three closely spaced putative TMDs which are separated by ~175 amino acid residues from a fourth putative TMD which is located close to the C-terminus of the protein. Within this region, the following four transmembrane regions are assigned in GluR1: TMD I, located between amino acid residues 481 and 498, TMD II between residues 538 and 556, TMD III between residues 613 and 631, and TMD IV between residues 805 and 825.

FIG. 1a presents a comparison of the extracellular region located between amino acid residues 107 and 124 of GluR1 with the "cys-cys-loop" region found in all other ligand-gated ion channels, showing sequence homology. Sequences of neuronal nicotinic acetylcholine receptor (nAChR) subunits α1, β1, γ, δ are from mouse muscle [Heinemann et al., Molecular Neurobiology: Recombinant DNA Approaches (ed. Heinemann, S. & Patrick, J.) 45–96 (Plenum Press, New York, 1987)], those of nAChR subunits α2, α3, α4, β2, β3, and β4 are from rat brain [Deneris et al., J. Biol. Chem. 264:6268 (1989); Duvoisin et al., Neuron 3:487 (1989)]. $GABA_A$ subunits α and β are from calf brain [Barnard et al., Trends Neurosci 10:502 (1987)]. GlyR 48k is the $M_r$=48 kDa subunit of the glycine receptor from rat brain [Grenningloh et al., Nature 328:215–220 (1987)]. Boxed amino acid residues are found at identical positions in GluR1 as well as in at least one of the other receptor sequences. One gap has been introduced arbitrarily.

FIG. 1b presents a comparison of the putative TMD II region of GluR1 with hypothetical TMD II regions of other ligand-gated ion channels [Barnard et al., Trends Neurosci. 10:502 (1987); Deneris et al., J. Biol. Chem. 264:6268 (1989); Duvoisin et al., Neuron 3:487 (1989); Grenningloh et al., Nature 328: 215 (1987); Heinemann et al., in: Molecular Neurobiology; Recombinant DNA Approaches (ed. Heinemann, S. & Patrick J.) 45–96 (Plenum Press, New York, (1987)]; suggesting protein sequence conservation.

Example VIII

Isolation and Characterization of GluR2 and GluR3 cDNA clones encoding the GluR2 and GluR3 genes were isolated from an adult rat forebrain library using a low-stringency hybridization screening protocol (see Example II) and a radiolabeled fragment of the GluR1 cDNA as probe. Sequence ID Nos. 3 and 5 show the nucleotide and derived amino acid sequences of clones λRB14 (GluR2) and λRB312 (GluR3), respectively. The calculated molecular weights for the mature, non-glycosylated forms of GluR2 and GluR3 are 96,400 daltons (862 amino acids) and 98,000 daltons (866 amino acids), respectively. Potential N-linked glycosylation sites occur in the GluR2 protein at Asn-239, Asn-359, Asn-381, Asn-406, and Asn-851 and in the GluR3 protein at Asn-37, Asn-243, Asn-363, Asn-374, and Asn-394. Like GluR1, the hydrophobicity profile for both GluR2 and GluR3 reveals five strongly hydrophobic regions: one such domain is located at the amino terminus of each protein and has characteristics of a signal peptide, while four additional hydrophobic regions presumably form membrane-spanning regions (MSR I-IV) and are located in the carboxy-terminal domain of each polypeptide.

FIG. 2A is an alignment of the deduced amino acid sequences for the proteins encoded by the GluR1, GluR2, GluR3, GluR4 and GluR5 genes. In the figure, identical residues in all compared sequences are boxed, with spaces introduced as appropriate to maximize homology. Predicted signal peptides and four proposed membrane spanning regions (MSR I-IV) are indicated. The hatched line denotes the insertion of 15 amino acid residues found in the GluR5-1, but not in the GluR5-2 protein. As the aligned sequences demonstrate, there is significant sequence identity between GluR1 and both GluR2 (70%) and GluR3 (69%) as well as between GluR2 and GluR3 (74%; see also Table 1). The sequence identity is most pronounced in the carboxy-terminal half of each protein.

FIG. 2B is a comparison of the deduced amino acid sequences for the signal peptides encoded by the GluR1, GluR2, GluR3, GluR4, GluR5, GluR6 and GluR7 genes.

Example IX

Electrophysiological Comparison: GluR1, GluR2 and GluR3

Figures 2, 6:
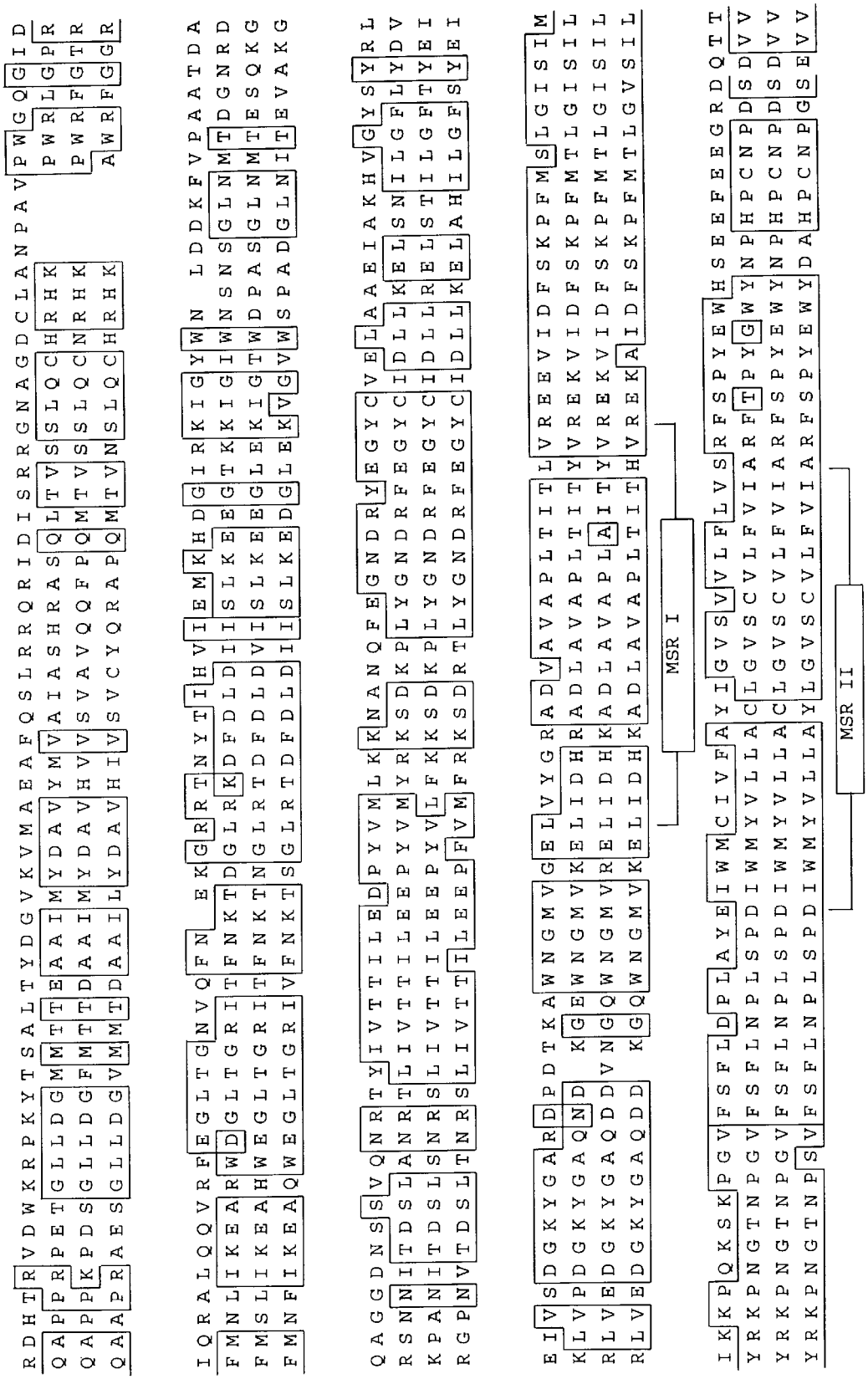
FIG. 6 presents an alignment of the deduced amino acid sequences of the rat glutamate receptor subunits GluR1, GluR5 and GluR6. The GluR5 clone GluR5-1 (without a 15 amino acid insert) is used for the alignment [see Bettler et al., Neuron 5: 583–595 (1990)]. Positions with amino acids identical between at least two proteins are enclosed and shaded. The predicted signal peptide and membrane spanning regions (MSR) are indicated [see Devereux et al., Nucl. Acids Res. 12: 387–395 (1984)]. Numbers indicate positions in the mature subunits.
Figures 3, 6:
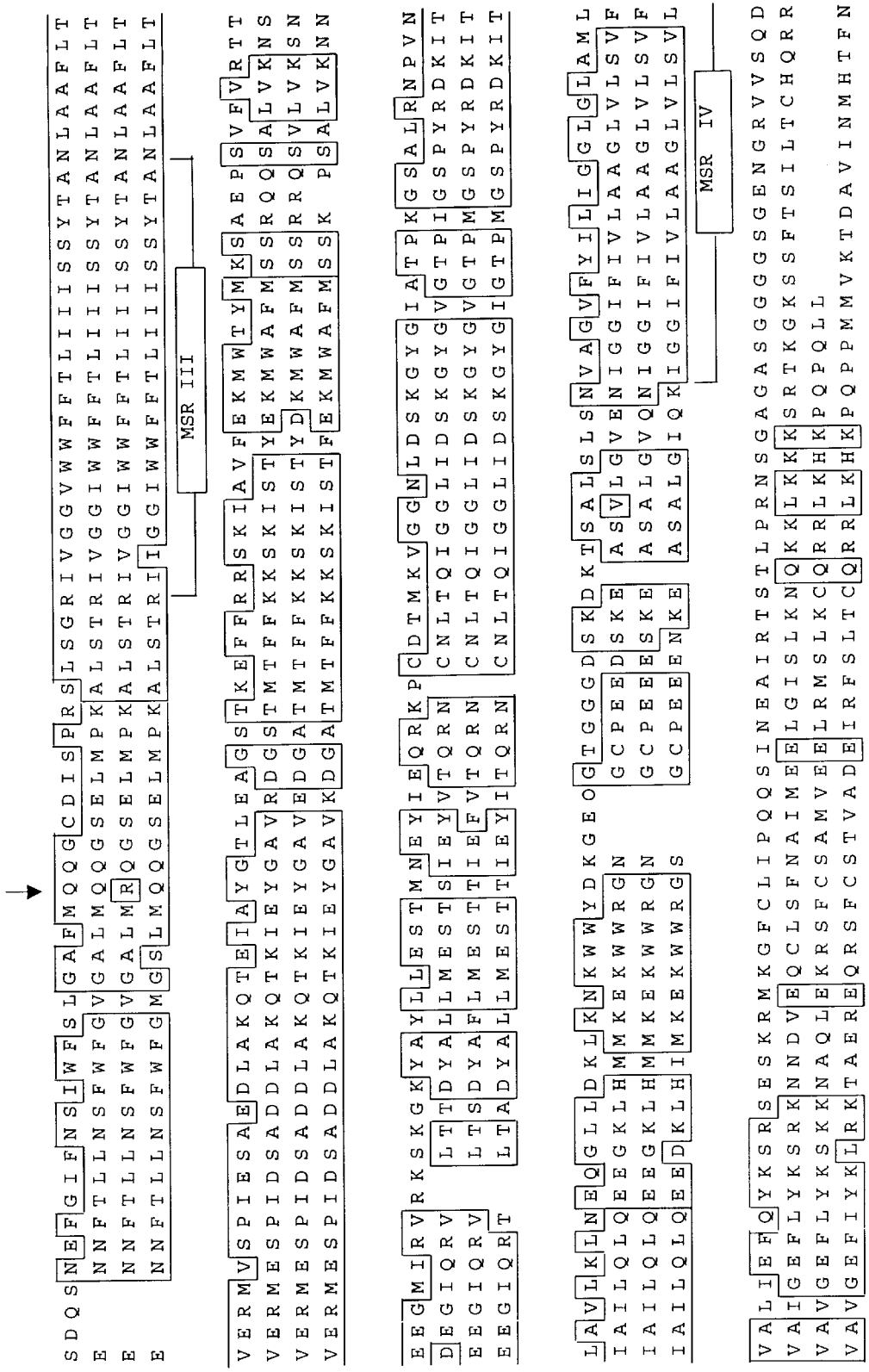

Based on the strong sequence similarity between the proteins encoded by GluR1, GluR2 and GluR3, the following experiments were conducted to determine if the GluR2 and GluR3 proteins might function as homomeric, kainate-sensitive ion channels in Xenopus oocytes (as is the case with GluR1). Thus, oocytes were injected with in vitro synthesized RNA transcripts derived from individual cDNA clones. FIG. 3 presents a comparison of current responses measured in Xenopus oocytes injected with individual GluR1, GluR2 and GluR3 subunit RNAs or rat brain hippocampus poly(A)$^+$ RNA. FIG. 3A shows responses of oocytes to 100 mM KA measured 3 days after injection of individual GluR1 (2 ng), GluR2 (10 ng) or GluR3 (2 ng) RNA. The insert shows examples of voltage recording traces obtained from such oocytes except that the GluR2 response was obtained 5 days after injection of 25 ng RNA. The figure further shows that both GluR2 and GluR3 injected oocytes depolarize in response to batch application of 100 $\mu$M KA.

The amplitudes of the KA responses were not equivalent for the three glutamate receptor subunits: with equal amounts of injected RNA (2 ng), responses in GluR3 RNA-injected oocytes were invariably larger than GluR1 responses. KA-invoked depolarizations in GluR2-injected oocytes were the weakest and could only be detected in oocytes injected with much larger amounts of RNA (10 to 25 ng).

Figure 3B:
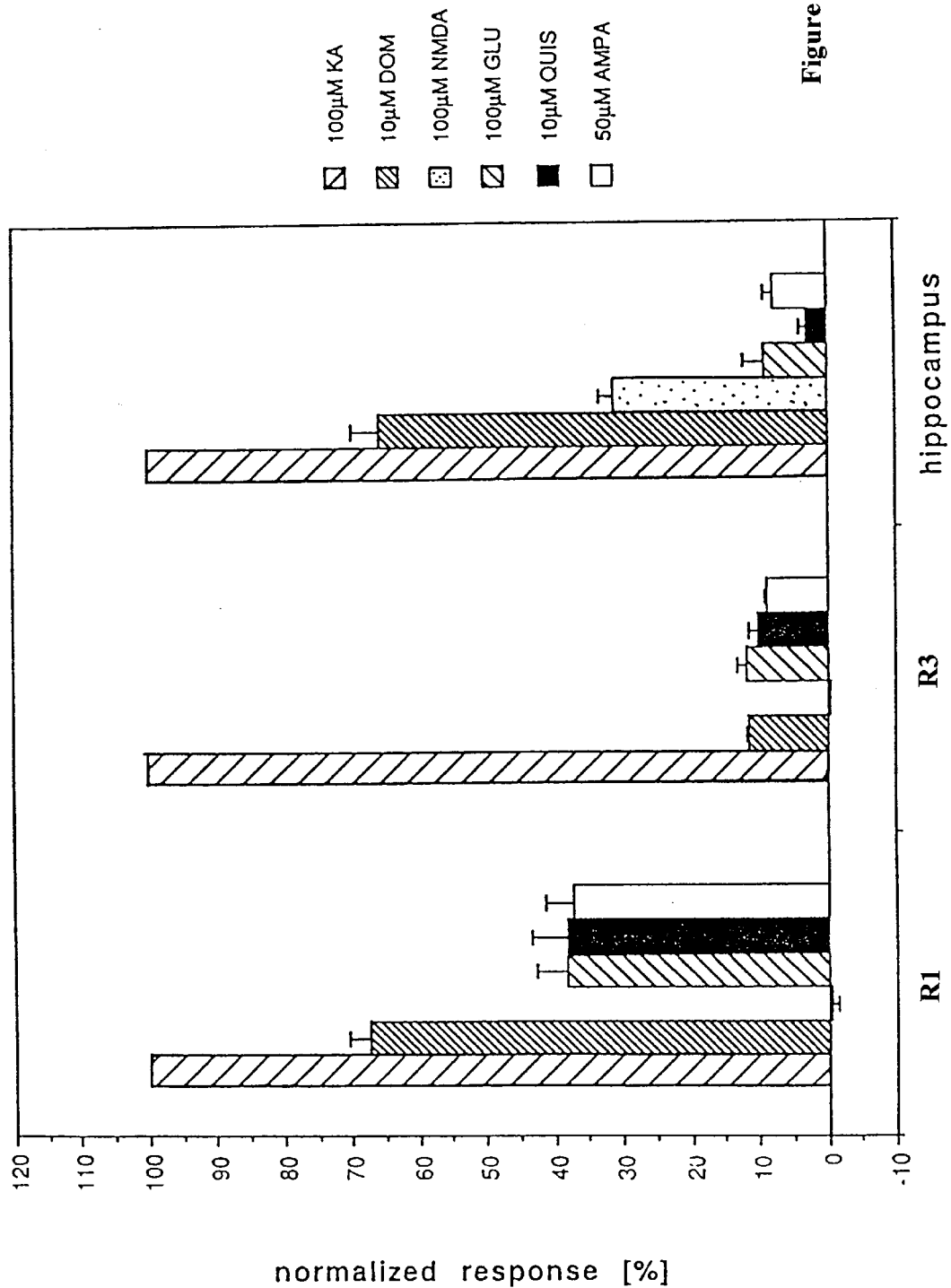

The data in FIG. 3B represent the responses of oocytes to the indicated agonists measured 3 days after injection with GluR1 (2 ng) or GluR3 (2 ng) RNA or adult rat brain hippocampus poly(A)$^+$ RNA (~50 ng). All values are normalized to the response obtained with 100 mM KA and are presented as the mean±S.E.M. with n≧3 for all measurements. All oocytes were voltage-clamped to −70 mV and recordings were performed as described by Hollmann et al., Nature 342:643 (1989). The data show that, in addition to KA, oocytes injected with GluR1 or GluR3 RNA also respond to QUIS (10 $\mu$M), AMPA (50 $\mu$M), and glutamate (GLU, 100 $\mu$M). No detectable responses were obtained with NMDA (30 $\mu$M plus 10 $\mu$M glycine) or APB (50 $\mu$M). Responses obtained from oocytes injected with GluR2 RNA were too small for reproducible quantitation and were, therefore, excluded from the analysis. For GluR1-injected oocytes, the responses to AMPA and QUIS were typically 35–40% of the maximal KA response, while for GluR3-injected oocytes they were about 10% of the KA response. Relative to KA, the response of GluR1 to domoic acid (DOM, 10 $\mu$M) is about 6-fold greater than that seen for GluR3. Taken together these data demonstrate that receptors assembled from GluR1 or GluR3 subunits are pharmacologically distinct. Furthermore, the observation that homomeric GluR1 and GluR3 receptors respond to both QUIS and AMPA, albeit with reduced efficiencies, provides direct evidence that KA, QUIS and AMPA can bind to the same glutamate receptor polypeptide.

FIG. 3B also shows that the pharmacological profile of oocytes injected with individual GluR1 or GluR3 subunit RNA is significantly different than that seen in oocytes injected with rat brain hippocampus poly(A)$^+$ RNA. This suggests that the response seen in oocytes injected with hippocampus RNA is mediated by heteromeric glutamate receptors assembled from various combinations of GluR1, GluR2 and GluR3 subunit polypeptides. This suggestion is supported by the fact that all three GluR subunit genes are actively transcribed in the hippocampus.

Example X

Pharmacological Comparison of GluR1, GluR2 and GluR3

This example addresses the question of whether glutamate receptors assembled from mixtures of proteins encoded by the GluR$_1$, GluR2 and GluR3 subunit genes have pharmacological properties significantly different from each other or from those observed for single subunit receptors. FIG. 4 presents a comparison of current responses measured in Xenopus oocytes injected with combinations of GluR1, GluR2 and GluR3 RNAs.

A comparison of the data in FIGS. 3B and 4B suggests that, for the agonists tested, there are few substantial differences in the pharmacology. FIG. 4B summarizes the responses of oocytes to the indicated agonists measured 3 days after injection of 2 ng RNA for each of the indicated GluR subunits or 50 ng rat brain hippocampus poly(A)$^+$ RNA. Values have been normalized to the response obtained with 100 mM KA and are presented as the mean±S.E.M. with n≧3 for all measurements. All oocytes were clamped to −70 mV and recordings performed as described by Hollmann et al. [Nature 341:643 (1989)]. Responses to QUIS, AMPA and GLU are, relative to GluR1, significantly reduced in the oocytes expressing the subunit combinations. Except for the NMDA response, the overall agonist profiles for oocytes injected with GluR subunit combinations are more similar to oocytes containing hippocampus poly(A)$^+$ RNA than to those injected with either GluR1 or GluR3 subunit RNA alone.

Example XI

Comparison of KA-Activated Currents Recorded from GluR1, GluR2 and GluR3

Figure 4A:
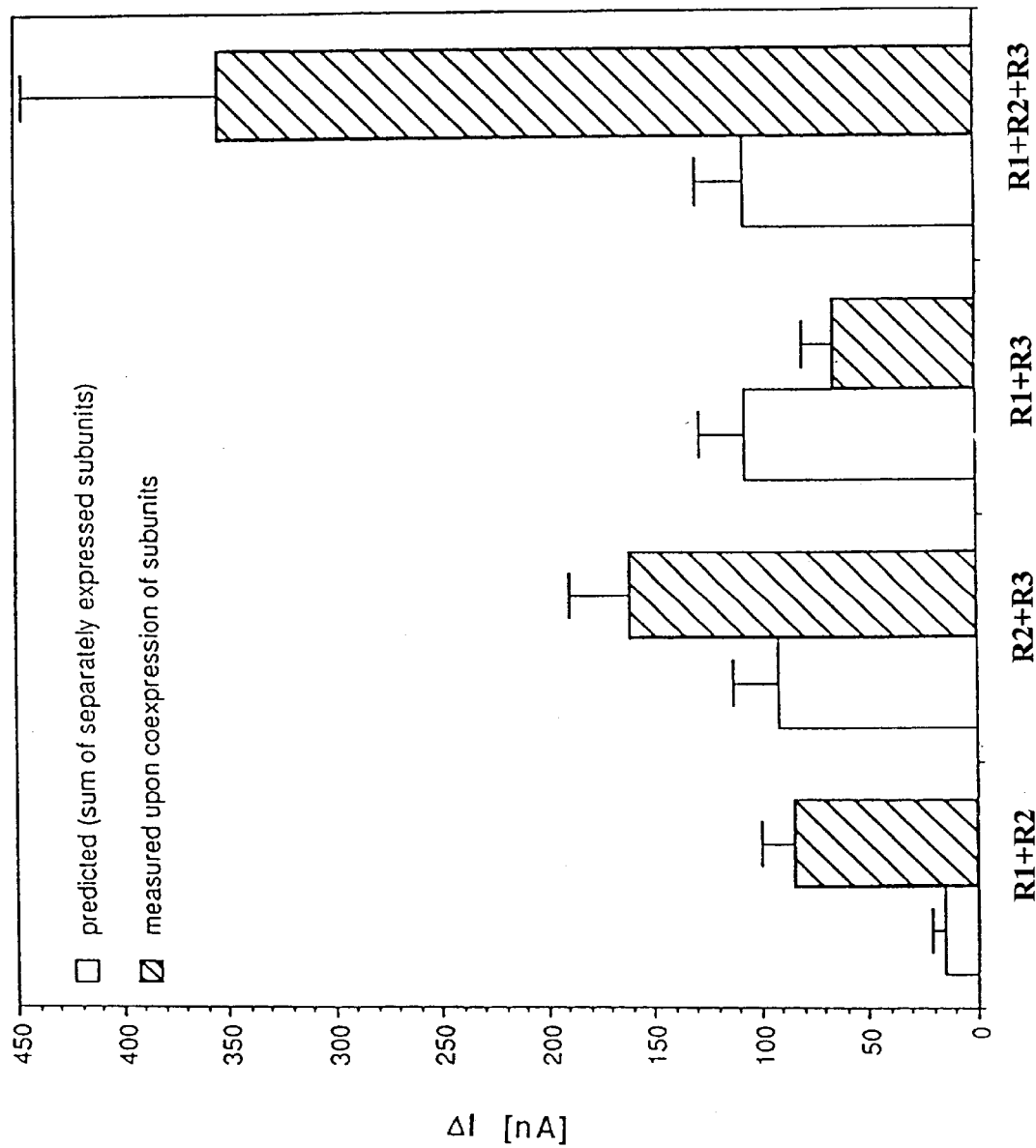
FIG. 4 (A and B) is comprised of two graphs which compare current responses measured in Xenopus oocytes injected with combinations of GluR1, GlUR2 and GluR3 RNAs.

FIG. 4A presents the responses of oocytes to 100 mM KA measured 3 days after injection of 2 ng RNA for each of the indicated GluR subunit combinations. The open columns represent the sum of the responses measured in oocytes expressing the individual GluR subunit RNAS, while the stippled columns show the measured amplitudes after expression of combinations of the GluR subunit RNAs in individual oocytes. The figure compares KA-activated currents recorded from oocytes injected with mixtures of GluR1, GluR2 and GluR3 subunit (stippled columns) with the summed currents measured for the individual subunits (blank columns).

The principle finding is a significant potentiation of KA-evoked currents in oocytes coexpressing glutamate receptor subunits. For example, co-expression of GluR1 plus GluR2 yields an approximately 4-fold increase over the summed responses for singly-injected oocytes; or co-expression of GluR2 plus GluR3 subunits yields an approximately 2-fold increase. Injection of all three subunit RNAs results in an average 2.5 fold-increase in KA-evoked currents.

These results indicate that, in oocytes, individual glutamate receptor subunit polypeptides do not behave in a simple independent fashion. Instead, the various subunits apparently interact with each other, by the generation of heteromeric glutamate receptors with properties which are distinct from the receptors comprised of solitary glutamate receptor subunits.

Example XII

Current-Voltage Relationships for KA-Evoked Responses

This example examines the current-voltage (I/V) relationships for KA-evoked responses measured in oocytes injected with individual GluR subunits, combinations thereof, or hippocampus poly(A)$^+$ RNA.

Figure 5A:
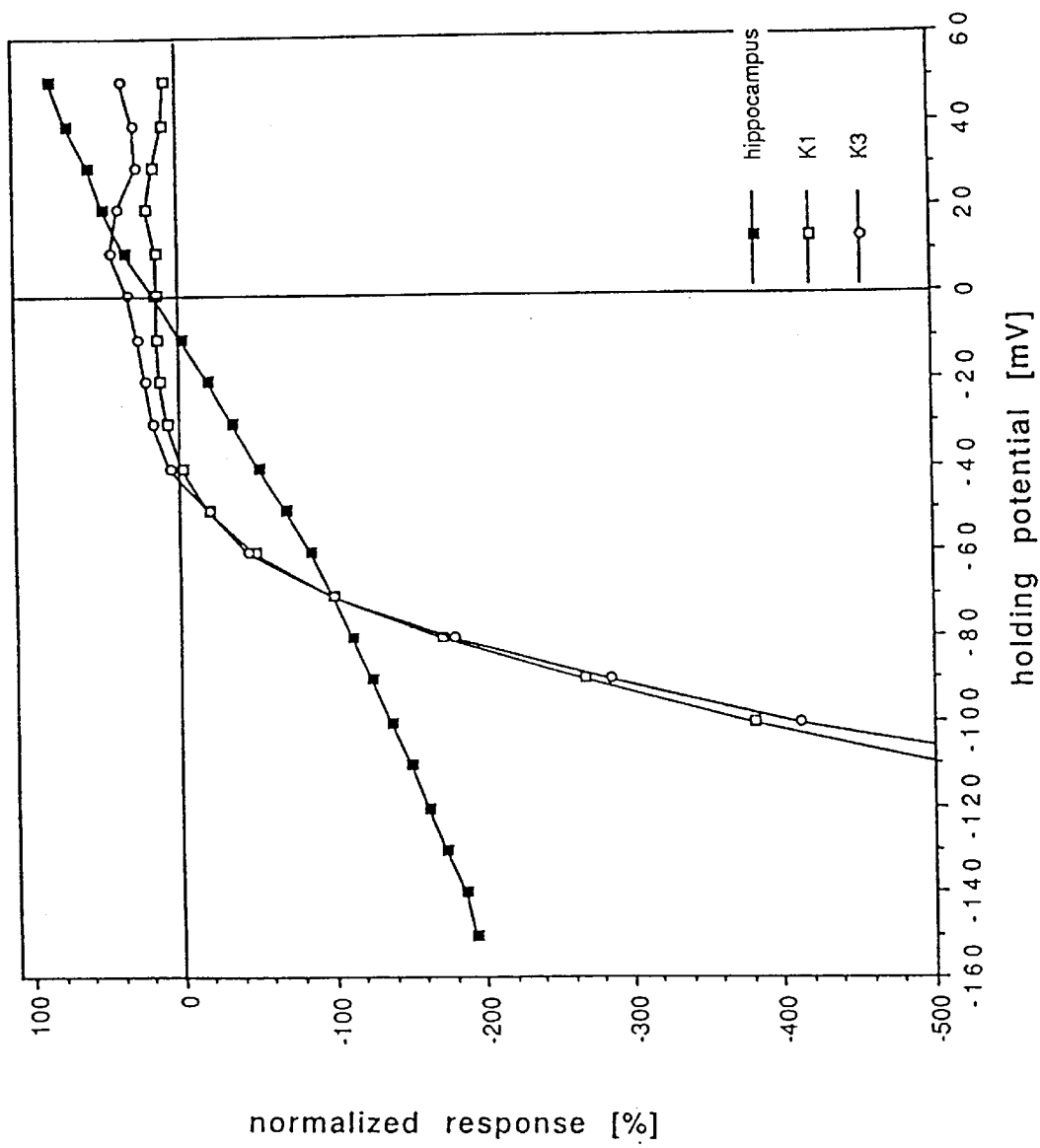
FIG. 5 is comprised of three graphs which illustrate the dependence of the current responses to 100 mM KA upon the membrane potential.

The I/V data are illustrated in FIG. 5 where the dependence of current response to exposure to 100 mM KA upon the membrane potential is shown. Data obtained from oocytes injected with individual glutamate receptor subunit RNAs are shown in panel A, data obtained from oocytes injected with combinations of subunits are shown in panels B and C, and for purposes of comparison, data obtained from oocytes expressing hippocampus poly(A)$^+$ RNA are also shown in panel A, where data obtained from oocytes injected with rat brain hippocampus poly(A)$^+$ RNA (50 ng) are indicated by a Solid Square (■), oocytes injected with GluR1 RNA are indicated by an Open Square (□) or oocytes injected with GluR3 RNA are indicated by an Open Circle (○); (B) oocytes injected with GluR1 plus GluR2 RNAs are indicated by a Solid Square (■) or oocytes injected with GluR1 plus GluR3 RNAs are indicated by an Open Square (□); and (C) oocytes injected with GluR2 plus GluR3 RNAs are indicated by a Solid Square (■) or oocytes injected with all three GluR subunit RNAs are indicated by an Open Square (□). Recordings were made from oocytes 3 days after injection of 2 ng RNA for each GluR subunit. Voltages were stepped by 10 mV between –150 mV and +50 mV; all values are normalized to the response measured at –70 mV.

The KA responses measured in oocytes injected with brain poly(A)$^+$ RNA show an approximately linear I/V relationship with a reversal potential of about –10 mV. This result is in marked contrast to the I/V curves obtained for oocytes injected with single GluR1 or GluR3 subunit RNA. The GluR1 and GluR3 I/V curves show strong inward rectification and reversal potentials near –40 mV. From these data it is clear that the KA-sensitive receptors present in oocytes injected with hippocampus RNA are different from those assembled by oocytes injected with GluR1 or GluR3 subunit RNAs.

Figure 5B:
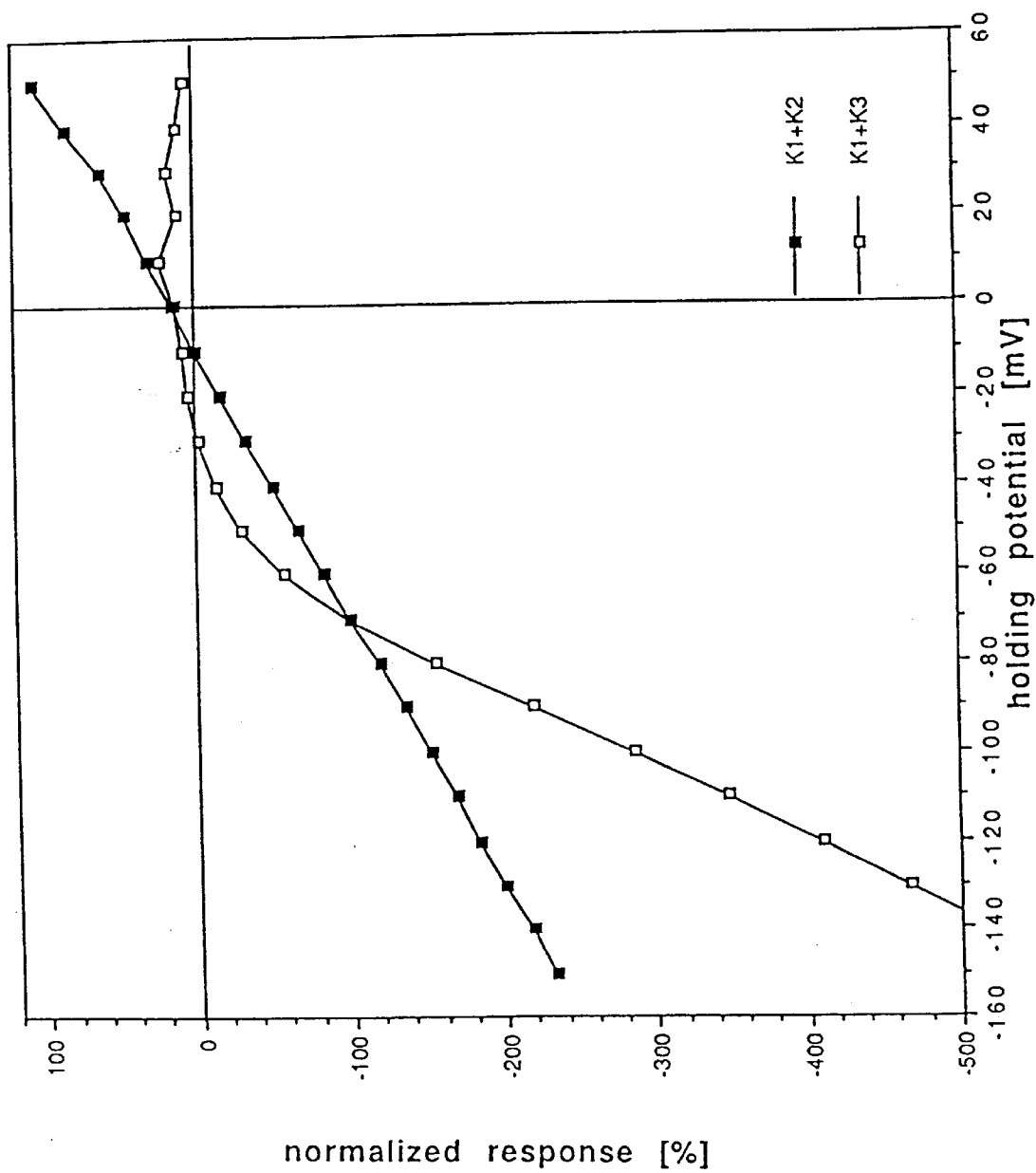

In FIG. 5B the I/V curve for the GluR1 plus GluR2 combination is noticeably different from that observed for the GluR1 subunit alone. Oocytes injected with this pair of RNAs show a nearly linear I/V plot and have a reversal potential of approximately –10 mV. This plot is strikingly similar to that seen with hippocampus RNA-injected oocytes (panel A). In contrast, the I/V curve for the GluR1 plus GluR3 combination is only marginally different from those measured in oocytes expressing the individual subunits.

Figure 5C:
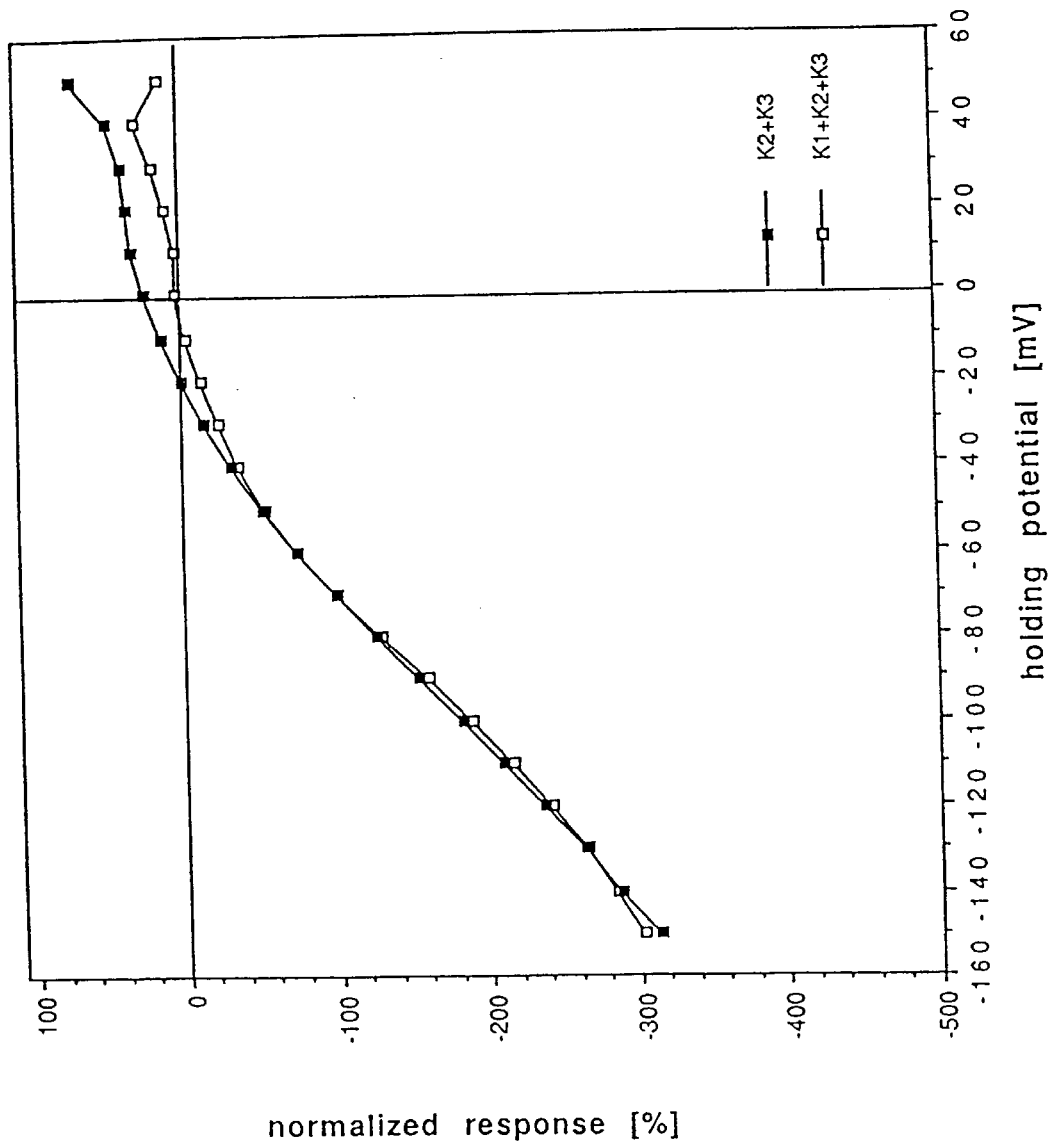

FIG. 5C shows some inward rectification in the I/V curve for the GluR2 plus GluR3 subunit combination, as well as a reversal potential somewhat more negative (–20 mV) than those determined for GluR1 plus GluR2 or hippocampus RNA I/V plots (–10 mV). When all three glutamate receptor subunit RNAs are combined in a single oocyte, the resulting I/V curve approximates that seen for the GluR1 plus GluR2 combination in both reversal potential and slope; however, the responses with the three subunits show a pronounced inward rectification not observed with GluR1 plus GluR2.

Example XIII

Distribution of GluR1, GluR2 and GluR3 mRNA in the Mammalian Central Nervous System The distribution of GluR1, GluR2 and GluR3 RNAs in the adult rat brain was examined to test the hypothesis that proteins encoded by the GluR1, GluR2 and GluR3 genes assemble to form heteromeric glutamate receptors in vivo. This hypothesis would be rendered highly unlikely by a showing that the individual subunit genes are transcribed in different neuroanatomical loci. The distribution of the variou subunit RNAs was examined using radiolabeled anti-sense RNA probes and in situ hybridization histochemistry essentially as described by Deneris et al. [J. Biol. Chem. 264:6268 (1989)]. The hybridization patterns obtained with the $GluR_1$, GluR2 and GluR3 probes were nearly identical, with the strongest hybridization seen in the CA1–CA3 regions of the hippocampus and the dentate gyrus. High-resolution analysis of these areas suggests that the hybridization signal originates in the pyramidal cell layer of regions CA1–CA3 and the granule cell layer of the dentate gyrus. Somewhat weaker hybridization of all three probes was seen in the piriform cortex, caudate-putamen, amygdala, and hypothalamus. Low levels of hybridization were detected in the thalamus, with little or no signal observed in fiber tracts. While differential hybridization was seen in the medial habenula and neocortex, the overall patterns of expression for the $GluR1_1$, GluR2 and GluR3 subunit genes showed substantial concordance.

Example XIV

Isolation of cDNAs for GluR4 and GluR5

GluR4:

Using a fragment of the GluR2 cDNA (nucleotides 1793–2240) as a probe in a low stringency hybridization protocol (as per Example II), several GluR4 and GluR5 clones were isolated from a rat forebrain library (as described in Example VIII). Sequence analysis demonstrated that none of the cDNA clones contained an entire open reading frame. Northern blots with mRNA from different adult rat brain tissues indicated that the GluR4 and GluR5 transcripts were most abundant in the cerebellum. Consequently, the partial GluR4 and GluR5 cDNA clones were used as probes under high stringency screening conditions to isolate cDNAs encoding large open reading frames from an adult rat cerebellum cDNA library constructed in the vector λZAP.

Of the cDNA clones thus isolated, two GluR4-related clones (λCER112 and λCER121B) encoded only portions of the GluR4 gene but possessed sufficient overlap to engineer a full-length, expressible construct in the pBS SK (+) vector (Stratagene Cloning Systems, La Jolla, Calif.). The nucleotide sequence of this GluR4 construct, designated pK45, was determined and is presented in Sequence ID No. 7, along with the deduced amino acid sequence therefor.

The GluR4 mRNA was detected on Northern blots of cerebellum RNA as a 4.6 kb species. The smaller size mRNA may represent splice variants.

GluR5:

Among the 29 GluR5-related cDNAs isolated from the cerebellum library, three clones, specified λRB12, λRBl5 and λRB20, were identified which encode an identical large open reading frame. The sequence of cDNA clone λRB20 (GluR5-1) is shown in Sequence ID No. 9. Cleavage of the assumed signal peptide is predicted to occur between amino acid positions 30 and 31 [von Heijne, Nucl. Acids Res 14:4683 (1986)]. This cleavage site is after a proline residue, which is atypical. The signal peptide is encoded by a fragment of about 30 amino acids. Potential sites of N-linked glycosylation are found at Asn-68, Asn-74, Asn-276, Asn-379, Asn-428, Asn-439, Asn-620 and Asn-766.

λRB15 and λRB12 are shorter than λRB20 at the 5' end. The λRB20 cDNA consists of a 5' untranslated region of 187 bp, a continuous open reading frame of 2760 bp, and a 3' untranslated region of 303 bp. The 5' untranslated region ends with the sequence AAGATGG, which is characteristic of a translational start site.

Three additional cDNA clones originally isolated from the forebrain library were also examined. The sequences of these cDNAs are identical to λRB20 in the predicted translation initiation site region. Sequence analysis revealed that two variants of the GluR5 cDNA are represented in the forebrain and the cerebellum libraries. This heterogeneity derives from the insertion of 45 nucleotides (found in λRB20 and 17 of the 29 GluR5-related cDNA clones isolated). The insertion of 45 nucleotides, as found in λRB20, but not in 12 of the 29 cDNA clones isolated, occurs between nucleotides 1388 and 1434. This insertion does not interrupt the open reading frame. Furthermore, consensus splice donor and acceptor sites are absent [Breathnach and Chambon, Ann. Rev. Biochem. 50:349–383 (1981)], which suggests that the insertion does not arise from an unspliced intron and is, most likely, the result of an alternative splice event. Nucleotide sequence analysis indicates that the two GluR5 variants are otherwise identical.

No cDNA clone was found for the shorter splice variant encoding the entire open reading frame. Therefore a clone (λRBΔ20) was constructed that is missing the 45 nucleotide insertion found in λRB20 (GluR5-1) but is otherwise identical to that clone. The shorter splice variant clone (λRBΔ20) is referred to as GluR5-2. Both λRB20 and λRBΔ20 were used in Xenopus oocyte expression experiments (see Example XVI) and the variant proteins encoded were named GluR5-1 and GluR5-2, respectively.

Northern blot analysis of cerebellum RNA indicated that the major GluR5 mRNA has a size of 6 kilobases.

Example XV

Structural Features of GluR5 cDNA and Protein

Translation of the cDNA nucleotide sequence for GluR5-1 predicts a single long open reading frame of 920 amino acid residues (see Sequence ID No. 9). The GluR5 sequence has overall amino acid sequence identity with each of the KA/AMPA subunits (see FIG. 2, and Table 1). The 15 amino acid insertion in GluR5-1 is unique among the proteins listed, thus the shorter GluR5-2 variant is the counterpart to the KA/AMPA subunits characterized. Table 1 shows that GluR5 is thus far the most dissimilar glutamate receptor subunit identified; and the comparison of GluR5 with the KA/AMPA subunits highlights the most conserved sequence elements (FIG. 2). Within other ligand-gated ion channel families (i.e., the neuronal nicotinic acetylcholine receptors (nAChR), the $GABA_A$ receptors and the glycine receptors), the N-terminal extracellular domain is most conserved while the C-terminal sequences diverge between the membrane-spanning regions (MSR) III and IV. In the glutamate receptor subunit gene family, in contrast, the regions N-terminal of the proposed MSR I [Hollmann et al., Nature 342:643 (1989)], have only 17% identity and are less similar than the regions C-terminal of MSR I which have 45% identity. The 'Cys-Cys loop', a signature for ligand-gated neurotransmitter receptor channel complexes [Barnard et al., Trends Neurosci. 10:502 (1987)] is not conserved in the glutamate receptor subunit family (FIG. 2). The C-terminal half of glutamate receptor subunits is thought to be involved in channel formation and contain the membrane spanning regions (MSR I-IV; FIG. 2). The presumed MSR III is the most conserved continuous sequence, with only one conservative amino acid exchange (Val to Ile) in the GluR5 protein (FIG. 2). As mentioned above, in other ligand-gated channel families the segment between MSR III and IV is divergent in length and sequence. In the glutamate receptor subunit family the similarity in this postulated segment is high (48%) and only GluR5 exhibits a sequence length variation. The KA/AMPA receptors and the GlUR5 protein are generally divergent C-terminal of the proposed MSR IV.

The hydrophobicity plot for GluR5 is similar to those of the KA/AMPA receptors, suggesting a conserved secondary structure in the proposed ion channel forming portion of the protein. However, the N-terminal half of the GluR5 hydrophobicity plot is unusual. In this region, GluR5, as compared to the KA/AMPA subunits, is more hydrophobic and contains several segments that could span the membrane. Based on algorithms that search for membrane-associated helices, four [Rao and Argos, Biochim. Biophys. Acta 869:197–214 (1986)] or seven [Eisenberg et al., J. Mol. Biol. 179:125–142 (1984)] putative transmembrane regions can be assigned to GluR5.

A comparison of the C-terminal regions of all five glutamate receptor subunits with the frog [Gregor et al., Nature 342:689 (1989)] and chicken [Wada et al., Nature 342:684 (1989)] KA binding proteins demonstrates a similar extent of sequence conservation (35–40% amino acid identity). A FASTA search [Pearson and Lipman, Proc. Natl. Acad. Sci. USA 85:2444 (1988)] of the GenBank, EMBL and SWISS-PROT databases with the GluR5 sequence uncovered no significant similarities to other proteins.

Example XVI

Electrophysiological Properties of GluR5 mRNA Injected Oocytes Exposed to L-Glutamate In vitro synthesized GluR5-1 and GluR5-2 cRNAs were individually expressed in Xenopus oocytes. With either cRNA, the glutamate receptor agonists KA (100 MM), AMPA (50 $\mu$M), quisqualate (10 $\mu$M), APB (100 $\mu$M) and NMDA (100 $\mu$M, applied with 10 $\mu$M glycine) did not elicit membrane depolarizations in cRNA injected oocytes.

However, weak membrane depolarizations induced by L-glutamate (100 μM) were recorded in oocytes injected with GluR5-1 cRNA (maximal depolarization 3.5 mV) and GluR5-2 cRNA (maximal depolarization 4.5 mV). Significantly stronger membrane depolarizations were not found in response to L-glutamate in oocytes co-injected with GluR5-1 and GluR5-2 RNA as compared to oocytes injected with GluR5-2 cRNA alone. For any particular oocyte injected with GluR5-1 or GluR5-2 cRNA, the depolarizations were reproducible, showed fast onset, and were slowly (within 5 minutes) reversed when agonist superfusion was switched to buffer superfusion. Neither un-injected oocytes nor water-injected oocytes showed a response to the glutamate receptor agonists tested. Responses to L-glutamate were recorded in 7 (out of 7) oocytes for GluR5-1 (membrane depolarization 2.29±0.26 mV S.E.M.) and 29 (out of 33) oocytes for GluR5-2 (2.27±0.19 mV S.E.M).

Example XVII

Distribution of GluR4 and GluR5 mRNA In the Developing Central and Peripheral Nervous Systems For the developmental study of GluR4 and GluR5 gene expression, sections of mice from embryonic day 10 (E10) through post natal day 21 (P21) were analyzed using in situ hybridization and histochemistry.

In the entire central nervous system (CNS), a diffuse expression of the GluR4 and GluR5 genes was detected at E10. These first hybridization signals originate from postmitotic neurons. This is best demonstrated in the myelencephalon at E12. The ependymal layer is facing the neural canal and contains dividing neuroblasts. No hybridization was detectable in these cells. The postmitotic cells are located in the exterior part of the neural tube and express both genes.

Later in development, transcripts for GluR5 and, to a lesser extent, GluR4 were particularly pronounced in areas where neurons differentiate and assemble into nuclei. These temporal changes in the hybridization pattern were best observed for GluR5 (in the primary sensory nuclei of the medulla oblongata and the nuclei of the pons which hybridized more intensely than surrounding structures at E14). GluR5 gene expression was particularly intense in several discrete brain nuclei, whereas GluR4 gene expression was detectable over the entire rostral and caudal parts of the brain.

During postnatal development, the spatial distribution of GluR4 gene transcripts did not change but usually smaller amounts of mRNA were detectable than at late embryonic stages. In contrast, GluR5 gene expression appeared to become more restricted spatially during development, and transcript levels were down-regulated. Extreme changes in the temporal GluR5 hybridization pattern were apparent in the cerebellar cortex. Until P12, high GluR5 transcript levels were detected in the granular and Purkinje cell layer. Later, the intensity of hybridization signals in the granular cell layer was reduced relative to the Purkinje cell layer and starting at P14, only a faint hybridization signal was detected in the granular cell layer.

In general, those regions of the brain that exhibited a dense labeling during embryonic development also had detectable transcript levels in adults. In P21 animals, the highest GluR4 transcript levels were observed in the cell layers of the olfactory bulb, the hippocampus, the cerebellum and the retina. In the retina, strong hybridization was found in the ganglion cell layer and in the amacrine cells of the inner nuclear layer. No expression was detected in Muller cells. For GluR5, the strongest hybridization signals at P21 were found in the olfactory bulb, the amygdala, the colliculi and some hypothalamic nuclei.

In the developing peripheral nervous system (PNS), the hybridization assays showed that the GluR4 and GluR5 genes are expressed to varying degrees in the cranial ganglia (e.g., trigeminal ganglion, acoustic ganglia), dorsal root ganglia and the mural ganglia of the intestinal organs. Comparable to the CNS, transcripts in the PNS are detected by E10 for GluR4 and by E11 for GluR5. During development, hybridization signals for GluR4 continuously increase until early postnatal stages and then persist with similar intensity in adults. Hybridization signals for GluR5 increase up to E16 and remain with comparable intensity in later developmental stages. In postnatal animals, the dorsal root ganglia (GluR5) and the mural Ganglia of the intestinal organs (GluR4 and GluR5) exhibit higher levels of hybridization than the CNS. High resolution autoradiography in the dorsal root ganglia demonstrates hybridization of the GluR5 probe over neuronal cells whereas satellite cells are unlabeled.

Example XVIII

Distribution of GluR4 and GluR5 mRNA in the Adult Mammalian (Rat) Brain

The distribution of the GluR4 and GluR5 mRNA transcripts in the adult CNS was studied by in situ hybridization. In the forebrain region, high levels of GluR4 transcripts were detected in the CA1 and the dentate gyrus of the hippocampus, in the medial habenula and particularly in the reticular thalamic nucleus. The hippocampus showed only weak expression of the GluR5 gene and no transcripts were detected in the medial habenula. The GluR5 hybridization signal was intense in the cingulate and piriform cortex, several hypothalamic nuclei, the amygdala and the lateral septum. In the cerebellum, the hybridization patterns for GluR4 and GluR5 probes were overlapping but distinct. Both probes were detected at high levels in the Purkinje cell layer. In the granular cell layer the GluR4 probe produced strong labeling, while GluR5 probe labeling was weak.

Example XIX

Isolation of GluR6 and GluR7 cDNA clones encoding the GluR6 and GluR7 genes were isolated from an adult rat forebrain library using a low-stringency hybridization screening protocol (see Example II) and a radiolabeled fragment of about 1.2 kbp (nucleotides 705–2048) of the GluR5 cDNA as a probe. The selected clones were identified by restriction digest map and sequencing.

An adult rat cerebellum cDNA library constructed in λZAP was screened under low-stringency hybridization conditions with the above-described GluR5 cDNA fragment [Bettler et al., Neuron 5: 583–595 (1990)]. A 3kb fragment from a cDNA clone encoding part of the GluR6 open reading frame was used to rescreen the library under high-stringency hybridization conditions. Two clones, RC11 and RC27, possessed sufficient overlap to engineer a cDNA clone encoding the entire open reading frame of the GluR6 protein.

A 4559 base pair cDNA encoding a protein of 884 amino acid residues was engineered from RC11 and RC27. The protein encoded by this cDNA is referred to as GluR6. Sequence ID No. 11 shows the nucleotide and deduced amino acid sequence of the GluR6 clone. The similarity between the hydropathy profile of the GluR6 subunit and those of the GluR1–GluR5 subunits suggests a similar membrane spanning topology.

Another adult rat cerebellum cDNA library was constructed in λZAP and screened under low-stringency hybridization conditions with the above-described GluR5 cDNA fragment. A 2kb fragment from a cDNA clone encoding part of the GluR7 open reading frame was used to rescreen the library under high-stringency hybridization conditions. Two clones, RP52 and RPC44, possessed sufficient overlap to engineer a cDNA clone encoding the entire open reading frame of the mature GluR7 protein.

A 3344 base pair cDNA encoding a protein of 921 amino acid residues was engineered from RP52 and RPC44. The protein encoded by this cDNA is referred to as GluR7. Sequence ID No. 13 shows the nucleotide and deduced amino acid sequence for the GluR7 clone.

The physiological and pharmacological properties of the homomeric GluR6 ion channel were studied in Xenopus oocytes injected with in vitro transcribed RNA. In oocytes held at −100 mV, application of kainate and glutamate evoked inward currents that desensitized in continued presence of agonist. Full recovery from desensitization caused by application of 100 μM kainate for 30 seconds required approximately 15 minutes. Quisqualate activated only small inward currents; however, quisqualate application attenuated a subsequent kainate evoked current. AMPA (100 μM) did not evoke any detectable current, nor did it antagonize a kainate-evoked current when AMPA and kainate were applied together. The AMPA solution used in the experiment did evoke responses in oocytes injected with either hippocampal mRNA or GluR1 RNA (which are both known to respond to AMPA).

Exposure of the injected oocyte to 10 μM concanavalin A (Con A) for 5 minutes efficiently decreases desensitization [see Meyer & Vyklicky, Proc. Natl. Acad. Sci. USA 86: 1411–1415 (1989)] and allows agonist-activated currents mediated by the GluR6 receptor to be more easily studied. Con A treatment increased current elicited by kainate and glutamate by 75 to 150fold compared to the peak current for equimolar concentrations before the treatment. After Con A treatment, the maximal current induced by glutamate (relative to kainate) was 0.56±0.03 and for quisqualate 0.38±0.03. Con A treated oocytes injected with GluR6 RNA responded to kainate, but did not respond to application of 100 μM aspartate, 100 μM NMDA in the presence of 3 μM glycine, or 10–1000 μM AMPA. Furthermore, coapplication of AMPA (100 μM) had no effect on the kainate-evoked (1 μM) responses on Con A treated oocytes. It thus appears that AMPA acts as an agonist on only a subset of the kainate/quisqualate sensitive ionotropic receptors.

Figure 7A:
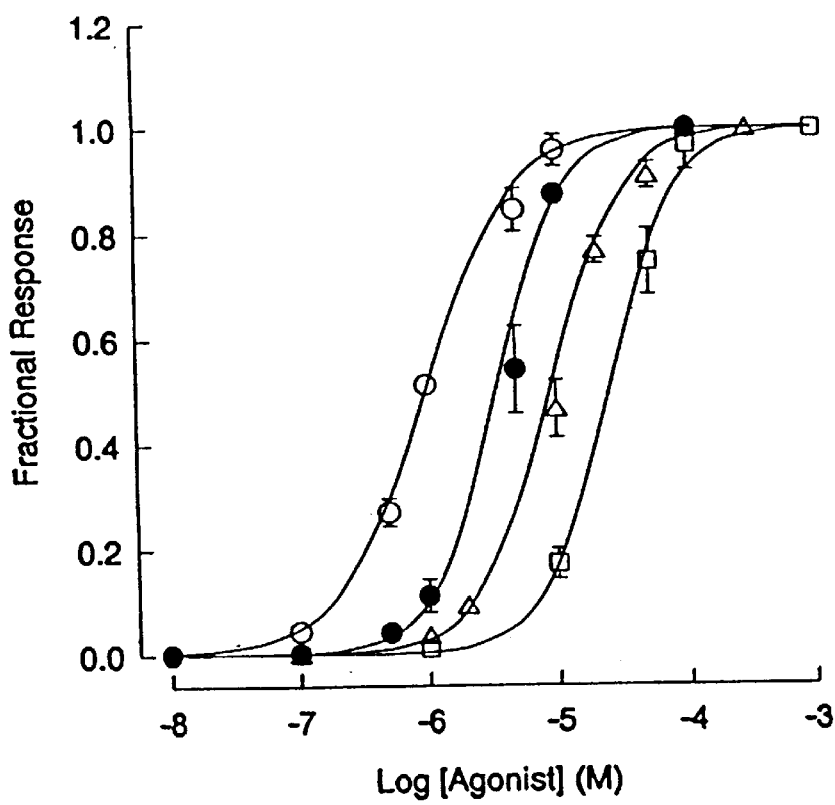
FIG. 7a presents dose response curves obtained on GluR6 injected oocytes.

The dose response curves for activation of the GluR6 receptor were obtained after Con A treatment. Data are summarized in Table 3, and in FIG. 7a, which presents dose-response curves obtained on GluR6 injected oocytes after Con A treatment for kainate (○), glutamate (□), quisqualate (Δ) and kainate in the presence of 10 μM 6-nitro-7-cyano-quinoxaline-2,3-dione (CNQX) (●). All points represent an average of 3–6 independent measurements. Error bars indicate S.E.M.

TABLE 3

$EC_{50}$ and the Maximal Agonist-evoked Current Relative to the Maximal Kainate-evoked Current for Homomeric GluR6 Receptor After Con A Treatment

| Agonist | $EC_{50}$ (μM) | Relative maximal current (±S.E.M.) |
|---|---|---|
| Kainate | 1.0 (0.8–1.3) | 1.00 |
| Quisqualate | 11 (10–13) | 0.38 ± .03 |
| Glutamate | 31 (29–34) | 0.56 ± .03 |

The mean of $EC_{50}$ are based on measurements of 3–6 oocytes. The numbers in parentheses indicate 95% confidence intervals. Relative maximum current maximum agonist-evoked current/maximum kainate-evoked current.

The $EC_{50}$ for kainate (1 μM) is about 35-fold lower than the $EC_{50}$ observed for the homomeric GluR1 ($EC_{50}$=35 μM) receptor [see Hollmann et al., Nature 242: 643–648 (1989); Dawson et al., Mol. Pharmacol. 38: 779–784 (1990)]. The $EC_{50}$ for the GluR6 receptor is 75-fold higher for quisqualate and 10-fold higher for glutamate when compared to the same agonist on the GluR1 receptor. Thus the order of agonist potency for the homomeric GluR6 receptor is:

kainate>quisqualate>L-glutamate.

The order of agonist potency set forth above is similar to the order of binding affinities measured for quisqualate and glutamate as competitive displacers of kainate on kainate binding sites in isolated brain membranes [see Foster and Fagg, Brain Res. Rev. 7: 103–164 (1984)]. This property is clearly distinct from the GluR1 and GluR3 receptors where the relative apparent affinities are:

quisqualate>AMPA>glutamate>kainate.

[See Nakanishi et al., Neuron 5: 569–581 (1990); Boulter et al., Science 249: 1033–1037 (1990); and Foster and Fagg, supra]. Therefore, based on agonist potencies ($EC_{50}$), GluR6 can be considered a kainate receptor within the glutamate receptor family.

CNQX acts as a competitive antagonist of non-NMDA receptors in rat brain neurons [see Verdoorn et al., Mol. Pharmacol. 35: 360–368 (1989)]. CNQX blocked both quisqualate and kainate-evoked responses in oocytes injected with GluR6 RNA. The inhibitory effect of 10 μM CNQX was eliminated at high kainate concentrations, consistent with its competitive mode of action. 10 μM CNQX resulted in a 3.5-fold parallel shift of the kainate dose-response curve compared to the curve obtained in absence of CNQX (see FIG. 7a). Considering the competitive action of CNQX at 10 μM, the $K_i$ for CNQX was calculated to be 4 μM. Thus, CNQX is a less potent blocker of kainate responses at GluR6 receptors than at GluR1 receptors ($K_i$= 0.519 μM) [see Dawson et al, supra] and kainate receptors derived from forebrain mRNA ($K_i$=0.295 μM) [see Verdoorn et al., supra] expressed in oocytes.

Figure 7B:
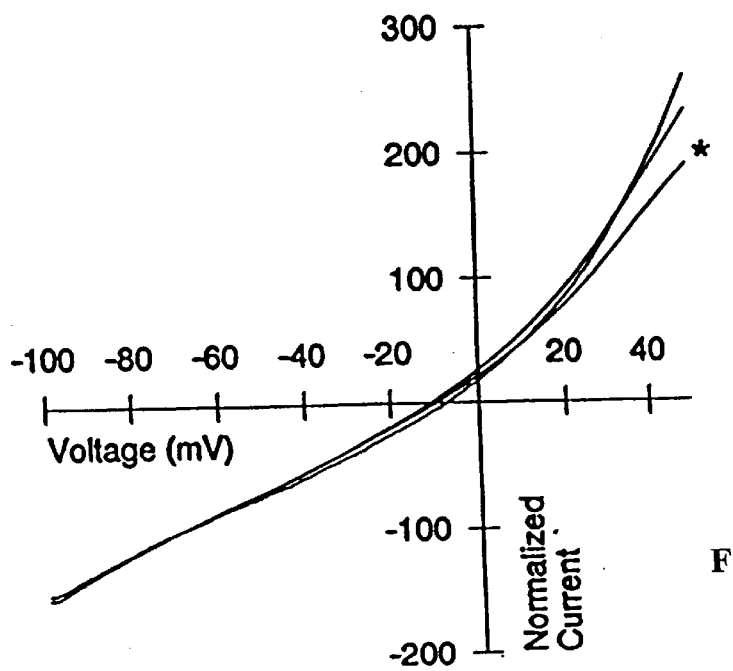
FIG. 7b presents the current-voltage relationship of the homomeric GluR6 receptor evoked by 10 µM kainate before and after Con A treatment. The asterisk indicates the I/V relationship obtained on Con A treated oocytes in a modified frog Ringer solution in which the NaCl was substituted with an equimolar concentration of sodium methanesulfonate. The currents were normalized to the individual currents measured at −70 mV (30 nA and 2.3 µa in Ringer solution before and after Con A treatment, respectively, and 330 nA in the modified Ringer solution).

The current-voltage relationship (I/V) for kainate and glutamate-evoked responses in the presence of Con A and for kainate in the absence of Con A was examined. No qualitative differences were found between Con A-treated and untreated oocytes (see FIG. 7b). The I/V relationships were assessed from 2 s voltage ramps from −100 mV to 50 mV in the presence and absence of agonist. Data were collected and analyzed using the pclamp program set. The I/V relationship exhibited a reversal potential of −10±3 mV and an outward rectification. To analyze whether the outward rectification was an intrinsic property of the channel (or perhaps an activation of endogenous chloride channels activated by a $Ca^{++}$ flux [see Miledi & Parker, J. Physiol. 357: 173–183 (1984)] through the GluR6 ion channel), the kainate-evoked I/V relationship was recorded in a buffer where 95% of the $Cl^-$ ions were substituted by an equimolar amount of methanesulfonate (which is known to shift the chloride reversal potential in a positive direction [see Verdoorn & Dingledine, Mol. Pharmacol. 34: 298–307 (1988)]). No significant change in the reversal potential was observed. Thus, if there is a $Ca^{++}$ flux in Ringer solution, it is not sufficient to activate a $Cl^-$ current. The substitution of $Cl^-$ with methanesulfonate reduced the current 8-fold; this may have been caused by either inhibition of agonist binding or a direct methanesulfonate block of the channel. The latter effect might be potentiated at positive holding potentials.

The expression pattern of the GluR6 gene was studied by in situ hybridization using brain sections from adult mice. The highest levels of GluR6 transcripts were observed in the olfactory lobe, piriform cortex, dentate gyrus, hippocampus, and in the granular cell layer of the cerebellum. In the hippocampus a gradient in hybridization intensities was observed from rostral to caudal areas, with increased intensity in the CA3 region as compared to the CA1 region. The high level of transcripts in the pyramidal cell layer of CA3 and the granule cell layer of the dentate gyrus correlates with the previously observed high level of [$^3$H]kainate binding in the stratum lucidum and the commissural/associational terminal field of the dentate gyrus, respectively [see Foster and Fagg, supra; and Monaghan & Cotman, Brain Res. 252: 91–100 (1982)]. Less intense hybridization signals were observed in the caudate putamen, the zona incerta of the thalamus, the inner and outer layers of cortex, several brain stem nuclei as well as the ganglion cell layer of the retina. In general, areas expressing high level of transcripts correlate well with areas expressing high affinity kainate binding sites.

The properties observed herein for the homomeric GluR6 receptors have not been described in studies performed on neurons. The pattern of the gene expression and the pharmacology of the GluR6 subunit suggest that this subunit might correspond or contribute to the receptor with high affinity for kainate found in the brain.

Example XX

GluR-Related Assays

The GluR cDNAs, mRNAs, proteins and functional fragments thereof, are useful in various assays designed to identify and characterize L-glutamate receptors, agonists and antagonists. For example, the cDNAs are useful as probes to identify additional members of the glutamate receptor gene family. mRNAs transcribed from the DNAs of the invention are especially useful in assays designed to identify and characterize both functional receptors and ligands. This use is especially important for the identification and design of compounds that can affect L-glutamate receptor function.

In an assay for identifying and characterizing functional receptors, mRNA is transcribed from DNAs of the invention (either full length or fragments thereof produced by deletions, substitutions, synthesis, etc.) and then translated to produce GluR proteins. In a presently preferred means for carrying out this transcription and translation, the mRNAs are translated in oocytes, preferably Xenopus oocytes. Alternatively, suitable cultured mammalian cells can be used as hosts for the production of glutamate receptor proteins. Such mammalian cells can be transfected in vitro with DNAs of the invention to yield either stable or transiently transfected cell lines. The expressed glutamate receptor proteins are then exposed to ligands known to functionally bind to and activate glutamate receptors. The physiological characteristics of the glutamate receptor proteins are measured by suitable means (e.g., by electrophysiology), and those that form functional ion channels are concluded to be functional glutamate receptor.

In a related assay designed to identify functional ligands for glutamate receptors, proteins known to functionally bind to glutamate receptor agonist or antagonist compound(s) are contacted with at least one "unknown" or test compound whose ability to effect the ion channel activity of glutamate receptors is sought to be determined (in the optional presence of a known glutamate agonist, where antagonist activity is being tested). The electrophysiological properties of the glutamate receptors are measured following exposure to the test compound(s), and those that affect the ion channel response are concluded to be functional ligands for glutamate receptors.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

SUMMARY OF SEQUENCES

Sequence ID No. 1 shows the nucleotide and deduced amino acid sequence of the clone GluR1.

Sequence ID No. 2 is the deduced amino acid sequence of the clone GluR1.

Sequence ID No. 3 shows the nucleotide and deduced amino acid sequence of the clone GluR2.

Sequence ID No. 4 is the deduced amino acid sequence of the clone GluR2.

Sequence ID No. 5 shows the nucleotide and deduced amino acid sequence of the clone GluR3.

Sequence ID No. 6 is the deduced amino acid sequence of the clone GluR3.

Sequence ID No. 7 shows the nucleotide and deduced amino acid sequence of the clone GluR4.

Sequence ID No. 8 is the deduced amino acid sequence of the clone GluR4.

Sequence ID No. 9 shows the nucleotide and deduced amino acid sequence of the cDNA clone encoding glutamate receptor subunit GluR5-1.

Sequence ID No. 10 is the deduced amino acid sequence of the clone GluR5.

Sequence ID No. 11 shows the nucleotide and deduced amino acid sequence of the clone GluR6.

Sequence ID No. 12 is the deduced amino acid sequence of the clone GluR6.

Sequence ID No. 13 shows the nucleotide and deduced amino acid sequence of fragments clone GluR7.

Sequence ID No. 14 is the deduced amino acid sequence of the clone GluR7.

What is claimed is:

1. A substantially pure polypeptide, wherein said polypeptide comprises the amino acid sequence of GluR1 (Sequence ID No. 2), GluR2 (Sequence ID No. 4), GluR3 (Sequence ID No. 6), GluR4 (Sequence ID No. 8), GluR5 (Sequence ID No. 10), GluR6 (Sequence ID No. 12), or GluR7 (Sequence ID No. 14), and immunologically reactive fragments thereof.

2. A polypeptide according to claim 1, said immunologically reactive fragements comprising at least 15 contiguous amino acids of GluR1 (Sequence ID No. 2), GluR2

(Sequence ID No. 4), GluR3 (Sequence ID No. 6), GluR4 (Sequence ID No. 8), GluR5 (Sequence ID No. 10), GluR6 (Sequence ID No. 12), or GluR7 (Sequence ID No. 14).

3. A composition comprising a recombinant homomeric receptor formed of any one of the polypeptides GluR1 (Sequence ID No. 2), GluR2 (Sequence ID No. 4), GluR3 (Sequence ID No. 6), GluR4 (Sequence ID No. 8), GluR5 (Sequence ID No. 10), GluR6 (Sequence ID No. 12), or GluR7 (Sequence ID No, 14).

4. A composition comprising a recombinant heteromeric receptor formed of any two or more of the polypeptides GluR1 (Sequence ID No. 2), GluR2 (Sequence ID No. 4), GluR3 (Sequence ID No. 6), GluR4 (Sequence ID No. 8), GluR5 (Sequence ID No. 10), GluR6 (Sequence ID No. 12), or GluR7 (Sequence ID No. 14).

5. A substantially pure mammalian polypeptide, wherein said polypeptide is encoded by a cDNA which hybridizes under low stringency conditions to the complement of a nucleic acid having a nucleotide sequence selected from the group consisting of SEQ ID NO:1, SEQ ID NO:3, SEQ ID NO:5, SEQ ID NO:7, SEQ ID NO:9, SEQ ID NO:11 and SEQ ID NO: 13.

6. A substantially pure mammalian polypeptide according to claim 5 wherein said nucleotide sequence is SEQ ID NO:1.

7. A substantially pure mammalian polypeptide according to claim 5 wherein said nucleotide sequence is SEQ ID NO:3.

8. A substantially pure mammalian polypeptide according to claim 5 wherein said nucleotide sequence is SEQ ID NO:5.

9. A substantially pure mammalian polypeptide according to claim 5 wherein said nucleotide sequence is SEQ ID NO:7.

10. A substantially pure mammalian polypeptide according to claim 5 wherein said nucleotide sequence is SEQ ID NO:9.

11. A substantially pure mammalian polypeptide according to claim 5 wherein said nucleotide sequence is SEQ ID NO:11.

12. A substantially pure mammalian polypeptide according to claim 5 wherein said nucleotide sequence is SEQ ID NO:13.

* * * * *